United States Patent [19]

Walker et al.

[11] Patent Number: 5,158,949

[45] Date of Patent: Oct. 27, 1992

[54] 1,3-DIOXOLANE DERIVATIVES AS CHOLESTEROL-LOWERING AGENTS

[75] Inventors: Keith A. Walker, Los Altos Hills; Pamela M. Burton, Redwood City; David C. Swinney, San Mateo, all of Calif.

[73] Assignee: Syntex (U.S.A.) Inc., Palo Alto, Calif.

[21] Appl. No.: 633,599

[22] Filed: Dec. 20, 1990

[51] Int. Cl.$^5$ ............... A61K 31/415; C07D 405/06; C07D 405/14

[52] U.S. Cl. ............... 514/227.8; 514/235.8; 514/252; 514/326; 514/397; 514/231.5; 544/60; 544/139; 544/370; 546/210; 548/311.1; 548/314.7

[58] Field of Search ............. 548/336; 514/397, 227.8, 514/235.8, 252, 326, 231.5; 544/60, 139, 370; 546/210

[56] References Cited

U.S. PATENT DOCUMENTS

| | | | |
|---|---|---|---|
| 4,078,071 | 3/1978 | Walker et al. | 548/341 |
| 4,144,346 | 3/1979 | Heeres et al. | 548/336 |
| 4,321,272 | 3/1982 | Walker et al. | 548/336 |
| 4,335,125 | 6/1982 | Heeres et al. | 548/336 |
| 4,359,475 | 11/1982 | Walker et al. | 548/336 |
| 4,375,474 | 3/1983 | Walker et al. | 548/336 |
| 4,490,540 | 12/1984 | Heeres et al. | 548/336 |
| 4,518,607 | 5/1985 | Walker et al. | 514/399 |
| 4,940,799 | 7/1990 | Aebi et al. | 548/268.8 |

FOREIGN PATENT DOCUMENTS

0052905 6/1982 European Pat. Off. .

OTHER PUBLICATIONS

*Journal of Lipid Research*, (1988), vol. 29, pp. 43-51.
*J. Steroid Biochem.*, (1987), vol. 28, No. 5, pp. 521-531.
*J. Androl.* (1987, vol. 8, pp.230-237.
*Am. J. Trop. Med. Hyg.*, (1987), vol. 37, No. 2, pp.308-313.
*The American Journal of Medicine* (1986), vol. 80, pp. 616-621.
*The Journal of Pharmacology and Experimental Therapeutics* (1986), vol. 238, No. 3, pp.905-911.
*Eur. J. Clin. Pharmacol.* (1985), vol. 29, pp.241-245.
*Male Contraception: Advances and Future Prospects* (1985), Chap. 25, pp. 271-292.
*Arch. Intern. Med.* (1982), vol. 142, pp. 2137-2140.
*Pesticide Chemistry: Human Welfare and the Environment, Proc. Int. Congr. Pestic. Chem.* 5th (1982), vol. 1, pp.303-308.

Primary Examiner—Floyd D. Higel
Assistant Examiner—Lenora Miltenberger
Attorney, Agent, or Firm—Carol J. Roth; Derek P. Freyberg; Tom M. Moran

[57] ABSTRACT

Compounds of formula (I):

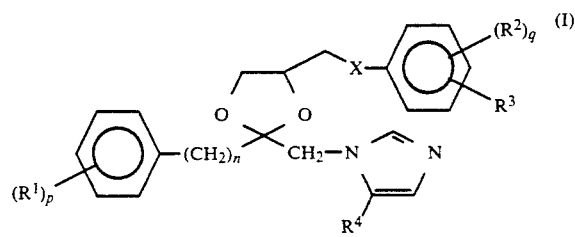

wherein
n is 2 or 3;
p is 0, 1 or 2;
q is 0, 1 or 2;
X is oxygen or $S(O)_t$ where t is 0, 1 or 2;
each $R^1$ is independently halo, lower alkyl, lower alkoxy, or trifluoromethyl;
each $R^2$ is independently halo or lower alkyl;
$R^3$ is nitro or $-N(R^5)R^6$ where
  $R^5$ is hydrogen or lower alkyl;
  $R^6$ is hydrogen lower alkyl, lower alkylsulfonyl or $-C(Y)R^7$ where Y is oxygen or sulfur and $R^7$ is hydrogen, lower alkyl, lower alkoxy or $-N(R^8)R^9$ where $R^8$ is hydrogen or lower alkyl and $R^9$ is hydrogen, lower alkyl or lower alkoxycarbonyl; or
  $R^5$ and $R^6$ together with N is pyrrolidino, piperidino, morpholino, thiomorpholino or piperazino, wherein the piperazino is optionally substituted at the 4-position by $-N(O)R^{10}$ where $R^{10}$ is hydrogen, lower alkyl, lower alkoxy or amino; and
$R^4$ is hydrogen or lower alkyl, as single stereoisomers or as mixtures thereof; and their pharmaceutically acceptable salts, are useful in treating disease-states characterized by hypercholesterolemia.

38 Claims, No Drawings

1,3-DIOXOLANE DERIVATIVES AS CHOLESTEROL-LOWERING AGENTS

BACKGROUND OF THE INVENTION

1. Field of the Invention

This invention relates to 1,3-dioxolane derivatives that are useful in treating mammals having disease-states characterized by hypercholesterolemia.

2. Related Disclosures

Ketoconazole is a 1,3-dioxolane derivative useful as an antifungal antibiotic that is known to inhibit cholesterol synthesis. See, e.g., *Journal of Lipid Research* (1988), Vol. 29, pp. 43–51; *The American Journal of Medicine* (1986), Vol. 80, pp. 616–621; *Eur. J. Clin. Pharmacol.* (1985), Vol. 29, pp. 241–245; *The Journal of Pharmacology and Experimental Therapeutics* (1986), Vol. 238, No. 3, pp. 905–911.

Fungicidal activity of individual enantiomers of another 1,3-dioxolane derivative, etaconazole, is described in *Pesticide Chemistry, Human Welfare and the Environment, Proc. Int. Congr. Pestic. Chem.* 5th (1983), Vol. 1, pp. 303–308.

Various 1,3-dioxolane derivatives useful as antifungal, antibacterial and antineoplastic agents are disclosed in U.S. Pat. Nos. 4,078,071 (Syntex); 4,144,346 (Janssen); 4,321,272 (Syntex); 4,335,125 (Janssen); 4,359,475 (Syntex); 4,375,474 (Syntex); 4,490,540 (Janssen); and 4,518,607 (Syntex); and in European Published Patent Application No. 0 052 905 (Janssen).

The spermicidal activity of certain 2-(imidazol-1-yl)methyl-2-(2-phenylethyl)-4-(phenoxymethyl)-1,3-dioxolane derivatives is discussed in *Journal of Andrology* (1987), Vol. 8, pp. 230–237, and *Male Contraception: Advances and Future Prospects* (1985), Chapter 25, pp. 271–292. The anti-parasitic activity of a similar derivative is disclosed in *Am. J. Trop. Med. Hyg.* (1987), Vol. 37, No. 2, pp. 308–313.

The disclosures of these and all other documents referred to within this specification are incorporated herein in whole by reference.

SUMMARY OF THE INVENTION

In one aspect, this invention provides a method of treating a mammal having a disease-state characterized by hypercholesterolemia, which method comprises administering to a mammal in need thereof a therapeutically effective amount of a compound of formula (I):

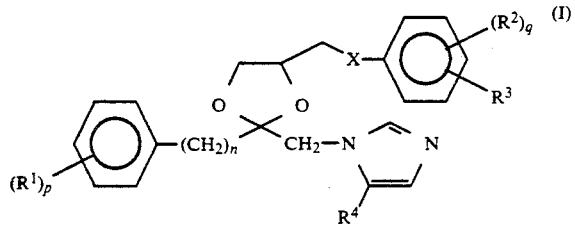

wherein
n is 2 or 3;
p is 0, 1 or 2;
q is 0, 1 or 2;
X is oxygen or $S(O)_t$ where t is 0, 1 or 2;
each $R^1$ is independently halo, lower alkyl, lower alkoxy, or trifluoromethyl;
each $R^2$ is independently halo or lower alkyl;
$R^3$ is nitro or $-N(R^5)R^6$ where
$R^5$ is hydrogen or lower alkyl;
$R^6$ is hydrogen, lower alkyl, lower alkylsulfonyl or $-C(Y)R^7$ where Y is oxygen or sulfur and $R^7$ is hydrogen, lower alkyl, lower alkoxy or $-N(R^8)R^9$ where $R^8$ is hydrogen or lower alkyl and $R^9$ is hydrogen, lower alkyl or lower alkoxycarbonyl; or
$R^5$ and $R^6$ together with N is pyrrolidino, piperidino, morpholino, thiomorpholino or piperazino, wherein the piperazino is optionally substituted at the 4-position by $-C(O)R^{10}$ where $R^{10}$ is hydrogen, lower alkyl, lower alkoxy or amino; and
$R^4$ is hydrogen or lower alkyl, as a single stereoisomer or as a mixture thereof; or a pharmaceutically acceptable salt thereof.

In another aspect, this invention provides a pharmaceutical composition useful in treating a mammal having a disease-state characterized by hypercholesterolemia, which composition comprises a therapeutically effective amount of a compound of formula (I) as defined above; as a single stereoisomer or as a mixture thereof; or a pharmaceutically acceptable salt thereof; and a pharmaceutically acceptable excipient.

In another aspect, this invention provides compounds of formula (I) wherein n, p, q, $R^1$, $R^2$, $R^3$ and $R^4$ are as defined above and X is $S(O)_t$ where t is 0, 1 or 2; as single stereoisomers or as mixtures thereof; or pharmaceutically acceptable salts thereof.

In another aspect, this invention provides compounds of formula (I) wherein n, p, q, $R^1$, $R^2$ and $R^4$, are as defined above, X is oxygen and $R^3$ is nitro or $-N(R^5)R^6$ where $R^5$ is hydrogen or lower alkyl; $R^6$ is hydrogen, lower alkyl, lower alkylsulfonyl or $-C(Y)R^7$ where Y is oxygen or sulfur and $R^7$ is hydrogen, lower alkyl or $-N(R^8)R^9$ where $R^8$ is hydrogen or lower alkyl and $R^9$ is hydrogen, lower alkyl or lower alkoxycarbonyl; or $R^5$ and $R^6$ together with N is morpholino, thiomorpholino or piperazino wherein the piperazino is optionally substituted at the 4-position by $-C(O)R^{10}$ where $R^{10}$ is hydrogen, lower alkyl, lower alkoxy or amino; as single stereoisomers or as mixtures thereof; or pharmaceutically acceptable salts thereof.

In another aspect, this invention provides a process for preparing compounds of formula (I), as single stereoisomers, or as mixtures thereof; or pharmaceutically acceptable salts thereof.

DETAILED DESCRIPTION OF THE INVENTION

Definitions

As used in the specification and appended claims, unless specified to the contrary, the following terms having the meaning indicated:

The term "lower alkyl" refers to a straight or branched chain monovalent radical consisting solely of carbon and hydrogen, containing no unsaturation and having from one to four carbon atoms, e.g., methyl, ethyl, n-propyl, 1-methylethyl, n-butyl, 1,1-dimethylethyl, 1-methylpropyl, and the like.

The term "lower alkoxy" refers to a radical of the formula $-OR_a$ where $R_a$ is lower alkyl as defined above, e.g., methoxy, ethoxy, n-propoxy, 1-methylethoxy, n-butoxy, and the like.

The term "halo" refers to a halogen radical, i.e., fluoro, chloro, bromo, or iodo.

The term "amino" refers to the radical $-NH_2$.

The term "lower monoalkylamino" refers to an amino radical, as defined above, which is substituted by one lower alkyl radical, as defined above, e.g., methylamino, ethylamino, n-propylamino, n-butylamino, 2,2-dimethylethylamino, and the like.

The term "lower dialkylamino" refers to an amino radical, as defined above, which is substituted by two lower alkyl radicals, as defined above, e.g., dimethylamino, diethylamino, di-n-propylamino, di-n-butylamino, and the like.

The term "acetyl" refers to the radical —C(O)CH$_3$.

The term "acetamido" refers to the radical —NHC(O)CH$_3$.

The term "aminocarbonylamino" refers to the radical —NHC(O)NH$_2$.

The term "aminothiocarbonylamino" refers to the radical —NHC(S)NH$_2$.

The term "lower alkylsulfonyl" refers to a radical of the formula —S(O)$_2$R$_b$ where R$_b$ is lower alkyl as defined above, e.g., methylsulfonyl, ethylsulfonyl, n-propysulfonyl, n-butylsulfonyl, 2-methylpropylsulfonyl, and the like.

The term "lower alkoxycarbonyl" refers to the radical of the formula —C(O)R$_c$ where R$_c$ is lower alkoxy as defined above, e.g., methoxycarbonyl, ethoxycarbonyl, n-propoxycarbonyl, n-butoxycarbonyl, 2-methylpropoxycarbonyl, and the like.

The term "lower alkoxycarbonylamino" refers to the radical of the formula —NHR$_d$ where R$_d$ is lower alkoxycarbonyl as defined above, e.g., methoxycarbonylamino, ethoxycarbonylamino, n-propoxycarbonylamino, n-butoxycarbonylamino, 2-methylpropoxycarbonylamino, and the like.

The term "lower alkylsulfonylamino" refers to the radical of the formula —NHR$_e$ where R$_e$ is lower alkylsulfonyl as defined above, e.g., methylsulfonylamino, ethylsulfonylamino, n-propylsulfonylamino, n-butylsulfonylamino, 2-methylpropylsulfonylamino, and the like.

The term "alkanol" refers to a branched or unbranched aliphatic hydrocarbon of 1 to 10 carbons wherein one hydroxyl radical is attached thereto.

The term "stereoisomers" refers to compounds having identical molecular formulae and nature or sequence of bonding but differing in the arrangement of their atoms in space.

The term "enantiomer" refers to stereoisomers which are mirror images of each other.

The term "diastereomer" refers to stereoisomers which are not mirror images of each other.

The term "leaving group" refers to a group displaceable in a nucleophilic reaction, for example, halo, e.g., bromo; or aryl or alkyl sulfonate esters, e.g., mesyl or tosyl ester. Preferred leaving groups for the purpose of this invention are mesyl and tosyl esters.

The term "optionally" means that the subsequently described event or circumstance may or may not occur, and that the description includes instances where the event or circumstance occurs and instances wherein it does not.

The term "pharmaceutically acceptable salt" refers to those salts which retain the biological effectiveness and properties of the free bases of the invention and which are not biologically or otherwise undesirable. These salts may be prepared from either inorganic acids such as hydrochloric acid, hydrobromic acid, sulfuric acid, nitric acid, phosphoric acid, and the like; or organic acids such as acetic acid, oxalic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

The term "mammal" includes humans and all domestic and wild mammals, including, without limitation, cattle, horses, swine, sheep, goats, dogs, cats, and the like.

The term "hypercholesterolemia" refers to excessive amounts of cholesterol in the blood.

The term "therapeutically effective amount" refers to that amount of a compound of formula (I) which, when administered to a mammal in need thereof, is sufficient to effect treatment, as defined below, for disease-states characterized by hypercholesterolemia. The amount of a compound of formula (I) which constitutes a "therapeutically effective amount" will vary depending on the compound, the disease-state and its severity, and the mammal to be treated, but can be determined routinely by one of ordinary skill in the art having regard to his own knowledge and to this disclosure.

The terms "treating" or "treatment" as used herein cover the treatment of a disease-state in a mammal, particularly in a human, which disease-state is characterized by hypercholesterolemia, and include:

(i) preventing the disease-state from occurring in a mammal, in particular, when such mammal is predisposed to the disease-state but has not yet been diagnosed as having it;

(ii) inhibiting the disease-state, i.e., arresting its development; or (iii) relieving the disease-state, i.e., causing regression of the disease-state.

It is understood, for purposes of this invention, that the two phenyl rings of the molecule can not be substituted with two adjacent tert-butyl groups.

The yield of each of the reactions described herein is expressed as a percentage of the theoretical yield.

The nomenclature used herein is basically a modified form of I.U.P.A.C. nomenclature wherein compounds of the invention are named as derivatives of 1,3-dioxolane. The positions in the compounds are numbered as follows:

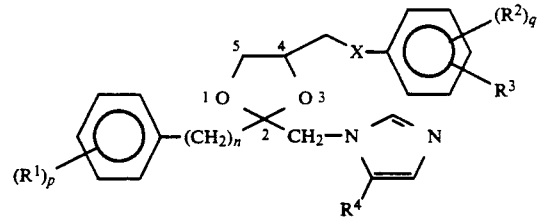

The compounds of formula (I), or their pharmaceutically acceptable salts, have at least two asymmetric carbon atoms in their structure, namely the 2-carbon and 4-carbon of the dioxolane ring, and therefore can exist as four distinct stereoisomers, in particular, as two pairs of enantiomers. All four isomers, or their pharmaceutically acceptable salts, are intended to be within the scope of this invention.

For purposes of this invention, the term "mixture" when used alone in reference to isomers of compounds of formula (I) includes racemic, non-racemic and diastereomeric mixtures of the isomers.

The pair of enantiomers wherein the C-4 substituent and the C-2 imidazolylmethyl substituent are on the same side of the plane of the dioxolane ring, e.g., compounds of the following formulae (Ic) and (If):

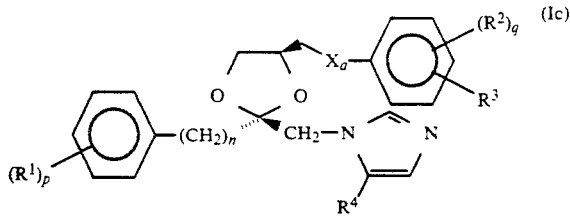

and

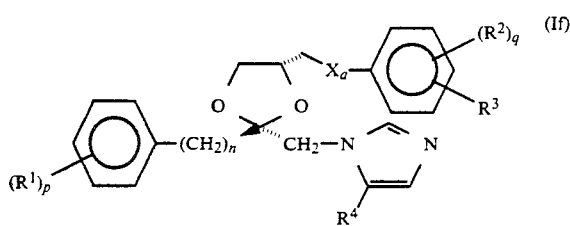

are designated herein as cis-enantiomers of compounds of formula (I).

The enantiomers wherein the C-4 substituent and the C-2 imidazolymethyl substituent are on opposite sides of the plane of the dioxolane ring, e.g., compounds of the following formulae (Id) and (Ie):

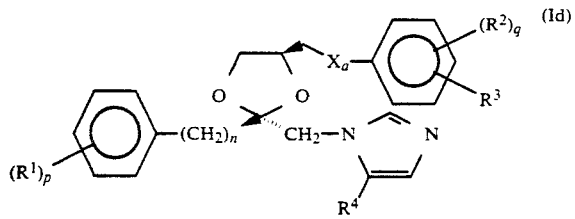

and

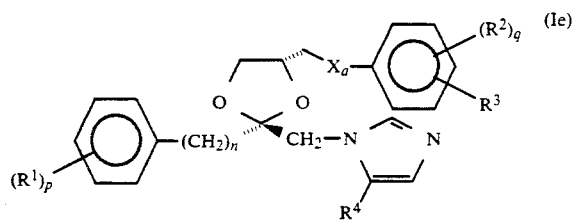

are designated herein as trans-enantiomers of compounds of formula (I).

An absolute descriptor, R or S, may be assigned to the chiral carbon atoms in the individual enantiomers according to the "Sequence Rule" procedure of Cahn, Ingold and Prelog.

For purposes of this invention, racemic mixtures of the cis-enantiomers of formula (I), and intermediates thereof, are designated herein by the (±) symbol and by the formula of the single 2S-cis-enantiomer. For example, compounds of formula (Ia) are racemic mixtures of compounds of formulae (Ic) and (If), and are designated herein by the (±) symbol and formula (Ic) (the formula for the 2S-cis-enantiomer). Similarly, racemic mixtures of the trans-enantiomers of formula (I), and intermediates thereof, are designated herein by the (±) symbol and by the formula of the single 2S-trans-enantiomer. For example, compounds of formula (Ib) are racemic mixtures of compounds of formulae (Id) and (Ie), and are designated herein by the (±)-symbol and formula (Ie) (the formula for the 2-S-trans-enantiomer). For example, a racemic mixture of the cis-enantiomers of formula (I) wherein n is 2, p is 1, q is 0, X is —S(O)$_t$ where t is 0, $R^1$ is chloro in the 4-position, $R^3$ is —NH$_2$ in the 4-position and $R^4$ is hydrogen, is named herein as (±)-cis-2-(2-(4-chlorophenyl)ethyl-2-(imidazol-1-yl)methyl-4-(4-aminophenylthio)methyl-1,3-dioxolane, while the individual cis-enantiomers are named as (2S,4S)-cis-2-(2-(4-chlorophenyl)ethyl-2-(imidazol-1-yl)methyl-4-(4-aminophenylthio)methyl-1,3-dioxolane and as (2R,4R)-cis-2-(2-(4-chlorophenyl)ethyl)-2-(imidazol-1-yl)methyl-4-(4-aminophenylthio)methyl-1,3-dioxolane.

It should be noted that assignment of the absolute descriptors, R and S, to the 4-carbon is dependent on the "X" substituent of formula (I), and does not reflect the cis or trans configuration.

The (±)-cis racemates of formula (I) may be separated from the corresponding (±)-trans racemates of formula (I) by various methods, e.g., by selective crystallization of chromatography, and/or by methods disclosed herein. The individual enantiomers of formula (I) may be resolved by conventional methods known to those of ordinary skill in the art, for example, by crystallization of the diastereomeric salts of the compounds of formula (I), or suitable intermediates, with an optically active acid. Alternatively, the individual enantiomers of formula (I) may be prepared using chiral reagents, as described herein, or by a combination of physical separation and chiral synthesis.

Utility and Administration

A. Utility

The compounds of formula (I), including the pharmaceutically acceptable salts thereof, and the compositions containing them, inhibit cholesterol synthesis and are therefore useful in treating disease-states characterized by hypercholesterolemia. In particular, compounds of formula (I) inhibit cholesterol synthesis by inhibiting lanosterol 14α-demethylase, a cytochrome P-450 enzyme. Certain compounds of formula (I), in particular, those compounds wherein the 2-carbon of the dioxolane ring has the S configuration, are more effective in inhibiting lanosterol 14α-demethylase than they are in inhibiting other cytochrome P-450 enzymes, in particular, those enzymes which contribute to gonadal and adrenal steroidogenesis and cholesterol degradation. Accordingly, these compounds are useful in treating disease-states characterized by hypercholesterolemia with minimum effect on the physiological functions of key cytochrome P-450 enzymes.

B. Testing

The ability of the compounds of formula (I) to effectively inhibit cholesterol synthesis can be determined by a variety of in vitro assays that are known to those of ordinary skill in the art. See, for example, Kraemer, et al., *J. Pharmacol. and Exp. Ther.* (1986), Vol. 238. p. 905. In addition, the ability of certain compounds of formula (I), in particular those compounds wherein the 2-carbon of the dioxolane ring has the S-configuration, to be more effective inhibitors of lanosterol 14α-demethylase than other cytochrome P-450 enzymes, e.g., cholesterol 7α-hydroxylase, progesterone 17α/20 lyase, deoxycorticosterone 11β-hydroxylase, and estrogen synthase, can be determined, for example, by utilizing the assays described in Bossard, M. J., et al., *Bioorg. Chem.* (1989), Vol. 17, pp. 385-399; Trzaskos, J. M., et al., *J. Biol. Chem.* (1986), Vol. 261, pp. 16937-16942; Myant, N. B., et al., *J. Lipid Research* (1977), Vol. 18, ppl. 135-153; Hylemon, P. B., et al., *Anal. Biochem.* (1989), Vol. 182, pp. 212-216; Schatzman, G. L., et al., *Anal. Biochem.* (1988), Vol. 175, pp. 219-226; Nakajin, S., et al., *J. Biol. Chem.* (1981), Vol. 256, pp. 3871-3876; Yanagibashi, K., et al., *J. Biol. Chem.* (1986), Vol. 261, pp. 3556-3562; or Thompson, Jr., E. A., et al., *J. Biol. Chem.* (1974), Vol. 249, pp. 5364-5372; or by utilizing modifications thereof.

The ability of the compounds of formula (I) to effectively lower serum cholesterol can also be demonstrated in well-known in vivo assays, in particular, in vivo assays which utilize animal models that are consistent with the physiological pathways of cholesterol synthesis and degradation in humans, see, e.g., Burton, P. M., et al., *Comp. Biochem. and Physiol.* (1989), Vol. 92, p. 667. Serum is collected and assayed for cholesterol levels, utilizing, inter alia, diagnostic kits which are commercially available, for example, from Sigma Chemical Co. Such kits generally utilize a modification of the method described in Allain, C. A., et al., *Clin. Chem.* (1974), Vol. 20, p. 470, in order to determine serum cholesterol levels.

C. General Administration

Administration of the compounds of formula (I), or their pharmaceutically acceptable salts, in pure form or in an appropriate pharmaceutical composition, can be carried out via any of the accepted modes of administration of agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of formula (I) as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of formula (I), or a pharmaceutically acceptable salt thereof, and 99% to 1% by weight of a suitable pharmaceutical excipient. Preferably, the composition will be about 5% to 75% by weight of a compound(s) of formula (I), or a pharmaceutically acceptable salt thereof, with the rest being suitable pharmaceutical excipients.

The preferred route of administration is oral, using a convenient daily dosage regimen which can be adjusted according to the degree of hypercholesterolemia to be treated. For such oral administration, a pharmaceutically acceptable composition containing a compound(s) of formula (I), or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of formula (I), or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of formula (I) (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of the compound(s) of formula (I), or a pharmaceutically acceptable salt thereof, for relief of hypercholesterolemia when administered in accordance with the teachings of this invention.

Generally, the compounds of formula (I), or their pharmaceutically acceptable salts, are administered in a therapeutically effective amount which will vary depending on the individual and the disease-state characterized by hypercholesterolemia which is being treated. Typically, a therapeutically effective daily dose is from about 0.14 mg to about 14.3 mg/kg of body weight per day of a compound of formula (I), or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of formula (I), or a pharmaceutically acceptable salt thereof, preferably from about 50 mg to about 700 mg per day, and most preferably from about 100 mg to about 500 mg per day.

Preferred Embodiments

One aspect of the invention is the group of compounds of formula (I):

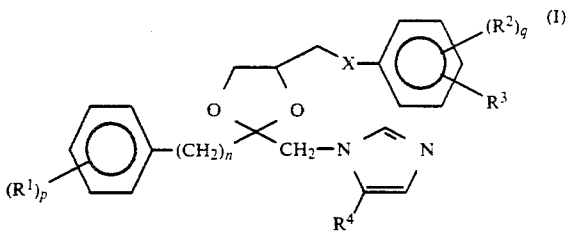

wherein
n is 2 or 3;
p is 0, 1 or 2;
q is 0, 1 or 2;
X is S(O)$_t$ where t is 0, 1 or 2;
each R$^1$ is independently halo, lower alkyl, lower alkoxy, or trifluoromethyl;
each R$^2$ is independently halo or lower alkyl;
R$^3$ is nitro or —N(R$^5$)R$^6$ where
R$^5$ is hydrogen or lower alkyl;
R$^6$ is hydrogen, lower alkyl, lower alkylsulfonyl, or —C(Y)R$^7$ where Y is oxygen or sulfur, and R$^7$ is hydrogen, lower alkyl, lower alkoxy, or —N(R$^8$)R$^9$ where R$^8$ is hydrogen or lower alkyl and R$^9$ is hydrogen, lower alkyl or lower alkoxycarbonyl; or
R$^5$ and R$^6$ together with N is pyrrolidino, piperidino, morpholino, thiomorpholino or piperazino, wherein the piperazino is optionally substituted at the 4-position by —C(O)R$^{10}$ where R$^{10}$ is hydrogen, lower alkyl, lower alkoxy or amino; and R$^4$ is hydrogen or lower alkyl, as single stereoisomers or as mixtures thereof; and their pharmaceutically acceptable salts.

A preferred subgroup of these compounds has the 2-carbon of the dioxolane ring in the S-configuration. A preferred class of these compounds has n as 2, q as 0, and R$^4$ as hydrogen. A preferred subclass of these compounds is that subclass wherein R$^3$ is in the 4-position and is —N(R$^5$)R$^6$ where R$^5$ is hydrogen or lower alkyl and R$^6$ is hydrogen, lower alkyl, lower alkylsulfonyl or —C(Y)R$^7$ where Y is oxygen or sulfur and R$^7$ is hydrogen, lower alkyl or —N(R$^8$)R$^9$ where R$^8$ is hydrogen or lower alkyl and R$^9$ is hydrogen, lower alkyl or lower alkoxycarbonyl.

A preferred group of these compounds has R$^1$ as chloro, fluoro, methyl or methoxy. A preferred subgroup of these compounds has R$^5$ as hydrogen and R$^6$ as hydrogen or —C(Y)R$^7$ where Y is oxygen and R$^7$ is hydrogen, lower alkyl or lower alkoxy. The more preferred compounds within this subgroup are those wherein t is 0 and R$^1$ is chloro in the 4-position. The most preferred compounds are the individual cis-enantiomers wherein R$^6$ is hydrogen or acetyl.

Another aspect of the invention is the group of compounds of formula (I):

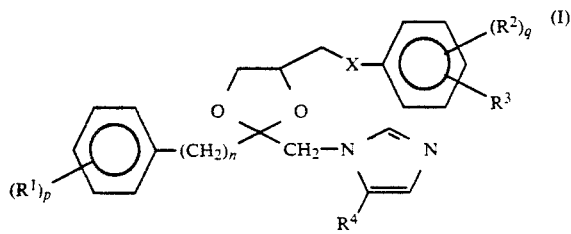

wherein
n is 2 or 3;
p is 0, 1 or 2;
q is 0, 1 or 2;
X is oxygen;
each R$^1$ is independently halo, lower alkyl, lower alkoxy, or trifluoromethyl;
each R$^2$ is independently halo or lower alkyl;
R$^3$ is nitro or —N(R$^5$)R$^6$ where
R$^5$ is hydrogen or lower alkyl;
R$^6$ is hydrogen, lower alkyl, lower alkylsulfonyl, or —C(Y)R$^7$ where Y is oxygen or sulfur, and R$^7$ is hydrogen, lower alkyl or —N(R$^8$)R$^9$ where R$^8$ is hydrogen or lower alkyl and R$^9$ is hydrogen, lower alkyl or lower alkoxycarbonyl; or
R$^5$ and R$^6$ together with N is morpholino, thiomorpholino or piperazino, wherein the piperazino is optionally substituted at the 4-position by —C(O)R$^{10}$ where R$^{10}$ is hydrogen, lower alkyl, lower alkoxy or amino; and
R$^4$ is hydrogen or lower alkyl, as single stereoisomers or as mixtures thereof; and their pharmaceutically acceptable salts.

A preferred subgroup of these compounds has the 2-carbon of the dioxolane ring in the S-configuration. A preferred class of these compounds has n as 2, q as 0, and R$^4$ as hydrogen. A preferred subclass of these compounds is that subclass wherein R$^3$ is in the 4-position and is —N(R$^5$)R$^6$ where R$^5$ is hydrogen or lower alkyl and R$^6$ is hydrogen, lower alkyl, lower alkylsulfonyl or —C(Y)R$^7$ where Y is oxygen or sulfur and R$^7$ is hydrogen, lower alkyl or —N(R$^8$)R$^9$ where R$^8$ is hydrogen or lower alkyl and R$^9$ is hydrogen, lower alkyl or lower alkoxycarbonyl.

A preferred group of these compounds has R$^1$ as chloro, fluoro, methyl or methoxy. A preferred subgroup of these compounds has R$^5$ as hydrogen and R$^6$ as hydrogen or —C(Y)R$^7$ where Y is oxygen and R$^7$ is hydrogen or lower alkyl. The more preferred compounds within this subgroup are those wherein R$^1$ is chloro in the 4-position. The most preferred compounds are the individual cis-enantiomers wherein R$^6$ is hydrogen or acetyl.

Presently, the most preferred compounds of this invention are:
(2S,4S)-cis-2-(2-(4-chlorophenyl)ethyl)-2-(imidazol-1-yl)methyl-4-(4-aminophenylthio)methyl-1,3-dioxolane; and
(2S,4S)-cis-2-(2-(4-chlorophenyl)ethyl)-2-(imidazol-1-yl)methyl-4-(4-acetamidophenylthio)methyl-1,3-dioxolane; or
pharmaceutically acceptable salts thereof.

Preparation of Compounds of Formula (I)

Compounds of formula (I) are compounds of formulae (Ia), (Ib), (Ic), (Id), (Ie) and (If), and are prepared by the following procedures.

A. Preparation of Compounds of Formula (A) where n is 2 or 3 and R$^4$ is hydrogen.

Compounds of formula (A) are used in the preparation of compounds of formula (I). Compounds of formula (A) where n is 2 or 3 and R$^4$ is hydrogen are prepared as shown in the following Reaction Scheme 1 where n is 2 or 3; m is 1 or 2; p is 0, 1 or 2; each R$^1$ is independently halo, lower alkyl, lower alkoxy or trifluoromethyl; R$^4$ is hydrogen and each Z is independently chloro, bromo or iodo:

REACTION SCHEME 1

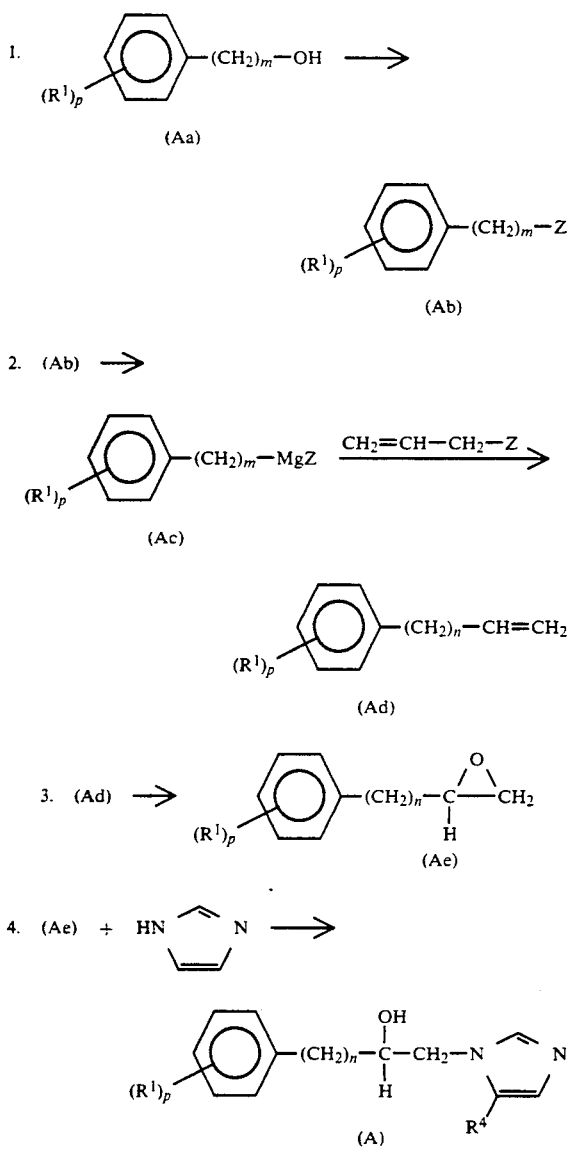

Imidazole and compounds of formula (Aa) are commercially available, for example, from Aldrich Chemical Co., or may be readily prepared by methods known to one skilled in the art, for example by reduction of the appropriate phenylacetic acid.

Compounds of formula (Aa) are treated with a halogenating agent, for example, N-bromosuccinimide and triphenylphosphine, under anhydrous conditions, for example, in dry tetrahydrofuran at reduced temperatures, to form compounds of formula (Ab). The Grignard reagents of formula (Ac) are then prepared under the usual conditions, i.e., in anhydrous ethereral solvents and at temperatures between about −20° C. and 50° C., preferably between about 0° C. and 20° C. The Grignard reagents are then treated with an allyl halide, for example, allyl bromide, to form the alkenes of formula (Ad). Epoxidation of these compounds is performed by treatment with a peracid, for example, peracetic acid, in an aprotic solvent, for example, dichloromethane, at reflux temperatures, to afford compounds of formula (Ae).

The preparation of compounds of formula (A) wherein n is 2 or 3 and $R^4$ is hydrogen is carried out by opening a terminal epoxide of formula (Ae) with imidazole. This reaction is generally carried out using at least one mole and preferably an excess of imidazole relative to the epoxide. The reaction may either be carried out in the absence of solvent or, preferably, in an inert organic solvent, for example, a solvent such as dimethylformamide, hexamethylphosphoramide, acetonitrile, and the like. The epoxide opening is preferably carried out using a metal salt (preferably an alkali metal salt) of imidazole, e.g., the sodium salt of imidazole, used catalytically in the presence of imidazole free base as a proton source. A preferred solvent is dimethylformamide. The temperature normally employed for such epoxide opening is in the range of from about −20° to about 100° C., preferably from about 20° to about 85° C.

B. Preparation of Compounds of formula (B) wherein $R^4$ is lower alkyl

Compounds of formula (B) wherein $R^4$ is lower alkyl are used in the preparation of compounds of formula (I) and are prepared as shown in the following Reaction Scheme 2 wherein n is 2 or 3; p is 0, 1 or 2; each $R^1$ is independently halo, lower alkyl, lower alkoxy or trifluoromethyl; $R^4$ is lower alkyl; W is a bulky protecting group, e.g., triphenylmethyl; and Z is chloro, bromo or iodo:

REACTION SCHEME 2

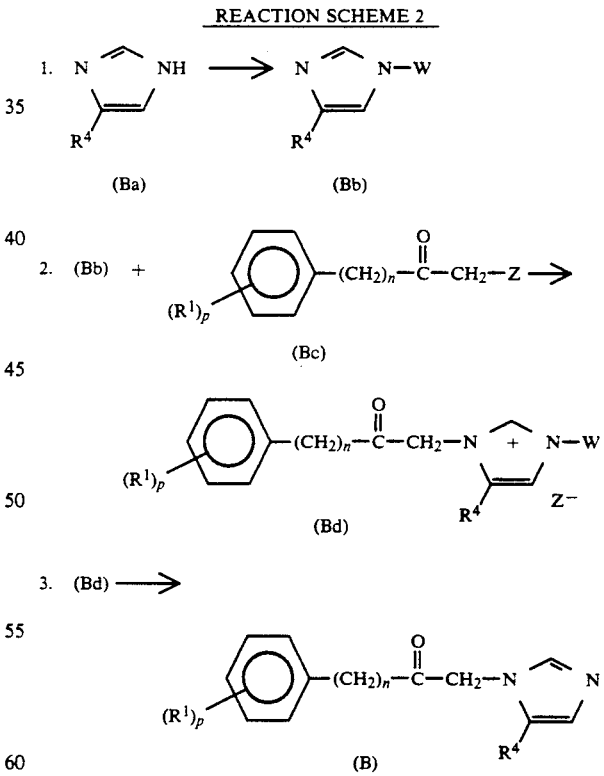

Imidazoles of formula (Af) wherein $R^4$ is lower alkyl are commercially available, for example, from Aldrich Chemical Co., or may be readily prepared by methods known to one skilled in the art.

Compounds of formula (Bc) may be prepared, for example, by the methods described in U.S. Pat. No. 4,375,474, or by methods known to one skilled in the art, for example, by oxidizing the corresponding alcohol, e.g., with Jones reagent. (The corresponding alcohols may be prepared by the methods described in *J. Med. Chem.* (1978), Vol. 21, p. 840, and *J. Amer. Chem. Soc.* (1930), Vol. 52, p. 1164.)

In general, compounds of formula (B) where $R^4$ is lower alkyl are prepared by first treating an imidazole of formula (Af) wherein $R^4$ is lower alkyl with a suitable bulky N-protecting agent, e.g. triphenylmethyl chloride, in an aprotic solvent, preferably dimethylformamide, to form compounds of formula (Bb). Compounds of formula (Bc) are then treated with the compounds of formula (Bb) in an inert organic solvent, such as acetonitrile or dimethylformamide, to give an intermediate imidazolium salt of formula (Bd) which is then hydrolyzed in situ or as a separate step to form compounds of formula (B).

C. Preparation of Compounds of Formulae (Ia) and (Ib).

A compound of formula (Ia) is a racemic mixture of the cis-enantiomers of a compound of formula (I) wherein n is 2 or 3; p is 0, 1 or 2; q is 0, 1 or 2; X is oxygen or $S(O)_t$ where t is 0; each $R^1$ is independently halo, lower alkyl, lower alkoxy, or trifluoromethyl; each $R^2$ is independently halo or lower alkyl; $R^3$ is nitro or $-N(R^5)R^6$ where $R^5$ is hydrogen or lower alkyl; $R^6$ is hydrogen, lower alkyl, lower alkylsulfonyl or $-C(Y)R^7$ where Y is oxygen or sulfur and $R^7$ is hydrogen, lower alkyl, lower alkoxy or $-N(R^8)R^9$ where $R^8$ is hydrogen or lower alkyl and $R^9$ is hydrogen, lower alkyl or lower alkoxycarbonyl; or $R^5$ and $R^6$ together with N is pyrrolidino, piperidino, morpholino, thiomorpholino or piperazino wherein the piperazino is optionally substituted at the 4-position by $-C(O)R^{10}$ where $R^{10}$ is hydrogen, lower alkyl, lower alkoxy or amino; and $R^4$ is hydrogen or lower alkyl.

A compound of formula (Ib) is the corresponding racemic mixture of the trans-enantiomers.

Compounds of formulae (Ia) and (Ib) are prepared as shown in the following Reaction Scheme 3 wherein n, p, q, $R^1$, $R^2$, $R^3$ and $R^4$ are as defined above, $X_a$ is oxygen or sulfur, and $R^{11}$ is a leaving group:

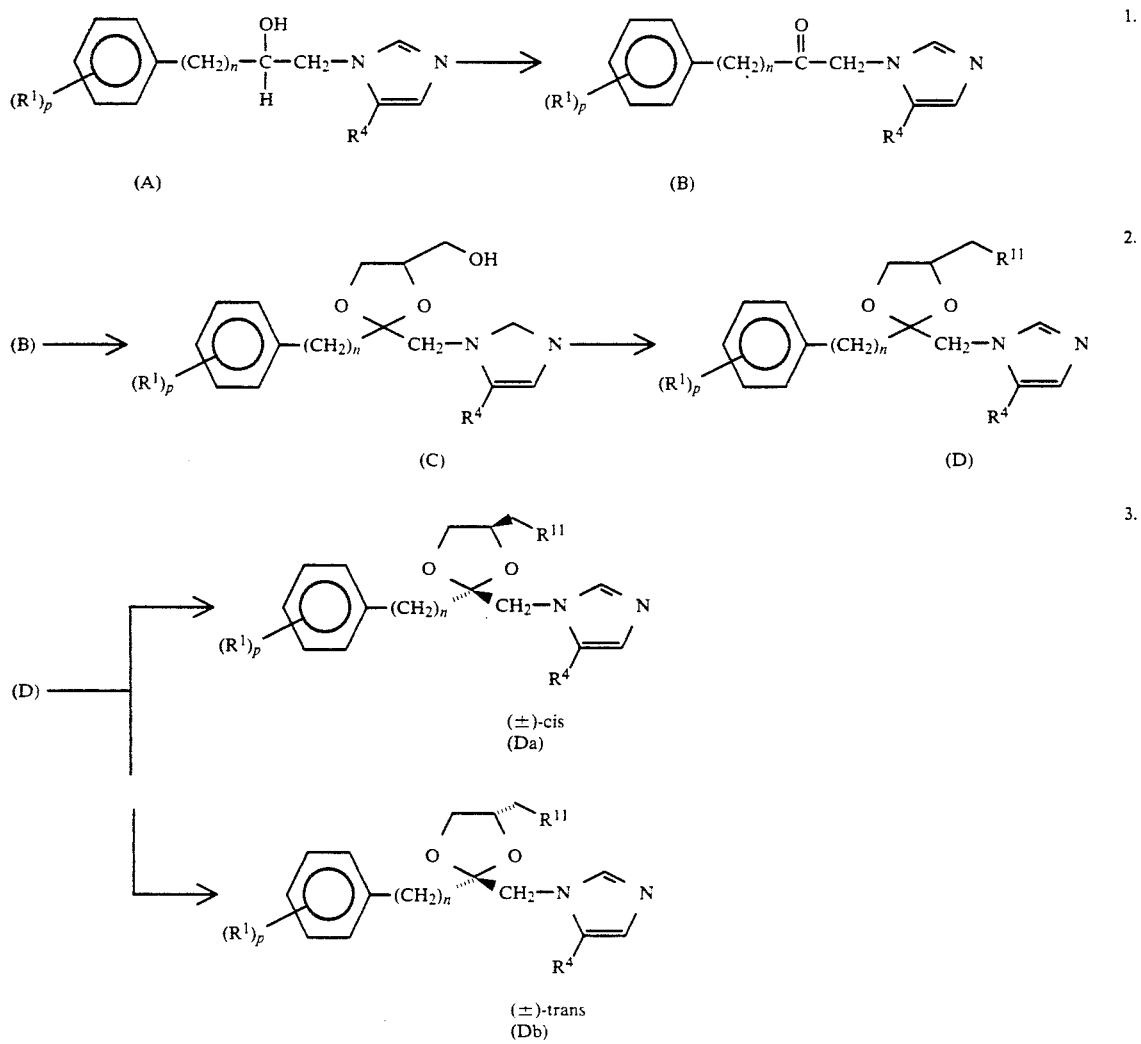

-continued
REACTION SCHEME 3

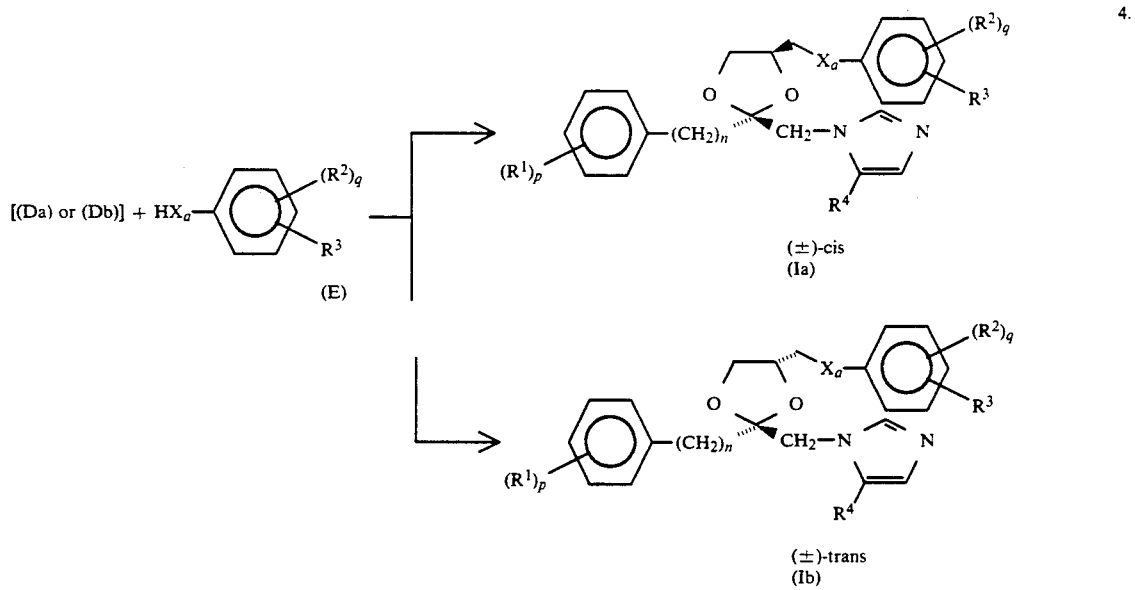

$(\pm)$-cis
(Ia)

$(\pm)$-trans
(Ib)

Compounds of formula (A) where n is 2 or 3 and $R^4$ is hydrogen may be prepared according to the methods described in U.S. Pat. Nos. 4,518,607 and 4,078,071 (Syntex), or by the methods described in *J. Med. Chem.* (1978), Vol. 21, p. 840, and *J. Amer. Chem. Soc.* (1930), Vol. 52, p. 1164, or by the method described in Section A above. Compounds of formula (B) where n is 2 or 3 and $R^4$ is lower alkyl may alternatively be prepared by methods known to one of ordinary skill in the art or by the methods described in Section B above.

The phenols and thiophenols of formula (E) are commercially available, e.g., from Aldrich Chemical Co., or may be readily prepared according to methods known to one of ordinary skill in the art, e.g., according to the methods described in *Coll. Czech. Chem. Commun.* (1934), Vol. 6, No. 211; *J. Amer. Chem. Soc.* (1953), Vol. 75, p. 5281; *Org. Prep. Procedures* (1969), Vol. 1, pp. 87–90; or *Chem. Listy* (1952), Vol. 46, pp. 237–40. Thiophenols may also be prepared, for example, from the appropriate substituted phenol by the method described in *J. Org. Chem.* (1966), Vol. 31, p. 3980, i.e., by pyrolysis of the thionecarbamate and hydrolysis of the resulting thiolcarbamate. Alternatively, the phenols and thiophenols of formula (E) wherein $R^3$ is —$N(R^5)R^6$ where $R^5$ is hydrogen or lower alkyl and $R^6$ is lower alkylsulfonyl or —$C(Y)R^7$ where Y is oxygen or sulfur and $R^7$ is hydrogen, lower alkyl, lower alkoxy or —$N(R^8)R^9$ where $R^8$ is hydrogen or lower alkyl and $R^9$ is hydrogen, lower alkyl or lower alkoxycarbonyl, may be prepared in a similar manner as described below for compounds of formula (Ia) and (Ib) from the corresponding optionally O-protected compounds of formula (E) wherein $R^3$ is —$N(R^5)R^6$ where $R^5$ is hydrogen or lower alkyl and $R^6$ is hydrogen, followed by liberation of the free —OH or —SH group, as appropriate.

In general, compounds of formulae (Ia) and (Ib) are prepared by first oxidizing an alcohol of formula (A), for example, by the method of Swern using dimethyl sulfoxide activated by, e.g., oxalyl chloride, to give the ketone of formula (B) wherein $R^4$ is hydrogen (see, e.g., U.S. Pat. No. 4,375,474 (Syntex) and *J. Org. Chem.* (1979), Vol. 44, No. 23, p. 4148). Alternatively, compounds of formula (B) wherein $R^4$ is lower alkyl are prepared by the method described above in Section B.

Compounds of formula (B), or salts thereof, are then ketalized to form a compound of formula (C) by treatment with glycerol in the presence of 1.02 molar equivalents to 2.0 molar equivalents of an acid or a Lewis acid, e.g., p-toluenesulfonic acid, perchloric acid, fuming sulfuric acid, boron trifluoride, zinc chloride and the like. A sulfonic acid, particularly p-toluenesulfonic acid is most preferred. When a salt of a compound of formula (B) is used only a catalytic amount of the acid or Lewis acid is required. The reaction is generally carried out using from 1 to 10 moles, preferably from 1 to 5 moles of glycerol relative to one mole of the compound of formula (B). Water is preferably removed as an azeotrope with a solvent, for example, a hydrocarbon such as cyclohexane or an aromatic hydrocarbon such as benzene or toluene, at a temperature sufficient to effect such azeotropic removal, e.g., from about 75° C. to about 150° C.

Compounds of formula (B) may also be ketalized to compounds of formula (C) by reaction with glycerol in a molar ratio of about 1:1 in an excess of a simple alcohol, for example, methanol, ethanol, n-butanol or benzyl alcohol in the presence of an appropriate amount (as described above) of an acid or a Lewis acid, e.g., p-toluenesulfonic acid, boron trifluoride, tin (IV) chloride and the like to form compounds of formula (C).

Compounds of formula (C) may also be prepared by other methods known to one of ordinary skill in the art, such as by exchange with the ketal of a low boiling ketone.

Compounds of formula (C) are then converted to the halide or sulfonate ester by means well known in the art. For example, the compound may be halogenated using a halogenating agent such as thionyl chloride or thionyl bromide, either neat, or in an inert organic solvent such as dichloromethane or chloroform, at a temperature between about 0° C. and 80° C., preferably between about 20° C. and 80° C. The halogenation reaction may be carried out in the presence of a molar equivalent or excess of a base (e.g., pyridine) if desired. Alternate halogenation procedures include, for example, the use of triphenylphosphine with either carbon tetrachloride, carbon tetrabromide, or N-chloro- or N-bromosuccinimide. Sulfonate esters may be prepared by the standard procedure of treating the alcohol with at least a stoichiometric amount to about a 100% excess (preferably 10% to 20% excess) of, for example, mesyl chloride or tosyl chloride, preferably mesyl chloride, in the presence of a base, for example, pyridine or triethylamine, at temperatures from about −20° C. to about 50° C., preferably between about 0° C. and about 20° C., to form compounds of formula (D).

Compounds of formula (D) are then separated into the compounds of formula (Da), which are racemic mixtures of the cis-enantiomers of formula (D), and the compounds of formula (Db), which are racemic mixtures of the trans-enantiomers of formula (D). This separation is accomplished by, e.g., fractional crystallization or column chromatography.

Alternatively, compounds of formula (C) may be esterified by treatment with an acyl halide, for example, benzoyl chloride or 4-phenylbenzoyl chloride. The resulting compounds may then be separated into the individual racemic mixtures of cis- and trans-enantiomers, which may then be hydrolyzed to the corresponding alcohol by treatment with, e.g., an alkali metal hydroxide in aqueous methanol or dioxane. The resulting alcohols may then be treated with either mesyl chloride or tosyl chloride, as described above, to form the appropriate compounds of formulae (Da) and (Db).

Compounds of formulae (Da) and (Db) are then reacted with a compound of formula (E) optionally in the presence of a base or with a salt of a compound of formula (E) to form the corresponding compounds of formulae (Ia) and (Ib). The metal salt of a compound of formula (E) wherein $X_a$ is sulfur may be prepared, for example, by treating the compound with a suitable base such as an alkali metal carbonate, hydroxide or alkoxide, e.g., potassium carbonate in the presence of a solvent such as acetone or methanol or by using an alkali metal hydride such as sodium hydride in an inert solvent. The salt of a compound of formula (E) wherein $X_a$ is oxygen may be prepared by treating the compound with a base such as an alkali metal hydride such as sodium hydride in the presence of a solvent such as dimethylsulfoxide, dimethylformamide, tetrahydrofuran and the like.

Alternatively, compounds of formulae (Da) and (Db) may be reacted with a compound of formula (E) under phase-transfer conditions, for example, in a mixture of an inert organic solvent such as a chlorinated hydrocarbon (e.g., methylene chloride) and an aqueous base such as an aqueous alkali metal hydroxide (e.g., sodium hydroxide) in the presence of a quaternary phosphonium or ammonium salt such as a tetrabutylammonium salt, to form the corresponding compounds of formulae (Ia) and (Ib).

Alternatively, compounds of formula (Ia) and (Ib) may be prepared by first ketalizing an α-halo ketone of formula (Bc) under similar reaction conditions as described above for preparing compounds of formula (C) above except that only a catalytic amount of acid, e.g., about 0.01 to about 0.2 molar equivalents, is used. The resulting alcohols may then be converted into the halides or sulfonates as described above. The resulting compounds may then be treated with a phenol or thiophenol of formula (E) in the presence of a base, or with a salt thereof, such as an alkali metal salt in an inert organic solvent such as dimethylformamide, dimethylsulfoxide, acetone, methanol, and the like, at a temperature between 20° C. and 120° C. to form compounds of the following formula (G):

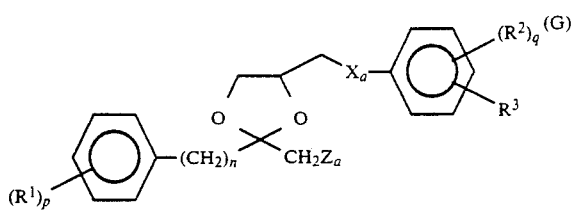

wherein n, p, q, $R^1$, $R^2$ and $R^3$ are as defined above for compounds of formulae (Ia) or (Ib), $X_a$ is oxygen or sulfur, and $Z_a$ is bromo or iodo. These compounds may be separated by conventional methods into the individual racemic mixtures of cis- and trans-enantiomers. These compounds may then be treated with imidazole or a compound of formula (Ba), or a salt thereof, preferably an alkali metal salt, e.g., the sodium salt of imidazole, in an inert organic solvent such as dimethylformamide, dimethylacetamide, and the like, at a temperature between 20° C. and 165° C., optionally in the presence of an alkali metal iodide such as sodium or potassium iodide, to form compounds of formulae (Ia) and (Ib). This alkylation of the imidazole would generally be carried out using from 1 to 5 moles of imidazole and/or 1 to 2 moles of the metal salt relative to one mole of the starting compound.

Compounds of formulae (Ia) and (Ib) wherein $R^3$ is —N($R^5$)$R^6$ where $R^5$ is hydrogen or lower alkyl and $R^6$ is —C(Y)$R^7$ where Y is sulfur and $R^7$ is —N($R^8$)$R^9$ where $R^8$ is hydrogen and $R^9$ is hydrogen, lower alkyl or lower alkoxy carbonyl, e.g., wherein $R^3$ is aminothiocarbonylamino, may be prepared from compounds of formulae (Ia) or (Ib) wherein $R^3$ is amino or lower monoalkylamino by reaction with a lower alkyl or lower alkoxycarbonyl isothiocyanate or with an alkali metal isothiocyanate, preferably in the presence of a base such as triethylamine in a suitable solvent such as, for example, tetrahydrofuran, dioxane, benzene, methylene chloride and the like.

Compounds of formulae (Ia) and (Ib) wherein $R^3$ is —N($R^5$)$R^6$ where $R^5$ is hydrogen or lower alkyl and $R^6$ is —C(Y)$R^7$ where Y is oxygen and $R^7$ is —N($R^8$)$R^9$ where $R^8$ is hydrogen and $R^9$ is hydrogen, lower alkyl or lower alkoxycarbonyl, e.g., wherein $R^3$ is aminocarbonylamino, may be prepared by reacting compounds of formulae (Ia) or (Ib) wherein $R^3$ is amino or lower monoalkylamino with a lower alkyl or lower alkoxycarbonyl isocyanate or with an alkali metal isocyanate, e.g., potassium isocyanate, preferably in the presence of a base such as triethylamine in a suitable solvent such as, for example, tetrahydrofuran, dioxane, benzene, methylene chloride and the like.

The foregoing reaction may be carried out according to art-known methodologies, e.g., by stirring the reactants together, preferably while heating, in an appropriate reaction-inert solvent, e.g., 1,4-dioxane, optionally in the presence of a base such as triethylamine. It may also be appropriate to use an appropriate alkali metal cyanate in aqueous medium, the free acid being liberated by the addition thereto of an appropriate acid, e.g., acetic acid.

Compounds of formulae (Ia) and (Ib) wherein $R^3$ is —N($R^5$)$R^6$ where $R^5$ is hydrogen or lower alkyl and $R^6$ is lower alkylsulfonyl or —C(Y)R$^7$ where Y is sulfur or oxygen and R$^7$ is hydrogen, lower alkyl or lower alkoxy, e.g., where R$^3$ is lower alkylsulfonylamino, can be prepared by acylating or sulfonylating the appropriate amine of formulae (Ia) or (Ib) with an appropriate acylating or sulfonylating agent according to common N-acylating or N-sulfonylating procedures. Suitable acylating or sulfonylating agents which may be used include acyl halides and anhydrides or sulfonyl halides derived from the appropriate corresponding carboxylic, thiocarboxylic or sulfonic acid, including formic-acetic anhydride when formylation is desired. In order to prepare compounds wherein R$^7$ is lower alkoxy, i.e., where R$^3$ is lower alkoxycarbonylamino or lower alkoxy(thiocarbonyl)amino there may be used appropriate carbonohalidates, preferably carbonochloridates, such as methyl chloroformate, or ethoxy(thiocarbonyl)chloride.

Alternatively, compounds of formulae (Ia) and (Ib) wherein Y is sulfur may be prepared from the corresponding compounds where Y is oxygen by treatment with a thiation reagent such as P$_4$S$_{10}$ or Lawesson's reagent (2,4-bis(4-methoxyphenyl)-1,3-dithia-2,4-diphosphetane-2,4-disulfide).

Compounds of formulae (Ia) and (Ib) wherein R$^3$ is —N(R$^5$)R$^6$ where R$^5$ is hydrogen or lower alkyl and R$^6$ is —C(Y)R$^7$ where Y is oxygen or sulfur and R$^7$ is —N(R$^8$)R$^9$ where R$^8$ and R$^9$ are independently lower alkyl may be prepared from compounds wherein R$^3$ is amino or lower monoalkylamino by acylation with a dialkylcarbamoyl halide or dialkylthiocarbamoyl halide in an inert organic solvent such as THF, CH$_2$Cl$_2$ or the like, optionally in the presence of a base such as triethylamine or pyridine.

Alternatively, compounds of formulae (Ia) or (Ib) wherein R$^3$ is —N(R$^5$)R$^6$ where R$^5$ is hydrogen or lower alkyl and R$^6$ is —C(Y)R$^7$ where Y is oxygen or sulfur and R$^7$ is lower alkoxy or —N(R$^8$)R$^9$ where R$^8$ is hydrogen or lower alkyl and R$^9$ is lower alkyl may be prepared from compounds of formulae (Ia) and (Ib) where R$_3$ is amino or lower monoalkylamino which have been treated with phosgene or thiophosgene followed by reaction with a lower dialkylamine, lower alkylamine or alkanol.

Compounds of formulae (Ia) and (Ib) wherein R$^3$ is —N(R$^5$)R$^6$ where R$^5$ and R$^6$ together with N is piperazino wherein the piperazino is substituted at the 4-position by —C(O)R$^{10}$ where R$^{10}$ is hydrogen, lower alkyl, lower alkoxy or amino, may be prepared by the procedures described above from the corresponding unsubstituted piperazino compounds.

Compounds of formulae (Ia) and (Ib) where R$^3$ is amino may also be prepared from the corresponding compounds of formulae (Ia) and (Ib) where R$^3$ is nitro by reduction using a hydrogenation catalyst such as palladium on charcoal and hydrogen gas or any of the reducing agents known in the art, such as zinc in acetic acid, sodium borohydride with transition metal salts, or ferrous salts, etc.

Alternatively, reduction of a nitro compound of formulae (Ia) or (Ib) in the presence of an acid anhydride, e.g., zinc in acetic acid/acetic anhydride, produces compounds of formulae (Ia) or (Ib) wherein R$^3$ is —N(R$^5$)R$^6$ where R$^5$ is hydrogen and R$^6$ is —C(Y)R$^7$ where Y is oxygen and R$^7$ is hydrogen or lower alkyl.

Compounds of formulae (Ia) and (Ib) wherein X$_a$ is sulfur may be further oxidized to form the corresponding sulfinyl and sulfonyl compounds of formula (I). Appropriate oxidizing agents are, for example, alkali metal periodates such as sodium periodate and potassium periodate, and peroxides, such as hydrogen peroxide. Preferably, the oxidizing agent is m-chloroperbenzoic acid.

D. Preparation of Compounds of Formulae (Ic), (Id), (Ie) and (If)

Compounds of formula (Ic), (Id), (Ie) and (If) are individual stereoisomers of compounds of formula (I) wherein n is 2 or 3; p is 0, 1 or 2; q is 0, 1 or 2; X is oxygen or S(O)$_t$ where t is 0; each R$^1$ is independently halo, lower alkyl, lower alkoxy, or trifluoromethyl; each R$^2$ is independently halo or lower alkyl; R$^3$ is nitro or —N(R$^5$)R$^6$ where R$^5$ is hydrogen or lower alkyl; R$^6$ is hydrogen, lower alkyl, lower alkylsulfonyl or —C(Y)R$^7$ where Y is oxygen or sulfur and R$^7$ is hydrogen, lower alkyl, lower alkoxy or —N(R$^8$)R$^9$ where R$^8$ is hydrogen or lower alkyl and R$^9$ is hydrogen, lower alkyl or lower alkoxycarbonyl; or R$^5$ and R$^6$ together with N is pyrrolidino, piperidino, morpholino, thiomorpholino or piperazino wherein the piperazino is optionally substituted at the 4-position by —C(O)R$^{10}$ where R$^{10}$ is hydrogen, lower alkyl, lower alkoxy or amino; and R$^4$ is hydrogen or lower alkyl, or pharmaceutically acceptable salts thereof.

Compounds of formula (Ic) are (2S)-cis-enantiomers; compounds of formula (Id) are (2R)-trans-enantiomers; compounds of formula (Ie) are (2S)-trans-enantiomers; and compounds of formula (If) are (2R)-cis-enantiomers. These compounds are prepared as shown in the following Reaction Schemes 4a and 4b wherein n, p, q, R$^1$, R$^2$, R$^3$ and R$^4$ are as described above, X$_a$ is oxygen or sulfur and R$^{11}$ is a leaving group:

REACTION SCHEME 4a

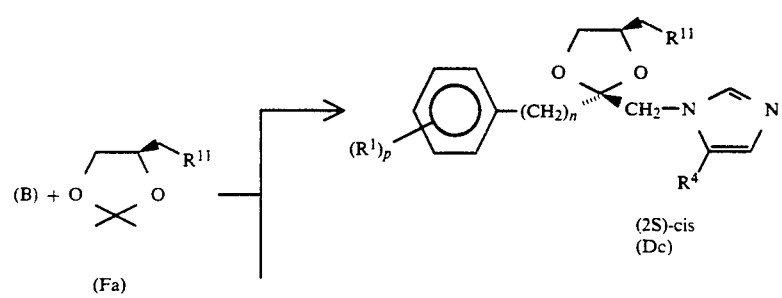

REACTION SCHEME 4a
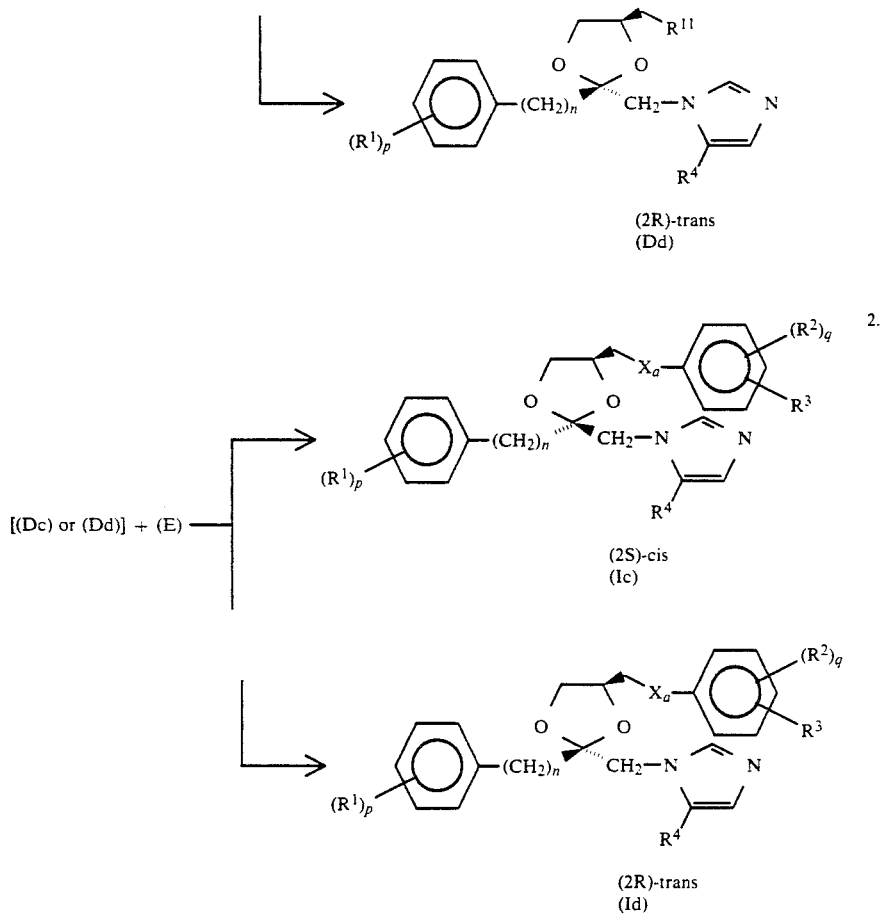
REACTION SCHEME 4b
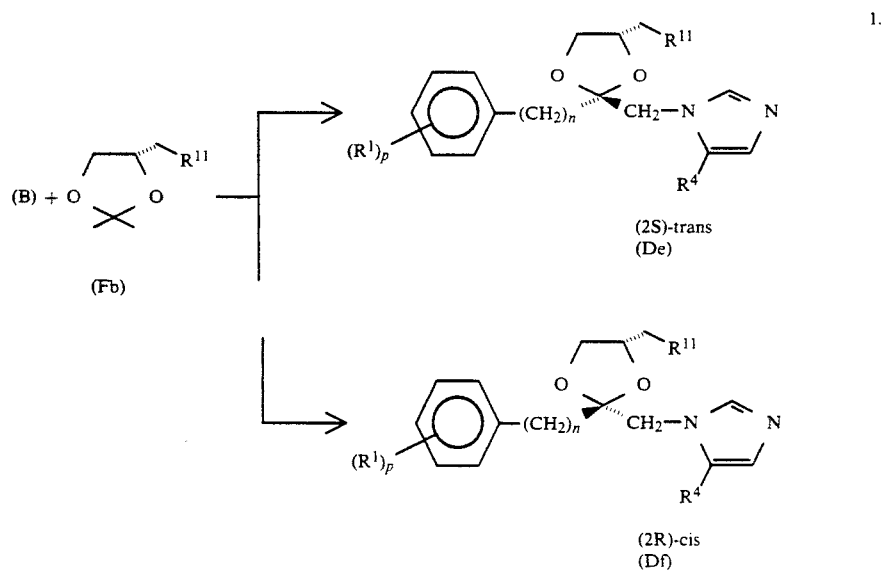

REACTION SCHEME 4b -continued

[(De) or (Df)] + (E) ⟶

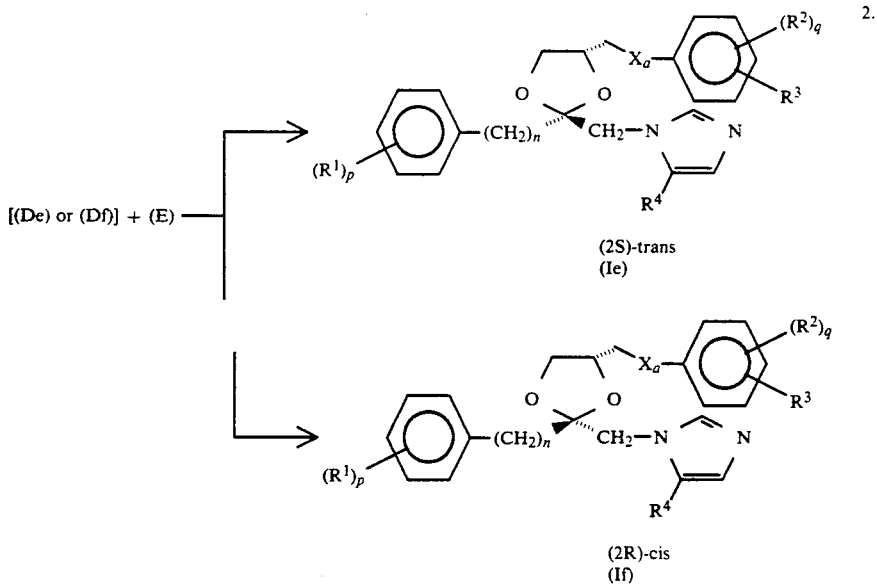

(2S)-trans
(Ie)

(2R)-cis
(If)

Compounds of formula (Fa) and (Fb), for example, S-solketal tosylate and R-solketal tosylate, respectively, are commercially available, for example, from Aldrich Chemical Co., Fluka, or International Bio-Synthetics (IBIS), or may be prepared according to methods known to those of ordinary skill in the art. Compounds of formula (B) are prepared above in Sections B and C.

As demonstrated in the foregoing Reaction Scheme 4a, compounds of formulae (Ic) and (Id) are prepared by first treating compounds of formula (B) with compounds of formula (Fa). This reaction is generally carried out under anhydrous conditions and using from 1 to 10 moles, preferably from about 1 to about 5 moles of the compound of formula (Fa) relative to one mole of the compound of formula (B). The reaction begins with the slow addition of an anhydrous mixture of a compound of formula (Fa) and a simple alcohol, for example, methanol, ethanol or n-butanol, in an inert solvent, for example, benzene or toluene, to a anhydrous mixture of a compound of formula (B) and an organic acid, for example, p-toluenesulfonic acid, in an inert solvent. The resulting reaction mixture is allowed to reflux with azeotropic water removal for about 6 to 10 hours, preferably for about 6 to 7 hours. The resulting crude product is then subjected to conventional separation techniques in order to yield the (2S)-cis-diastereomer of formula (Dc) and the (2R)-trans-diastereomer of formula (Dd). Preferably such separation techniques include flash and column chromatography.

Alternatively, as demonstrated in Reaction Scheme 4b, compounds of formula (B) are similarly treated with compounds of formula (Fb), for example, R-solketal tosylate, to yield the (2S)-trans-diastereomer of formula (De) and the (2R)-cis-diastereomer of formula (Df).

Alternatively, compounds of formula (B) may be treated with a chiral diol of the formula $CH_2(OH)CH(OH)CH_2R^{11}$ where $R^{11}$ is a leaving group under similar conditions as those described above for treatment with compounds of formulae (Fa) and (Fb), e.g., anhydrous acidic conditions, to yield the corresponding diastereomers of formulae (Dc), (Dd), (De) and (Df). Chiral diols of the above formula may be prepared according to the methods described in J. Org. Chem. (1978), Vol. 43, p. 4876, or by methods known to one of ordinary skill in the art.

Compounds of formula (Dd) may be reequilibrated in the presence of an anhydrous organic acid, for example, p-toluenesulfonic acid, to yield a mixture of compounds of formulae (Dc) and (Dd). For example, the reaction may be conveniently carried out in a higher-boiling solvent, for example, xylenes, and the presence of a higher boiling alkanol, for example, n-heptanol. Similarly, compounds of formula (Dc) may be reequilibrated to yield a mixture of compounds of formulae (Dd) and (Dc); compounds of formula (De) may be reequilibrated to yield a mixture of compounds of formulae (Df) and (De); and compounds of formulae (Df) may be reequilibrated to yield a mixture of compounds of formulae (De) and (Df).

In a similar manner as described above in Section C for the preparation of compounds of formulae (Ia) and (Ib), compounds of formulae (Dc), (Dd), (De) and (Df) are then treated with a compound of formula (E) to yield the corresponding compounds of formulae (Ic), (Id), (Ie) and (If).

Alternatively, in a similar manner as described above for compounds of formulae (Ia) and (Ib), compounds of formulae (Ic), (Id), (Ie) and (If) may be prepared by first ketalizing an α-halo ketone of formula (Bc) with compounds of formulae (Fa) or (Fb). The resulting halides or sulfonates may then be treated with a compound of formula (E) to form the corresponding phenoxy and phenylthio compounds, which may be separated by conventional methods into the individual enantiomers. The individual enantiomers may then be treated with imidazole or an imidazole of formula (Ba) to form the corresponding compounds of formulae (Ic), (Id), (Ie) or (If).

Alternatively, compounds of formula (B) may be treated with either a compound of formula (Fa) or a compound of formula (Fb), under similar conditions as described above, to form compounds of formula (D), which can then be treated with compounds of formula (E) to form the corresponding diastereomeric mixtures of the individual enantiomers. The diastereomers may then be separated from each other by conventional diastereomeric separation methods to yield the corresponding compounds of formulae (Ic), (Id), (Ie) or (If).

Compounds of formulae (Ic), (Id), (Ie) and (If) wherein $X_a$ is sulfur may be further oxidized as described above for compounds of formulae (Ia) and (Ib) to form the corresponding sulfinyl and sulfonyl compounds of formula (I).

Compounds of formulae (Ic), (Id), (Ie) and (If) wherein $R^3$ is —$N(R^5)R^6$ where $R^5$ is hydrogen or lower alkyl and $R^6$ is hydrogen may be further treated as described above for compounds of formulae (Ia) and (Ib) to form compounds of formulae (Ic), (Id), (Ie) and (If) wherein $R^6$ is lower alkylsulfonyl or —$C(Y)R^7$ where Y is oxygen or sulfur and $R^7$ is hydrogen, lower alkyl, lower alkoxy or —$N(R^8)R^9$ where $R^8$ is hydrogen or lower alkyl and $R^9$ is hydrogen, lower alkyl or lower alkoxycarbonyl, or compounds of formulae (Ic), (Id), (Ie) and (If) wherein $R^5$ and $R^6$ together with N is piperazino unsubstituted at the 4-position, which may be converted as described above to form compounds of formulae (Ic), (Id), (Ie) and (If) wherein the piperazino is substituted at the 4-position by —$C(O)R^{10}$ where $R^{10}$ is hydrogen, lower alkyl, lower alkoxy or amino.

In summary, compounds of formula (I), which are compounds of formulae (Ia), (Ib), (Ic), (Id), (Ie) and (If), are prepared by:

(1) reacting a compound of formula (D) wherein n is 2 or 3; p is 0, 1 or 2; $R^4$ is hydrogen or lower alkyl; and $R^{11}$ is a leaving group; with a compound of formula (E) wherein $X_a$ is oxygen or sulfur; q is 0, 1 or 2; each $R^2$ is independently halo or lower alkyl; $R^3$ is nitro or —$N(R^5)R^6$ where $R^5$ is hydrogen or lower alkyl; $R^6$ is hydrogen, lower alkyl, lower alkylsulfonyl or —$C(Y)R^7$ where Y is oxygen or sulfur and $R^7$ is hydrogen, lower alkyl, lower alkoxy or —$N(R^8)R^9$ where $R^8$ is hydrogen or lower alkyl and $R^9$ is hydrogen, lower alkyl or lower alkoxycarbonyl; or $R^5$ and $R^6$ together with N is pyrrolidino, piperidino, morpholino, thiomorpholino or piperazino wherein the piperazino is optionally substituted at the 4-position by —$C(O)R^{10}$ where $R^{10}$ is hydrogen, lower alkyl, lower alkoxy or amino, to form compounds of formula (I) wherein X is oxygen or $S(O)_t$ where t is 0; and n, p, q, $R^1$, $R^2$, $R^3$ and $R^4$ are as defined above; or (2) reacting imidazole or an imidazole of formula (Ba) wherein $R^4$ is lower alkyl with a compound of formula (G) where $Z_a$ is bromo or iodo; $X_a$ is oxygen or sulfur; and n, p, q, $R^1$, $R^2$ and $R^3$ are as defined above, to form compounds of formula (I) where X is oxygen or $S(O)_t$ where t is 0, and n, p, q, $R^1$, $R^2$, $R^3$ and $R^4$ are as defined above; or (3) oxidizing a compound of formula (I) wherein n, p, q, $R^1$, $R^2$, $R^3$ and $R^4$ are as defined above, and X is —$S(O)_t$ where t is 0 with a suitable oxidizing agent to form a compound of formula (I) wherein X is —$S(O)_t$ where t is 1 or 2; or (4) treating a compound of formula (I) wherein n, p, q, $R^1$, $R^2$ and $R^4$ are as defined above, X is oxygen or $S(O)_t$ where t is 0, 1 or 2; and $R^3$ is amino or lower monoalkylamino, with an isothiocyanate to form a compound of formula (I) wherein n, p, q, X, $R^1$, $R^2$, and $R^4$ are as defined above and $R^3$ is —$N(R^5)R^6$ where $R^5$ is hydrogen or lower alkyl, and $R^6$ is —$C(Y)R^7$ where Y is sulfur and $R^7$ is —$N(R^8)R^9$ where $R^8$ is hydrogen and $R^9$ is hydrogen, lower alkyl or lower alkoxycarbonyl; or (5) treating a compound of formula (I) wherein n, p, q, X, $R^1$, $R^2$ and $R^4$ are as defined above, and $R^3$ is amino or lower monoalkylamino, with a lower alkyl or lower alkoxycarbonyl isocyanate or with an alkali metal isocyanate, to form a compound of formula (I) wherein n, p, q, X, $R^1$, $R^2$, and $R^4$ are as defined above and $R^3$ is —$N(R^5)R^6$ where $R^5$ is hydrogen or lower alkyl and $R^6$ is —$C(Y)R^7$ where Y is oxygen and $R^7$ is —$N(R^8)R^9$ where $R^8$ is hydrogen and $R^9$ is hydrogen, lower alkyl or lower alkoxycarbonyl; or (6) treating a compound of formula (I) wherein n, p, q, X, $R^1$, $R^2$ and $R^4$ are as defined above, and $R^3$ is amino or lower monoalkylamino with an acylating or sulfonylating agent to form a compound of formula (I) wherein n, p, q, X, $R^1$, $R^2$, and $R^4$ are as defined above and $R^3$ is —$N(R^5)R^6$ where $R^5$ is hydrogen or lower alkyl and $R^6$ is lower alkylsulfonyl or —$C(Y)R^7$ where Y is sulfur or oxygen and $R^7$ is hydrogen, lower alkyl, lower alkoxy or —$N(R^8)R^9$ where $R^8$ and $R^9$ are independently lower alkyl; or (7) treating a compound of formula (I), wherein n, p, q, X, $R^1$, $R^2$ and $R^4$ are as defined above, and $R^3$ is amino or lower monoalkylamino, which has been treated with phosgene or thiophosgene, with a lower dialkylamino, lower alkylamino or alkanol, to form a compound of formula (I) wherein n, p, q, X, $R^1$, $R^2$ and $R^4$ are as defined above, and $R^3$ is —$N(R^5)R^6$ where $R^5$ is hydrogen or lower alkyl, and $R^6$ is —$C(Y)R^7$ where Y is oxygen or sulfur and $R^7$ is lower alkoxy or —$N(R^8)R^9$ where $R^8$ is hydrogen or lower alkyl and $R^9$ is lower alkyl; or (8) treating a compound of formula (I) wherein n, p, q, X, $R^1$, $R^2$ and $R^4$ are as defined above for compounds of formula (I), and $R^3$ is —$N(R^5)R^6$ where $R^5$ and $R^6$ together with N is piperazino unsubstituted at the 4-position, with an acylating agent, isocyanate or isocyanic acid to form a compound of formula (I) wherein n, p, q, X, $R^1$, $R^2$ and $R^4$ are as defined above and the piperazino is substituted at the 4-position by —$C(O)R^{10}$ where $R^{10}$ is hydrogen, lower alkyl, lower alkoxy or amino; or (9) reducing a compound of formula (I) wherein n, p, q, X, $R^1$, $R^2$ and $R^4$ are as defined above, and $R^3$ is nitro with a suitable reducing agent to form a compound of formula (I) wherein n, p, q, X, $R^1$, $R^2$ and $R^4$ are as defined above, and $R^3$ is —$N(R^5)R^6$ where $R^5$ is hydrogen and $R^6$ is hydrogen or —$C(Y)R^7$ where Y is oxygen and $R^7$ is hydrogen or lower alkyl; or

(10) treating a compound of formula (I) wherein n, p, q, X, $R^1$, $R^2$, $R^3$ and $R^4$ are as defined above, except that Y is oxygen, with a thiation reagent to form a compound of formula (I) wherein n, p, q, X, $R^1$, $R^2$, $R^3$ and $R^4$ are as defined above, except that Y is sulfur.

In addition, all compounds of formula (I) that exist in free base form may be converted to their pharmaceutically acceptable salts by treatment with the appropriate inorganic or organic acid. Salts of compounds of formula (I) can also be converted to the free base form or to another salt.

The following specific preparations and examples are provided as a guide to assist in the practice of the invention, and are not intended as a limitation on the scope of the invention.

PREPARATION 1

Compounds of Formula (Ab)

A. A stirred solution of 4-chlorophenethyl alcohol (131 g) and triphenylphosphine (241.3 g) in dry THF (500 mL) at 0° C. was treated portionwise over 30 min. with N-bromosuccinimide (163.75 g). The resulting black solution was stirred overnight at room temperature, whereupon the THF was evaporated and the residue stirred with ether. The solution was filtered to remove triphenylphosphine oxide and the filtrate evaporated and treated with hexane. The stirred mixture was filtered, evaporated, and the residue distilled under reduced pressure to give 100 g of 4-chlorophenethyl bromide as a colorless liquid, b.p. 85° C. (3 mm Hg).

B. In a similar manner, but replacing 4-chlorophenethyl alcohol with other appropriately substituted primary alcohols, the following compounds are made:
4-fluorophenethyl bromide;
4-methoxyphenethyl bromide;
4-methylphenethyl bromide;
2,4-dichlorophenethyl bromide;
4-ethoxyphenethyl bromide;
4-ethylphenethyl bromide; and
4-trifluoromethylphenethyl bromide.

PREPARATION 2

Compounds of Formula (Ad)

A. To a flame-dried flask containing 7.75 g of magnesium turnings under ether was added 4-chlorophenethyl bromide (70 g) in anhydrous ether (250 mL) at such a rate as to maintain a gentle reflux. When the addition was complete, the mixture was heated under reflux for an additional hour and then treated dropwise over one hour with allyl bromide (27.6 mL, 38.6 g) in ether (75 mL) maintaining a gentle reflux. The resulting mixture was stirred overnight at room temperature and then poured onto 600 mL of ice-cold dilute sulfuric acid. The product was extracted with ethyl acetate and the combined extracts were washed with dilute aqueous potassium carbonate, dried (MgSO$_4$) and evaporated. The resulting brown oil was distilled under reduced pressure to give 43 g of 5-(4-chlorophenyl)pent-1-ene, b.p. 74°–80° (2 mmHg) as a colorless liquid.

B. In a similar manner, but replacing 4-chlorophenethyl bromide with other appropriately substituted compounds of formula (Ab), the following compounds of formula (Ad) are prepared:
5-(4-fluorophenyl)pent-1-ene;
5-(4-methoxyphenyl)pent-1-ene;
5-(4-methylphenyl)pent-1-ene;
5-(2,4-dichlorophenyl)pent-1-ene;
5-(2,4-diethylphenyl)pent-1-ene;
5-(3,5-di-n-propoxyphenyl)pent-1-ene;
5-(4-ethoxyphenyl)pent-1-ene;
5-(4-ethylphenyl)pent-1-ene;
5-(4-trifluoromethylphenyl)pent-1-ene;
4-(4-chlorophenyl)but-1-ene;
4-(4-fluorophenyl)but-1-ene;
4-(4-methoxyphenyl)but-1-ene;
4-(4-methylphenyl)but-1-ene;
4-(2,4-dichlorophenyl)but-1-ene;
4-(2,4-diethylphenyl)but-1-ene;
4-(3,5-di-n-propoxyphenyl)but-1-ene;
4-(4-ethoxyphenyl)but-1-ene;
4-(4-ethylphenyl)but-1-ene; and
4-(4-trifluoromethylphenyl)but-1-ene.

PREPARATION 3

Compounds of Formula (Ae)

A. To a solution of 5-(4-chlorophenyl)pent-1-ene (43.2 g) in dichloromethane (400 mL) was added dropwise with stirring a mixture of 40% peracetic acid (200 mL) and sodium acetate (6.5 g). The resulting mixture was heated under reflux for 2 hours, cooled, and stirred with water (400 mL). The dichloromethane layer was separated, washed with dilute aqueous potassium carbonate until neutral, water, and dried (MgSO$_4$) and evaporated to give 46.7 g of 5-(4-chlorophenyl)-1,2-epoxypentane as a colorless oil.

B. In a similar manner, but replacing 5-(4-chlorophenyl)pent-1-ene with other appropriately substituted compounds of formula (Ad), the following compounds of formula (Ae) are prepared:
5-(4-fluorophenyl)-1,2-epoxypentane;
5-(4-methoxyphenyl)-1,2-epoxypentane;
5-(4-methylphenyl)-1,2-epoxypentane;
5-(2,4-dichlorophenyl)-1,2-epoxypentane;
5-(2,4-diethylphenyl)-1,2-epoxypentane;
5-(3,5-di-n-propoxyphenyl)-1,2-epoxypentane;
5-(4-ethoxyphenyl)-1,2-epoxypentane;
5-(4-ethylphenyl)-1,2-epoxypentane;
5-(4-trifluoromethylphenyl)-1,2-epoxypentane;
4-(4-chlorophenyl)-1,2-epoxybutane;
4-(4-fluorophenyl)-1,2-epoxybutane;
4-(4-methoxyphenyl)-1,2-epoxybutane;
4-(4-methylphenyl)-1,2-epoxybutane;
4-(2,4-dichlorophenyl)-1,2-epoxybutane;
4-(2,4-diethylphenyl)-1,2-epoxybutane;
4-(3,5-di-n-propoxyphenyl)-1,2-epoxybutane;
4-(4-ethoxyphenyl)-1,2-epoxybutane;
4-(4-ethylphenyl)-1,2-epoxybutane; and
4-(4-trifluoromethylphenyl)-1,2-epoxybutane.

PREPARATION 4

Compounds of Formula (A) wherein n is 2 or 3 and $R^4$ is hydrogen

A. To a suspension of sodium hydride (13.44 g of a 50% dispersion in mineral oil) in dry DMF (50 mL) under nitrogen was added imidazole (20.62 g) in dry DMF (50 mL) with stirring at such a rate as to keep the temperature below 65° C. (ice bath). When the evolution of gas had ceased, 5-(4-chlorophenyl)-1,2-epoxypentane was added dropwise and the mixture stirred overnight at room temperature. The resulting brown solution was added to 2.5 L of water, extracted with ethyl acetate (3×400 mL) and the combined extracts were washed with water three times, dried (MgSO$_4$) and evaporated to give an orange oil (52 g) which crystallized. Washing the solid with ether and filtration give 37.2 g of 1-(5-(4-chlorophenyl)-2-hydroxypentyl)imidazole, m.p. 84°–85° C.

B. In a similar manner, but replacing 5-(4-chlorophenyl)-1,2-epoxypentane with other appropriately substituted compounds of formula (Ae), the following compounds of formula (A) where n is 3 are prepared:
1-(5-(4-methoxyphenyl)-2-hydroxypentyl)imidazole;
1-(5-(4-fluorophenyl)-2-hydroxypentyl)imidazole;
1-(5-(4-methylphenyl)-2-hydroxypentyl)imidazole;
1-(5-(2,4-dichlorophenyl)-2-hydroxypentyl)imidazole;
1-(5-(2,4-dimethylphenyl)-2-hydroxypentyl)imidazole;
1-(5-(3,5-di-n-propoxyphenyl)-2-hydroxypentyl)imidazole;
1-(5-(3,5-difluorophenyl)-2-hydroxypentyl)imidazole;

1-(5-(4-ethoxyphenyl)-2-hydroxypentyl)imidazole;
1-(5-(4-trifluoromethylphenyl)-2-hydroxypentyl)imidazole;
1-(4-(4-methoxyphenyl)-2-hydroxybutyl)imidazole;
1-(4-(4-chlorophenyl)-2-hydroxybutyl)imidazole;
1-(4-(4-fluorophenyl)-2-hydroxybutyl)imidazole;
1-(4-(4-methylphenyl)-2-hydroxybutyl)imidazole;
1-(4-(2,4-dichlorophenyl)-2-hydroxybutyl)imidazole;
1-(4-(2,4-dimethylphenyl)-2-hydroxybutyl)imidazole;
1-(4-(3,5-di-n-propoxyphenyl)-2-hydroxybutyl)imidazole;
1-(4-(3,5-difluorophenyl)-2-hydroxybutyl)imidazole;
1-(4-(4-ethoxyphenyl)-2-hydroxybutyl)imidazole; and
1-(4-(4-trifluoromethylphenyl)-2-hydroxybutyl)imidazole.

PREPARATION 5

4-methyl-1-tritylimidazole

A. A stirred mixture of 4(5)-methylimidazole (9.00 g) in dry DMF (30 mL) at 0° C. was treated portionwise with solid trityl chloride (5.6 g). After stirring overnight, the product was filtered off, washed with a little DMF, followed by acetonitrile and dried to give an electrostatic white solid (5.00 g). Recrystallization from methylene chloride/acetone gave 4.28 g of the title compound, 4-methyl-1-tritylimidazole, m.p. 218°-220° C.

B. In a similar manner, but replacing 4(5)-methylimidazole with other appropriately substituted imidazoles, the following compounds are made:
4-ethyl-1-tritylimidazole;
4-n-propyl-1-tritylimidazole;
4-n-butyl-1-tritylimidazole; and
4-(1-methylethyl)-1-tritylimidazole.

PREPARATION 6

Compounds of Formula (B) where $R^4$ is lower alkyl

A. A mixture of 4-methyl-1-tritylimidazole (12.9 g, 39.8 mmol) and 1-bromo-4-(4-chlorophenyl)butan-2-one (12.5 g, 47.8 mmol, 1.2 equivalents) in CH$_3$CN (~200 mL) was heated at reflux for 16 hours. The reaction mixture was then cooled to room temperature and 2N HCL (30 mL) was added. The reaction mixture was then heated at reflux for 30 minutes, cooled to room temperature and treated with water (~500 mL). The resulting mixture was then washed with ether (~1×100 mL) and the pH adjusted to between 9 and 10 with 2N NaOH. The aqueous layer was extracted with ethyl acetate (3×100 mL), and the combined extracts were then washed with brine and dried over Na$_2$SO$_4$. After filtration and concentration, the resulting crude product (8.5 g) was purified by silica gel chromotography, eluting with 1-8% methanol in methylene chloride to give 8.2 g of 4-(4-chlorophenyl)-1-(5-methylimidazol-1-yl)butan-2-one (70% yield). The hydrochloride salt was recrystallized from methanol/ethyl acetate with m.p. 227°-228° C.

B. In a similar manner, but replacing 4-methyl-1-tritylimidazole with other appropriately 4-lower-alkyl-substituted imidazoles, and 1-bromo-4-(4-chlorophenyl)butan-2-one with other appropriately substituted α-haloketones, the following compounds are made:
4-(4-chlorophenyl)-1-(5-ethylimidazol-1-yl)butan-2-one;
4-(4-chlorophenyl)-1-(5-n-butylimidazol-1-yl)butan-2-one;
4-(4-chlorophenyl)-1-(5-n-propylimidazol-1-yl)butan-2-one;
4-(4-methoxyphenyl)-1-(5-ethylimidazol-1-yl)butan-2-one;
4-(4-methoxyphenyl)-1-(5-n-butylimidazol-1-yl)butan-2-one;
4-(4-methoxyphenyl)-1-(5-n-propylimidazol-1-yl)butan-2-one;
4-(4-methylphenyl)-1-(5-ethylimidazol-1-yl)butan-2-one;
4-(4-methylphenyl)-1-(5-n-butylimidazol-1-yl)butan-2-one;
4-(4-methylphenyl)-1-(5-n-propylimidazol-1-yl)butan-2-one;
5-(4-chlorophenyl)-1-(5-ethylimidazol-1-yl)pentan-2-one;
5-(4-chlorophenyl)-1-(5-n-butylimidazol-1-yl)pentan-2-one;
5-(4-chlorophenyl)-1-(5-n-propylimidazol-1-yl)pentan-2-one;
5-(4-methoxyphenyl)-1-(5-ethylimidazol-1-yl)pentan-2-one;
5-(4-methoxyphenyl)-1-(5-n-butylimidazol-1-yl)pentan-2-one;
5-(4-methoxyphenyl)-1-(5-n-propylimidazol-1-yl)pentan-2-one;
5-(4-methylphenyl)-1-(5-ethylimidazol-1-yl)pentan-2-one;
5-(4-methylphenyl)-1-(5-n-butylimidazol-1-yl)pentan-2-one;
5-(4-methylphenyl)-1-(5-n-propylimidazol-1-yl)pentan-2-one;
4-(2,4-dichlorophenyl)-1-(5-ethylimidazol-1-yl)butan-2-one;
4-(2,4-dichlorophenyl)-1-(5-n-butylimidazol-1-yl)butan-2-one; and
4-(2,4-dichlorophenyl)-1-(5-n-propylimidazol-1-yl)butan-2-one.

PREPARATION 7

Compounds of Formula (B) where $R^4$ is hydrogen

A. A solution of oxalyl chloride (74.8 g) in dry dichloromethane (1350 mL) at below −70° C. under a nitrogen atmosphere was treated with dry dimethyl sulfoxide (91.5 mL) in methylene chloride (270 mL) dropwise over 15 to 20 minutes while maintaining the temperature of the reaction mixture below −50° C. After an additional 5 minutes a solution of (±)-1-(4-(4-chlorophenyl)-2-hydroxybutyl)imidazole (128.3 g) in a mixture of dimethyl sulfoxide (50 mL) and methylene chloride (200 mL) was added over a period of 20 minutes keeping the reaction mixture at temperatures below −65° C. After a further 15 minutes dry triethylamine (300 mL) was added rapidly and after 15 minutes the reaction mixture was allowed to warm to 0° C. Water (20 mL) was then added to the reaction mixture, the methylene chloride then removed by evaporation and the resulting slurry was then treated with water and filtered. The filter cake was washed well with ice-water, cold ethyl acetate and then dried in air to yield 118.0 g of 4-(4-chlorophenyl)-1-(imidazol-1-yl)butan-2-one. The hydrochloride salt crystallized from methanol/acetone had a melting point of 172.5°-174.0° C.

B. In a similar manner, but replacing (±)-1-(4-(4-chlorophenyl)-2-hydroxybutyl)imidazole with other appropriately substituted compounds of formula (A), the following compounds of formula (B) were made:

4-phenyl-1-(imidazol-1-yl)butan-2-one;
4-(4-methoxyphenyl)-1-(imidazol-1-yl)butan-2-one;
4-(2,4-dichlorophenyl)-1-(imidazol-1-yl)butan-2-one;
4-(4-methylphenyl)-1-(imidazol-1-yl)butan-2-one; and
4-(4-fluorophenyl)-1-(imidazol-1-yl)butan-2-one.

C. In a similar manner the following compounds of formula (B) are made:
4-(4-ethoxyphenyl)-1-(imidazol-1-yl)butan-2-one;
4-(3,5-dichlorophenyl)-1-(imidazol-1-yl)butan-2-one;
4-(3,5-di-n-propoxy)-1-(imidazol-1-yl)butan-2-one;
4-(4-ethylphenyl)-1-(imidazol-1-yl)butan-2-one;
4-(4-trifluoromethylphenyl)-1-(imidazol-1-yl)butan-2-one;
5-phenyl-1-(imidazol-1-yl)pentan-2-one;
5-(4-methoxyphenyl)-1-(imidazol-1-yl)pentan-2-one;
5-(2,4-dichlorophenyl)-1-(imidazol-1-yl)pentan-2-one;
5-(4-methylphenyl)-1-(imidazol-1-yl)pentan-2-one;
5-(4-fluorophenyl)-1-(imidazol-1-yl)pentan-2-one;
5-(4-chlorophenyl)-1-(imidazol-1-yl)pentan-2-one;
5-(4-ethoxyphenyl)-1-(imidazol-1-yl)pentan-2-one;
5-(3,5-dichlorophenyl)-1-(imidazol-1-yl)pentan-2-one;
5-(3,5-di-n-propoxy)-1-(imidazol-1-yl)pentan-2-one;
5(4-ethylphenyl)-1-(imidazol-1-yl)pentan-2-one; and
5-(4-trifluoromethylphenyl)-1-(imidazol-1-yl)pentan-2-one.

PREPARATION 8

Compounds of Formula (C)

A. A mixture of 4-(4-chlorophenyl)-1-(imidazol-1-yl)butan-2-one (50 g), p-toluenesulfonic acid monohydrate (42.07 g) and glycerol (37 g) in toluene (200 mL) was heated under reflux, with stirring, through a Dean-Stark trap for 6 hours. The two layers were allowed to separate and the hot toluene (upper layer) decanted and discarded. The lower layer was poured into 2N sodium hydroxide (500 mL), the transfer completed by washing the flask with 1N sodium hydroxide and methylene chloride, and the product extracted with methylene chloride (4×200 mL). The extracts were dried (MgSO$_4$), evaporated and the residue recrystallized from toluene to give 61.4 g of (cis/trans)-2-(2-(4-chlorophenyl)ethyl)-2-(imidazol-1-yl)methyl-4-hydroxymethyl-1,3-dioxolane, m.p. 96°–110° C.

B. In a similar manner, but replacing 4-(4-chlorophenyl)-1-(imidazol-1-yl)butan-2-one with the appropriately substituted compound of formula (B), the following compounds of formula (C) were prepared:
(cis/trans)-2-(2-(4-methoxyphenyl)ethyl)-2-(imidazol-1-yl)methyl-4-hydroxymethyl-1,3-dioxolane;
(cis/trans)-2-(2-(4-fluorophenyl)ethyl)-2-(imidazol-1-yl)methyl-4-hydroxymethyl-1,3-dioxolane;
(cis/trans)-2-(2-phenylethyl)-2-(imidazol-1-yl)methyl-4-hydroxymethyl-1,3-dioxolane;
(cis/trans)-2-(2-(2,4-dichlorophenyl)ethyl)-2-(imidazol-1-yl)methyl-4-hydroxymethyl-1,3-dioxolane; and
(cis/trans)-2-(2-(4-chlorophenyl)ethyl)-2-(5-methylimidazol-1-yl)methyl-4-hydroxymethyl-1,3-dioxolane.

C. In a similar manner, the following compounds of formula (C) are prepared:
(cis/trans)-2-(2-(4-methylphenyl)ethyl)-2-(imidazol-1-yl)methyl-4-hydroxymethyl-1,3-dioxolane;
(cis/trans)-2-(2-(4-ethylphenyl)ethyl)-2-(imidazol-1-yl)methyl-4-hydroxymethyl-1,3-dioxolane;
(cis-trans)-2-(2-(3,5-dichlorophenyl)ethyl)-2-(imidazol-1-yl)methyl-4-hydroxymethyl-1,3-dioxolane;
(cis/trans)-2-(2-(3,5-dimethylphenyl)ethyl)-2-(imidazol-1-yl)methyl-4-hydroxymethyl-1,3-dioxolane;
(cis/trans)-2-(2-(4-ethoxyphenyl)ethyl)-2-(imidazol-1-yl)methyl-4-hydroxymethyl-1,3-dioxolane;
(cis/trans)-2-(2-(trifluoromethylphenyl)ethyl)-2-(imidazol-1-yl)methyl-4-hydroxymethyl-1,3-dioxolane;
(cis/trans)-2-(2-(4-chlorophenyl)ethyl)-2-(5-ethylimidazol-1-yl)-4-hydroxymethyl-1,3-dioxolane;
(cis/trans)-2-(2-(4-chlorophenyl)ethyl)-2-(5-n-butylimidazol-1-yl)-4-hydroxymethyl-1,3-dioxolane;
(cis/trans)-2-(2-(4-chlorophenyl)ethyl)-2-(5-n-propylimidazol-1-yl)-4-hydroxymethyl-1,3-dioxolane;
(cis/trans)-2-(2-(4-methoxyphenyl)ethyl)-2-(5-ethylimidazol-1-yl)-4-hydroxymethyl-1,3-dioxolane;
(cis/trans)-2-(2-(4-methoxyphenyl)ethyl)-2-(5-n-butylimidazol-1-yl)-4-hydroxymethyl-1,3-dioxolane;
(cis/trans)-2-(2-(4-methoxyphenyl)ethyl)-2-(5-n-propylimidazol-1-yl)-4-hydroxymethyl-1,3-dioxolane;
(cis/trans)-2-(2-(4-methylphenyl)ethyl)-2-(5-ethylimidazol-1-yl)-4-hydroxymethyl-1,3-dioxolane;
(cis/trans)-2-(2-(4-methylphenyl)ethyl)-2-(5-n-butylimidazol-1-yl)-4-hydroxymethyl-1,3-dioxolane;
(cis/trans)-2-(2-(4-methylphenyl)ethyl)-2-(5-n-propylimidazol-1-yl)-4-hydroxymethyl-1,3-dioxolane;
(cis/trans)-2-(3-(4-chlorophenyl)propyl)-2-(imidazol-1-yl)methyl-4-hydroxymethyl-1,3-dioxolane;
(cis/trans)-2-(3-(4-methoxyphenyl)propyl)-2-(imidazol-1-yl)methyl-4-hydroxymethyl-1,3-dioxolane;
(cis/trans)-2-(3-(4-fluorophenyl)propyl)-2-(imidazol-1-yl)methyl-4-hydroxymethyl-1,3-dioxolane;
(cis/trans)-2-(3-phenylpropyl)-2-(imidazol-1-yl)methyl-4-hydroxymethyl-1,3-dioxolane;
(cis/trans)-2-(3-(2,4-dichlorophenyl)propyl)-2-(imidazol-1-yl)methyl-4-hydroxymethyl-1,3-dioxolane;
(cis/trans)-2-(3-(4-chlorophenyl)propyl)-2-(5-methylimidazol-1-yl)methyl-4-hydroxymethyl-1,3-dioxolane;
(cis/trans)-2-(3-(4-methylphenyl)propyl)-2-(imidazol-1-yl)methyl-4-hydroxymethyl-1,3-dioxolane;
(cis/trans)-2-(3-(4-ethylphenyl)propyl)-2-(imidazol-1-yl)methyl-4-hydroxymethyl-1,3-dioxolane;
(cis/trans)-2-(3-(3,5-dichlorophenyl)propyl)-2-(imidazol-1-yl)methyl-4-hydroxymethyl-1,3-dioxolane;
(cis/trans)-2-(3-(3,5-dimethylphenyl)propyl)-2-(imidazol-1-yl)methyl-4-hydroxymethyl-1,3-dioxolane;
(cis/trans)-2-(3-(4-ethoxyphenyl)propyl)-2-(imidazol-1-yl)methyl-4-hydroxymethyl-1,3-dioxolane;
(cis/trans)-2-(3-(trifluoromethylphenyl)propyl)-2-(imidazol-1-yl)methyl-4-hydroxymethyl-1,3-dioxolane;
(cis/trans)-2-(3-(4-chlorophenyl)propyl)-2-(5-ethylimidazol-1-yl)-4-hydroxymethyl-1,3-dioxolane;
(cis/trans)-2-(3-(4-chlorophenyl)propyl)-2-(5-n-butylimidazol-1-yl)-4-hydroxymethyl-1,3-dioxolane;
(cis/trans)-2-(3-(4-chlorophenyl)propyl)-2-(5-n-propylimidazol-1-yl)-4-hydroxymethyl-1,3-dioxolane;
(cis/trans)-2-(3-(4-methoxyphenyl)propyl)-2-(5-ethylimidazol-1-yl)-4-hydroxymethyl-1,3-dioxolane;
(cis/trans)-2-(3-(4-methoxyphenyl)propyl)-2-(5-n-butylimidazol-1-yl)-4-hydroxymethyl-1,3-dioxolane;

(cis/trans)-2-(3-(4-methoxyphenyl)propyl)-2-(5-n-propylimidazol-1-yl)-4-hydroxymethyl-1,3-dioxolane;

(cis/trans)-2-(3-(4-methylphenyl)propyl)-2-(5-ethylimidazol-1-yl)-4-hydroxymethyl-1,3-dioxolane;

(cis/trans)-2-(3-(4-methylphenyl)propyl)-2-(5-n-butylimidazol-1-yl)-4-hydroxymethyl-1,3-dioxolane; and (cis/trans)-2-(3-(4-methylphenyl)propyl)-2-(5-n-propylimidazol-1-yl)-4-hydroxymethyl-1,3-dioxolane.

PREPARATION 9

Compounds of Formulae (D), (Da) and (Db)

A. (Cis and trans)-2-(2-(4-chlorophenyl)ethyl)-2-(imidazol-1-yl)methyl-4-hydroxymethyl-1,3-dioxolane (39.7 g) in pyridine (150 mL) at 0° C. was treated dropwise with stirring with methanesulfonyl chloride (10.6 mL) and the mixture stirred overnight. The resulting solid mass was stirred with ether (500 mL) to break up the solid, filtered and washed well with ether to give (cis/trans)-2-(2-(4-chlorophenyl)ethyl)-2-(imidazol-1-yl)methyl-4-(methylsulfonyloxy)methyl-1,3-dioxolane hydrochloride. A sample recrystallized from dichloromethane/isopropanol had m.p. 107°–111° C. (coalesces).

B. In a similar manner, but replacing (cis/trans)-2-(2-(4-chlorophenyl)ethyl)-2-(imidazol-1-yl)methyl-4-hydroxymethyl-1,3-dioxolane with other compounds of formula (C) and neutralizing the resulting salts, the following compounds of formula (D) were prepared:

(cis/trans)-2-(2-(4-fluorophenyl)ethyl)-2-(imidazol-1-yl)methyl-4-(methylsulfonyloxy)methyl-1,3-dioxolane;

(cis/trans)-2-(2-(2,4-dichlorophenyl)ethyl)-2-(imidazol-1-yl)methyl-4-(methylsulfonyloxy)methyl-1,3-dioxolane; and (cis/trans)-2-(2-phenylethyl)-2-(imidazol-1-yl)methyl-4-(methylsulfonyloxy)methyl-1,3-dioxolane.

C. In a similar manner, the following compounds of formula (D) are prepared:

(cis/trans)-2-(2-(4-methylphenyl)ethyl)-2-(imidazol-1-yl)methyl-4-(methylsulfonyloxy)methyl-1,3-dioxolane;

(cis/trans)-2-(2-(3,5-di-n-propoxyphenyl)ethyl)-2-(imidazol-1-yl)methyl-4-(methylsulfonyloxy)methyl-1,3-dioxolane;

(cis/trans)-2-(2-phenylethyl)-2-(imidazol-1-yl)methyl-4-(methylsulfonyloxy)methyl-1,3-dioxolane;

(cis/trans)-2-(2-(4-methylphenyl)ethyl)-2-(5-methylimidazol-1-yl)methyl-4-(methylsulfonyloxy)methyl-1,3-dioxolane;

(cis/trans)-2-(2-(3,5-di-n-propoxyphenyl)ethyl)-2-(5-ethylimidazol-1-yl)methyl-4-(methylsulfonyloxy)methyl-1,3-dioxolane;

(cis/trans)-2-(3-(4-methylphenyl)propyl)-2-(imidazol-1-yl)methyl-4-(methylsulfonyloxy)methyl-1,3-dioxolane;

(cis/trans)-2-(3-(3,5-di-n-propoxyphenyl)propyl)-2-(imidazol-1-yl)methyl-4-(methylsulfonyloxy)methyl-1,3-dioxolane;

(cis/trans)-2-(3-phenylpropyl)-2-(imidazol-1-yl)methyl-4-(methylsulfonyloxy)methyl-1,3-dioxolane;

(cis/trans)-2-(3-(4-methylphenyl)propyl)-2-(5-methylimidazol-1-yl)methyl-4-(methylsulfonyloxy)methyl-1,3-dioxolane; and (cis/trans)-2-(3-(3,5-di-n-propoxyphenyl)propyl)-2-(5-ethylimidazol-1-yl)methyl-4-(methylsulfonyloxy)methyl-1,3-dioxolane.

D. The remaining solid from part (A) above was basified with aqueous potassium carbonate solution, extracted with ethyl acetate (2×400 mL) and the extracts washed, dried (MgSO₄) and evaporated. The resulting semicrystalline mass was chromatographed on silica gel (900 g) eluting initially with dichloromethane, followed by aqueous ethyl acetate (2.2% water) to give 25.4 g. of (±)-cis-2-(2-(4-chlorophenyl)ethyl)-2-(imidazol-1-yl)methyl-4-(methylsulfonyloxy)methyl-1,3-dioxolane, as a snow white solid, m.p. 93.5°–96° C. Further elution gave, after a small mixed fraction, pure (±)-trans-2-(2-(4-chlorophenyl)ethyl)-2-(imidazol-1-yl)methyl-4-(methylsulfonyloxy)methyl-1,3-dioxolane, as a white solid, m.p. 93°–95° C. (The isomers are readily distinguished by their NMR spectra, and by their behavior on silica gel thin-layer plates when eluted with ethyl acetate saturated with water).

E. In a similar manner, but replacing (cis/trans)-2-(2-(4-chlorophenyl)ethyl)-2-(imidazol-1-yl)methyl-4-(methylsulfonyloxy)methyl-1,3-dioxolane with other compounds of formula (D), the following compounds of formulae (Da) and (Db) were prepared:

(±)-cis-2-(2-(4-fluorophenyl)ethyl)-2-(imidazol-1-yl)methyl-4-(methylsulfonyloxy)methyl-1,3-dioxolane;

(±)-cis-2-(2-(2,4-dichlorophenyl)ethyl)-2-(imidazol-1-yl)methyl-4-(methylsulfonyloxy)methyl-1,3-dioxolane;

(±)-cis-2-(2-phenylethyl)-2-(imidazol-1-yl)methyl-4-(methylsulfonyloxy)methyl-1,3-dioxolane;

(±)-trans-2-(2-(4-fluorophenyl)ethyl)-2-(imidazol-1-yl)methyl-4-(methylsulfonyloxy)methyl-1,3-dioxolane;

(±)-trans-2-(2-(2,4-dichlorophenyl)ethyl)-2-(imidazol-1-yl)methyl-4-(methylsulfonyloxy)methyl-1,3-dioxolane; and (±)-trans-2-(2-phenylethyl)-2-(imidazol-1-yl)methyl-4-(methylsulfonyloxy)methyl-1,3-dioxolane.

F. Alternatively, proceeding as in part (A) above, but replacing (cis/trans)-2-(2-(4-chlorophenyl)ethyl)-2-(imidazol-1-yl)methyl-4-hydroxymethyl-1,3-dioxolane with either (±)-cis-2-(2-(4-chlorophenyl)ethyl)-2-(imidazol-1-yl)methyl-4-hydroxymethyl-1,3-dioxolane or (±)-trans-2-(2-(4-chlorophenyl)ethyl)-2-(imidazol-1-yl)methyl-4-hydroxymethyl-1,3-dioxolane, as prepared below in Preparation 10, and neutralizing the resulting salts, (±)-cis-2-(2-(4-chlorophenyl)ethyl)-2-(imidazol-1-yl)methyl-4-(methylsulfonyloxy)methyl-1,3-dioxolane, 93.5°–96° C., and (±)-trans-2-(2-(4-chlorophenyl)ethyl)-2-(imidazol-1-yl)methyl-4-(methylsulfonyloxy)methyl-1,3-dioxolane, m.p. 93°–95° C., were prepared.

PREPARATION 10

Individual Racemic Mixtures of Compounds of Formula (C)

A. A solution of (cis/trans)-2-(2-(4-chlorophenyl)ethyl)-2-(imidazol-1-yl)methyl-4-hydroxymethyl-1,3-dioxolane (10.0 g) in pyridine (40 mL) at 0°–5° C. was treated over 5 minutes with stirring with 4.2 mL of benzoyl chloride. After stirring overnight, the solid mass was treated with ether (250 mL) and the resulting crude hydrochloride salt of (cis/trans)-2-(2-(4-chlorophenyl)ethyl)-2-(imidazol-1-yl)methyl-4-(benzoyloxy)methyl-1,3-dioxolane was filtered off and washed well with ether. This solid was extracted twice with boiling acetone (200 mL), filtered hot, and the resulting solid recrystallized from methanol/acetone to give (±)-trans-2-(2-(4-chlorophenyl)ethyl)-2-(imidazol-1-yl)methyl-4-(benzoyloxy)methyl-1,3-dioxolane hydrochloride as a snow white solid (4.38 g), m.p. 198.5°-202° C. The acetone extracts from above when allowed to stand at room temperature precipitated (±)-cis-2-(2-(4-chlorophenyl)ethyl)-2-(imidazol-1-yl)methyl-4-(benzoyloxymethyl)-1,3-dioxolane hydrochloride, recrystallized from acetone with m.p. 154.5°-158° C. To obtain further material the mother liquors and mixed fraction from above were evaporated, basified by stirring with aqueous potassium carbonate and ethyl acetate and chromatographed on silica gel eluting with ethyl acetate containing 2.2% water. The first fraction consisted of pure (±)-cis-2-(2-(4-chlorophenyl)ethyl)-2-(imidazol-1-yl)methyl-4-(benzoyloxy)methyl-1,3-dioxolane as an oil. Further elution gave, after a small mixed fraction, pure (±)-trans-2-(2-(4-chlorophenyl)ethyl)-2-(imidazol-1-yl)methyl-4-(benzoyloxy)methyl-1,3-dioxolane as an oil, which crystallized on standing.

B. A solution of (±)-cis-2-(2-(4-chlorophenyl)ethyl)-2-(imidazol-1-yl)methyl-4-benzoyloxymethyl-1,3-dioxolane (2.3 g) in methanol (50 mL) was treated with sodium hydroxide (2.0 g) in water (15 mL) and the mixture stirred at room temperature until reaction was complete. The methanol was evaporated giving an oil which spontaneously crystallized on cooling of the aqueous mixture. Filtration and recrystallization from ethyl acetate gave 1.56 g of (±)-cis-2-(2-(4-chlorophenyl)ethyl)-2-(imidazol-1-yl)methyl-4-hydroxymethyl-1,3-dioxolane, m.p. 116°-117.5° C. Similar hydrolysis of (±)-trans-2-(2-(4-chlorophenyl)ethyl)-2-(imidazol-1-yl)methyl-4-benzoyloxymethyl-1,3-dioxolane hydrochloride (3.04 g) gave 1.96 g. of (±)-trans-2-(2-(4-chlorophenyl)ethyl)-2-(imidazol-1-yl)methyl-4-hydroxymethyl-1,3-dioxolane, m.p. 121°-122.5° C.

C. Alternatively, using 4-phenylbenzoyl chloride instead of benzoyl chloride, there was obtained ((±)-cis and (±)-trans)-2-(2-(4-chlorophenyl)ethyl)-2-(imidazol-1-yl)methyl-4-(4-phenylbenzoyloxy)methyl-1,3-dioxolane, separable by chromatography on silica gel as above to give the respective mixtures of isomers:
(±)-cis-2-(2-(4-chlorophenyl)ethyl)-2-(imidazol-1-yl)methyl-4-(4-phenylbenzoyloxy)methyl-1,3-dioxolane; as hydrochloride salt, m.p. 180°-182.5° C.; and
(±)-trans-2-(2-(4-chlorophenyl)ethyl)-2-(imidazol-1-yl)methyl-4-(4-phenylbenzoyloxy)methyl-1,3-dioxolane; as hydrochloride salt, m.p. 135.5°-140° C.

D. Hydrolysis of the esters prepared in part (C) above in the manner described above in part (B) produces the corresponding 4-hydroxymethyl racemic mixtures of part (B) above.

PREPARATION 11

Compounds of Formula (E)

A. A mixture of 4-acetoxybenzoic acid (5.0 g) and triethylamine (3.0 g) in acetone (150 mL) at 0° C. was treated with ethyl chloroformate over 5 minutes with stirring. After a further 10 minutes, sodium azide (21.5 g) in water (10 mL) was added and the mixture maintained at 5° C. for 0.5 hour. The mixture was then concentrated at 45° C. under reduced pressure and the residue dissolved in toluene (200 mL) and washed with water and dried (Na₂SO₄). After evaporation of 100 mL of the toluene under reduced pressure, the solution was heated under reflux for 1 hour and cooled to 5° C. before addition of n-propylamine (3 mL). After a further 15 minutes, the mixture was evaporated to dryness and the residue dissolved in methanol (50 mL) and warmed with 10% aqueous NaOH (10 mL) at 60° C. for 15 minutes. Evaporation of the methanol and addition of water and 6N HCl gave a solid which was filtered, washed with water and crystallized from acetone-ether to give 4-n-propylaminocarbonylaminophenol (3.1 g).

B. 4-Methoxyaniline (10.5 g) in iodobutane (50 g) was heated under reflux overnight. Excess iodobutane was distilled off and final traces were removed in vacuo. The residue in DMF (dimethyl formamide) (50 mL) was treated with DABCO (1,4-diazobicyclo[2.2.2]octane) (20 g) and the mixture heated under reflux for 2 hours. Most of the DMF was then evaporated and the residue taken up in ethyl acetate, washed well with water, and dried (Na₂SO₄). After evaporation of the solvent the above procedure was repeated with iodobutane (50 mL) (overnight) followed by treatment with DABCO (10 g). After work-up, the resulting oil was chromatographed on silica gel eluting with 10% ethyl acetate in hexane to give 4-methoxy-N,N-dibutylaniline (9.2 g).

C. 4-Methoxy-N,N-dibutylaniline (9.2 g) in 48% hydrobromic acid (50 mL) was heated under reflux for 2.5 hours and the acid then removed under reduced pressure. Addition of water and neutralization with solid sodium bicarbonate gave a precipitate which was filtered off, washed with water and recrystallized from methanol-ether to give 4-hydroxy-N,N-dibutylaniline.

PREPARATION 12

Compounds of Formulae (Dc) and (Dd)

A. A mixture of dry 4-(4-chlorophenyl)-1-(imidazol-1-yl)butan-2-one (4.08 g, 17.6 mmol) and p-toluenesulfonic acid monohydrate (5.37 g, 28.2 mmol) in toluene (100 mL) was allowed to reflux through a Dean-Stark trap for 1.5 hours, after which the removal of water was judged complete. A solution of S-solketal tosylate (6.06 g, 21.2 mmol) in toluene (40 mL) was dried separately by a similar azeotropic distillation, and after cooling, n-butanol (1.95 mL, 21.2 mmol) was added. The cooled solution of the butanone was brought to reflux again in a fresh apparatus incorporating a condenser atop a Dean-Stark head filled with 4 Å molecular seives, and the S-solketal tosylate/butanol solution was then added in portions over one hour. The reaction mixture was heated under reflux for an additional 7 hours, then evaporated under reduced pressure and the resulting oily residue was dissolved in ethyl acetate (200 mL). The resulting solution was then washed once with aqueous sodium carbonate, twice with water, dried over Na₂SO₄ and evaporated under reduced pressure. The resulting crude product mixture (8.25 g of solid) was separated by flash chromatography on a 10"×3" O.D. silica gel column. Elution was started with a solution of 0.1% NH₄OH and 5% methanol in a 3:3:2 mixture of ethyl acetate, methylene chloride and hexane, and then gradually changed to a solution of 0.2% NH₄OH and 10% methanol in the same solvent mixture. Recrystallization of the first eluted product yielded 2.45 g of the pure stereoisomer, (2S,4S)-cis-2-(2-(4-chlorophenyl)ethyl)-2-(imidazol-1-yl)methyl-4-(p-toluenesulfonyloxy)methyl-1,3-dioxolane, (29%), m.p. 120°-122° C. The more polar product was (2R,4S)-trans-2-(2-(4-chlorophenyl)ethyl)-2-(imidazol-1-yl)methyl-4-(p-toluenesulfonyloxy)methyl-1,3-dioxolane, (3.67 g, 47%), m.p. 154°-155° C.

B. In a similar manner, but replacing 4-(4-chlorophenyl)-1-(imidazol-1-yl)butan-2-one with other compounds of formula (B), the following compounds of formulae (Dc) and (Dd) were made:

(2S,4S)-cis-2-(2-(4-methoxyphenyl)ethyl)-2-(imidazol-1-yl)methyl-4-(p-toluenesulfonyloxy)methyl-1,3-dioxolane;

(2R,4S)-trans-2-(2-(4-methoxyphenyl)ethyl)-2-(imidazol-1-yl)methyl-4-(p-toluenesulfonyloxy)methyl-1,3-dioxolane;

(2S,4S)-cis-2-(2-(2,4-dichlorophenyl)ethyl)-2-(imidazol-1-yl)methyl-4-(p-toluenesulfonyloxy)methyl-1,3-dioxolane;

(2R,4S)-trans-2-(2-(2,4-dichlorophenyl)ethyl)-2-(imidazol-1-yl)methyl-4-(p-toluenesulfonyloxy)methyl-1,3-dioxolane;

(2S,4S)-cis-2-(2-(4-fluorophenyl)ethyl)-2-(imidazol-1-yl)methyl-4-(p-toluenesulfonyloxy)methyl-1,3-dioxolane; and (2R,4S)-trans-2-(2-(4-fluorophenyl)ethyl)-2-(imidazol-1-yl)methyl-4-(p-toluenesulfonyloxy)methyl-1,3-dioxolane.

C. In a similar manner, the following compounds of formulae (Dc) and (Dd) are made:

(2S,4S)-cis-2-(2-(4-methoxyphenyl)ethyl)-2-(5-methylimidazol-1-yl)methyl-4-(p-toluenesulfonyloxy)methyl-1,3-dioxolane;

(2R,4S)-trans-2-(2-(4-methoxyphenyl)ethyl)-2-(5-methylimidazol-1-yl)methyl-4-(p-toluenesulfonyloxy)methyl-1,3-dioxolane;

(2S,4S)-cis-2-(2-(2,4-dichlorophenyl)ethyl)-2-(5-ethylimidazol-1-yl)methyl-4-(p-toluenesulfonyloxy)methyl-1,3-dioxolane;

(2R,4S)-trans-2-(2-(2,4-dichlorophenyl)ethyl)-2-(5-ethylimidazol-1-yl)methyl-4-(p-toluenesulfonyloxy)methyl-1,3-dioxolane;

(2S,4S)-cis-2-(2-(3,5-di-n-propoxyphenyl)ethyl)-2-(imidazol-1-yl)methyl-4-(p-toluenesulfonyloxy)methyl-1,3-dioxolane;

(2R,4S)-trans-2-(2-(3,5-di-n-propoxyphenyl)ethyl)-2-(imidazol-1-yl)methyl-4-(p-toluenesulfonyloxy)methyl-1,3-dioxolane;

(2S,4S)-cis-2-(2-(4-ethoxyphenyl)ethyl)-2-(imidazol-1-yl)methyl-4-(p-toluenesulfonyloxy)methyl-1,3-dioxolane;

(2R,4S)-trans-2-(2-(4-ethoxyphenyl)ethyl)-2-(imidazol-1-yl)methyl-4-(p-toluenesulfonyloxy)methyl-1,3-dioxolane;

(2S,4S)-cis-2-(2-(3,5-dimethylphenyl)ethyl)-2-(imidazol-1-yl)methyl-4-(p-toluenesulfonyloxy)methyl-1,3-dioxolane;

(2R,4S)-trans-2-(2-(3,5-dimethylphenyl)ethyl)-2-(imidazol-1-yl)methyl-4-(p-toluenesulfonyloxy)methyl-1,3-dioxolane;

(2S,4S)-cis-2-(2-phenylethyl)-2-(imidazol-1-yl)methyl-4-(p-toluenesulfonyloxy)methyl-1,3-dioxolane;

(2R,4S)-trans-2-(2-phenylethyl)-2-(imidazol-1-yl)methyl-4-(p-toluenesulfonyloxy)methyl-1,3-dioxolane;

(2S,4S)-cis-2-(3-(4-chlorophenyl)propyl)-2-(imidazol-1-yl)methyl-4-(p-toluenesulfonyloxy)methyl-1,3-dioxolane;

(2R,4S)-trans-2-(3-(4-chlorophenyl)propyl)-2-(imidazol-1-yl)methyl-4-(p-toluenesulfonyloxy)methyl-1,3-dioxolane;

(2S,4S)-cis-2-(3-(4-methoxyphenyl)propyl)-2-(imidazol-1-yl)methyl-4-(p-toluenesulfonyloxy)methyl-1,3-dioxolane;

(2R,4S)-trans-2-(3-(4-methoxyphenyl)propyl)-2-(imidazol-1-yl)methyl-4-(p-toluenesulfonyloxy)methyl-1,3-dioxolane;

(2S,4S)-cis-2-(3-(2,4-dichlorophenyl)propyl)-2-(imidazol-1-yl)methyl-4-(p-toluenesulfonyloxy)methyl-1,3-dioxolane;

(2R,4S)-trans-2-(3-(2,4-dichlorophenyl)propyl)-2-(imidazol-1-yl)methyl-4-(p-toluenesulfonyloxy)methyl-1,3-dioxolane;

(2S,4S)-cis-2-(3-(4-fluorophenyl)propyl)-2-(imidazol-1-yl)methyl-4-(p-toluenesulfonyloxy)methyl-1,3-dioxolane;

(2R,4S)-trans-2-(3-(4-fluorophenyl)propyl)-2-(imidazol-1-yl)methyl-4-(p-toluenesulfonyloxy)methyl-1,3-dioxolane;

(2S,4S)-cis-2-(3-(3,5-di-n-propoxyphenyl)propyl)-2-(imidazol-1-yl)methyl-4-(p-toluenesulfonyloxy)methyl-1,3-dioxolane;

(2R,4S)-trans-2-(3-(3,5-di-n-propoxyphenyl)propyl)-2-(imidazol-1-yl)methyl-4-(p-toluenesulfonyloxy)methyl-1,3-dioxolane;

(2S,4S)-cis-2-(3-(4-ethoxyphenyl)propyl)-2-(imidazol-1-yl)methyl-4-(p-toluenesulfonyloxy)methyl-1,3-dioxolane;

(2R,4S)-trans-2-(3-(4-ethoxyphenyl)propyl)-2-(imidazol-1-yl)methyl-4-(p-toluenesulfonyloxy)methyl-1,3-dioxolane;

(2S,4S)-cis-2-(3-(3,5-dimethylphenyl)propyl)-2-(imidazol-1-yl)methyl-4-(p-toluenesulfonyloxy)methyl-1,3-dioxolane;

(2R,4S)-trans-2-(3-(3,5-dimethylphenyl)propyl)-2-(imidazol-1-yl)methyl-4-(p-toluenesulfonyloxy)methyl-1,3-dioxolane;

(2S,4S)-cis-2-(2-phenylethyl)-2-(imidazol-1-yl)methyl-4-(p-toluenesulfonyloxy)methyl-1,3-dioxolane; and (2R,4S)-trans-2-(2-phenylethyl)-2-(imidazol-1-yl)methyl-4-(p-toluenesulfonyloxy)methyl-1,3-dioxolane.

D. In a similar manner, but replacing S-solketal tosylate with R-solketal tosylate, the following compounds of formulae (De) and (Df) were made:

(2R,4R)-cis-2-(2-(4-chlorophenyl)ethyl)-2-(imidazol-1-yl)methyl-4-(p-toluenesulfonyloxy)methyl-1,3-dioxolane;

(2S,4R)-trans-2-(2-(4-chlorophenyl)ethyl)-2-(imidazol-1-yl)methyl-4-(p-toluenesulfonyloxy)methyl-1,3-dioxolane;

(2R,4R)-cis-2-(2-(4-methoxyphenyl)ethyl)-2-(imidazol-1-yl)methyl-4-(p-toluenesulfonyloxy)methyl-1,3-dioxolane;

(2S,4R)-trans-2-(2-(4-methoxyphenyl)ethyl)-2-(imidazol-1-yl)methyl-4-(p-toluenesulfonyloxy)methyl-1,3-dioxolane;

(2R,4R)-cis-2-(2-(2,4-dichlorophenyl)ethyl)-2-(imidazol-1-yl)methyl-4-(p-toluenesulfonyloxy)methyl-1,3-dioxolane;

(2S,4R)-trans-2-(2-(2,4-dichlorophenyl)ethyl)-2-(imidazol-1-yl)methyl-4-(p-toluenesulfonyloxy)methyl-1,3-dioxolane;

(2R,4R)-cis-2-(2-(4-fluorophenyl)ethyl)-2-(imidazol-1-yl)methyl-4-(p-toluenesulfonyloxy)methyl-1,3-dioxolane; and (2S,4R)-trans-2-(2-(4-fluorophenyl)ethyl)-2-(imidazol-1-yl)methyl-4-(p-toluenesulfonyloxy)methyl-1,3-dioxolane.

E. In a similar manner, the following compounds of formulae (De) and (Df) are made:

(2R,4R)-cis-2-(2-(4-methoxyphenyl)ethyl)-2-(5-methylimidazol-1-yl)methyl-4-(p-toluenesulfonyloxy)methyl-1,3-dioxolane;

(2S,4R)-trans-2-(2-(4-methoxyphenyl)ethyl)-2-(5-methylimidazol-1-yl)methyl-4-(p-toluenesulfonyloxy)methyl-1,3-dioxolane;

(2R,4R)-cis-2-(2-(2,4-dichlorophenyl)ethyl)-2-(5-ethylimidazol-1-yl)methyl-4-(p-toluenesulfonyloxy)methyl-1,3-dioxolane;

(2S,4R)-trans-2-(2-(2,4-dichlorophenyl)ethyl)-2-(5-ethylimidazol-1-yl)methyl-4-(p-toluenesulfonyloxy)methyl-1,3-dioxolane;

(2R,4R)-cis-2-(2-(3,5-di-n-propoxyphenyl)ethyl)-2-(imidazol-1-yl)methyl-4-(p-toluenesulfonyloxy)methyl-1,3-dioxolane;

(2S,4R)-trans-2-(2-(3,5-di-n-propoxyphenyl)ethyl)-2-(imidazol-1-yl)methyl-4-(p-toluenesulfonyloxy)methyl-1,3-dioxolane;

(2R,4R)-cis-2-(2-(4-ethoxyphenyl)ethyl)-2-(imidazol-1-yl)methyl-4-(p-toluenesulfonyloxy)methyl-1,3-dioxolane;

(2S,4R)-trans-2-(2-(4-ethoxyphenyl)ethyl)-2-(imidazol-1-yl)methyl-4-(p-toluenesulfonyloxy)methyl-1,3-dioxolane;

(2R,4R)-cis-2-(2-(3,5-dimethylphenyl)ethyl)-2-(imidazol-1-yl)methyl-4-(p-toluenesulfonyloxy)methyl-1,3-dioxolane;

(2S,4R)-trans-2-(2-(3,5-dimethylphenyl)ethyl)-2-(imidazol-1-yl)methyl-4-(p-toluenesulfonyloxy)methyl-1,3-dioxolane;

(2R,4R)-cis-2-(2-phenylethyl)-2-(imidazol-1-yl)methyl-4-(p-toluenesulfonyloxy)methyl-1,3-dioxolane;

(2S,4R)-trans-2-(2-phenylethyl)-2-(imidazol-1-yl)methyl-4-(p-toluenesulfonyloxy)methyl-1,3-dioxolane;

(2R,4R)-cis-2-(3-(4-chlorophenyl)propyl)-2-(imidazol-1-yl)methyl-4-(p-toluenesulfonyloxy)methyl-1,3-dioxolane;

(2S,4R)-trans-2-(3-(4-chlorophenyl)propyl)-2-(imidazol-1-yl)methyl-4-(p-toluenesulfonyloxy)methyl-1,3-dioxolane;

(2R,4R)-cis-2-(3-(4-methoxyphenyl)propyl)-2-(imidazol-1-yl)methyl-4-(p-toluenesulfonyloxy)methyl-1,3-dioxolane;

(2S,4R)-trans-2-(3-(4-methoxyphenyl)propyl)-2-(imidazol-1-yl)methyl-4-(p-toluenesulfonyloxy)methyl-1,3-dioxolane;

(2R,4R)-cis-2-(3-(2,4-dichlorophenyl)propyl)-2-(imidazol-1-yl)methyl-4-(p-toluenesulfonyloxy)methyl-1,3-dioxolane;

(2S,4R)-trans-2-(3-(2,4-dichlorophenyl)propyl)-2-(imidazol-1-yl)methyl-4-(p-toluenesulfonyloxy)methyl-1,3-dioxolane;

(2R,4R)-cis-2-(3-(4-fluorophenyl)propyl)-2-(imidazol-1-yl)methyl-4-(p-toluenesulfonyloxy)methyl-1,3-dioxolane;

(2S,4R)-trans-2-(3-(4-fluorophenyl)propyl)-2-(imidazol-1-yl)methyl-4-(p-toluenesulfonyloxy)methyl-1,3-dioxolane;

(2R,4R)-cis-2-(3-(3,5-di-n-propoxyphenyl)propyl)-2-(imidazol-1-yl)methyl-4-(p-toluenesulfonyloxy)methyl-1,3-dioxolane;

(2S,4R)-trans-2-(3-(3,5-di-n-propoxyphenyl)propyl)-2-(imidazol-1-yl)methyl-4-(p-toluenesulfonyloxy)methyl-1,3-dioxolane;

(2R,4R)-cis-2-(3-(4-ethoxyphenyl)propyl)-2-(imidazol-1-yl)methyl-4-(p-toluenesulfonyloxy)methyl-1,3-dioxolane;

(2S,4R)-trans-2-(3-(4-ethoxyphenyl)propyl)-2-(imidazol-1-yl)methyl-4-(p-toluenesulfonyloxy)methyl-1,3-dioxolane;

(2R,4R)-cis-2-(3-(3,5-dimethylphenyl)propyl)-2-(imidazol-1-yl)methyl-4-(p-toluenesulfonyloxy)methyl-1,3-dioxolane;

(2S,4R)-trans-2-(3-(3,5-dimethylphenyl)propyl)-2-(imidazol-1-yl)methyl-4-(p-toluenesulfonyloxy)methyl-1,3-dioxolane;

(2R,4R)-cis-2-(2-phenylethyl)-2-(imidazol-1-yl)methyl-4-(p-toluenesulfonyloxy)methyl-1,3-dioxolane; and (2S,4R)-trans-2-(2-phenylethyl)-2-(imidazol-1-yl)methyl-4-(p-toluenesulfonyloxy)methyl-1,3-dioxolane.

PREPARATION 13

Alternate Synthesis of Compounds of Formulae (Dc) and (Dd)

A. A mixture of S-solketal tosylate (7.0 g, 2.45 mmol), acetone (5 mL) and 1N HCl (aqueous, 15 mL) was heated under reflux for 40 minutes. The reaction mixture was allowed to cool and evaporated to dryness. The residue was dissolved in $CH_2Cl_2$, dried ($Na_2SO_4$), and the solvent evaporated. The residue was then dried under reduced pressure to yield 6.0 g of the 2S-diol.

B. A mixture of dry 4-(4-chlorophenyl)-1-(imidazol-1-yl)butan-2-one (2.0 g, 8.04 mmol) and p-toluenesulfonic acid monohydrate (2.29 g, 12.06 mmol) in toluene (100 mL) was allowed to reflux through a Dean-Stark trap for 1.5 hours, after which the removal of water was judged complete. The reaction mixture was allowed to cool and the Dean-Stark trap and condenser were replaced with a dry condenser atop a new Dean-Stark head filled with 4 Å molecular sieves, and an emulsion of the 2S-diol (prepared above) (2.38 g, 9.65 mmol) in toluene (~30 mL) was added. The reaction mixture was heated under reflux for 4 hours, then evaporated under reduced pressure. The residue was partitioned between ethyl acetate and aqueous sodium carbonate. The organic layer was washed three times with water, dried ($Na_2SO_4$) and evaporated under reduced pressure. The resulting oily residue (3.73 g) was separated by flash chromatography on a 10"×52 mm silica gel column. Elution was started with a solution of 5.5% MeOH (containing 2.0% $NH_4OH$) in a 3:3:2 mixture of ethyl acetate:dichloromethane:hexane and then gradually changed to a solution of 8.0% MeOH (containing 2.0% $NH_4OH$) in the same solvent system. Evaporation of the first eluted product yielded 980 mg of the pure stereoisomer, (2S,4S)-cis-2-(2-(4-chlorophenyl)ethyl)-2-(imidazol-1-yl)methyl-4-(p-toluenesulfonyloxy)methyl-1,3-dioxolane (25.5%), m.p. 120°-122° C. The more polar unreacted diol was eluted next, followed by elution of the (2R,4S)-trans-stereoisomer (1.313 g, 34.2%), m.p. 154°-155° C.

PREPARATION 14

Reequilibration of Compounds of Formula (Dd) to Compounds of Formula (Dc)

A solution of p-toluenesulfonic acid monohydrate (1.90 g, 10 mmol) in xylenes (boiling range 137°-141°, 80 mL) was allowed to reflux through a Dean-Stark trap for 45 minutes, after which removal of water was judged complete. The solution was then allowed to cool and (2R,4S)-trans-2-(2-(4-chlorophenyl)ethyl)-2-(imidazol-1-yl)methyl-4-(p-toluenesulfonyloxy)methyl-1,3-dioxolane (2.39 g, 5 mmol) and dry n-heptanol (3.5 mL, 25 mmol) were added. The resulting mixture was heated to reflux in an apparatus utilizing a fresh Dean-Stark trap filled with 4 Å molecular seives. After five hours at reflux, the mixture was evaporated to dryness under reduced pressure. The residue was then dissolved in ethyl acetate (100 mL) and then triethylamine (3 mL) was added to the solution. The solution was then washed once with aqueous sodium carbonate, twice with water, dried over $Na_2SO_4$ and evaporated to dryness. The resulting crude product mixture was then separated by flash chromatography under the same conditions as described in Preparation 12 above. Recrystallization of the first eluted product yielded 0.75 g of the pure cis-enantiomer, (2S,4S)-cis-2-(2-(4-chlorophenyl)ethyl)-2-(imidazol-1-yl)methyl-4-(p-toluenesulfonyloxy)methyl-1,3-dioxolane (31%). The more polar product recovered was the unchanged trans-enantiomer, 1.11 g (46%).

EXAMPLE 1

Compounds of Formulae (Ia) and (Ib) wherein $X_a$ is sulfur

A. A mixture of (±)-cis-2-[2-(4-chlorophenyl)ethyl]-2-(imidazol-1-yl)methyl-4-(methylsulfonyloxy)methyl-1,3-dioxolane (31.0 g), 4-aminothiophenol (12.6 g) and anhydrous potassium carbonate (23.1 g) in acetone (250 mL) was stirred overnight under reflux under nitrogen. The reaction mixture was then evaporated to dryness, and the resulting residue was extracted with methylene chloride (300 mL) and filtered. The solid filter cake was then washed with methylene chloride (200 mL). The methylene chloride extracts were then combined and concentrated and flash chromatographed on a silica gel eluting with methylene chloride followed by 30% acetone in methylene chloride. After separation of the visible thiol/disulfide band, the column was further eluted with ethyl acetate containing 2.2% water to afford a pure product. The pure product was dissolved in a minimum amount of hot ethyl acetate (~125 mL), the solution diluted with an equal volume of hot hexane and seeded to give 30.0 g of (±)-cis-2-(2-(4-chlorophenyl)ethyl)-2-(imidazol-1-yl)methyl-4-(4-aminophenylthio)methyl-1,3-dioxolane, m.p. 121.5°–122.5° C.

B. In a similar manner, but replacing (±)-cis-2-(2-(4-chlorophenyl)ethyl)-2-(imidazol-1-yl)methyl-4-(methylsulfonyloxy)methyl-1,3-dioxolane with other compounds of formulae (Da) and (Db), and replacing 4-aminothiophenol with other appropriately substituted thiophenols, the following compounds of formulae (Ia) and (Ib) wherein $X_a$ is sulfur, or salts thereof, were made:

(±)-cis-2-(2-(4-methoxyphenyl)ethyl)-2-(imidazol-1-yl)methyl-4-(4-aminophenylthio)methyl-1,3-dioxolane dihydrochloride, m.p. 194°–198° C.;

(±)-cis-2-(2-(4-chlorophenyl)ethyl)-2-(imidazol-1-yl)methyl-4-(2-aminophenylthio)methyl-1,3-dioxolane bis(nitrate), m.p. 127°–138° C.;

(±)-cis-2-(2-(4-chlorophenyl)ethyl)-2-(imidazol-1-yl)methyl-4-(4-acetamidophenylthio)methyl-1,3-dioxolane, m.p. 128°–129° C.;

(±)-cis-2-(2-(4-chlorophenyl)ethyl)-2-(imidazol-1-yl)methyl-4-(3-aminophenylthio)methyl-1,3-dioxolane, m.p. 94.5°–98° C.; and (±)-trans-2-(2-(4-chlorophenyl)ethyl-2-(imidazol-1-yl)methyl-4-(4-aminophenylthio)methyl-1,3-dioxolane, m.p. 146°–147° C.

C. In a similar manner, the following compounds of formulae (Ia) and (Ib) wherein $X_a$ is sulfur are made:

(±)-cis-2-(2-(2,4-dichlorophenyl)ethyl)-2-(imidazol-1-yl)methyl-4-(4-aminophenylthio)methyl-1,3-dioxolane;

(±)-cis-2-(2-(4-chlorophenyl)ethyl)-2-(imidazol-1-yl)methyl-4-(4-amino-2,6-dichlorophenylthio)methyl-1,3-dioxolane;

(±)-cis-2-(2-(4-chlorophenyl)ethyl)-2-(imidazol-1-yl)methyl-4-(4-amino-2-methylphenylthio)methyl-1,3-dioxolane; and (±)-cis-2-(2-(4-chlorophenyl)ethyl)-2-(5-ethylimidazol-1-yl)methyl-4-(4-amino-2-methylphenylthio)methyl-1,3-dioxolane.

EXAMPLE 2

Compounds of (Ia) and (Ib) wherein $X_a$ is oxygen

A. A mixture of 4-acetamidophenol (1.36 g) and sodium hydride (440 mg of a 50% dispersion in mineral oil) in dry DMSO (30 mL) was stirred under nitrogen at 85° C. until a clear solution resulted. (±)-cis-2-(2-(4-Chlorophenyl)ethyl)-2-(imidazol-1-yl)methyl-4-(methylsulfonyloxy)methyl-1,3-dioxolane (3.0 g) was then added and the mixture stirred overnight at 85° C. The resulting mixture was then cooled to room temperature, diluted with water until almost turbid, seeded, stirred until crystallization was complete and filtered. The resulting solid was washed with water, dried in air and recrystallized twice from methanol-acetone to give 2.08 g of (±)-cis-2-(2-(4-chlorophenyl)ethyl)-2-(imidazol-1-yl)methyl-4-(4-acetamidophenoxy)methyl-1,3-dioxolane, m.p. 179°–180° C.

B. In a similar manner, but replacing 4-acetamidophenol with other appropriately substituted phenols, the following compounds of formulae (Ia) and (Ib) wherein $X_a$ is oxygen, or salts thereof, were made:

(±)-cis-2-(2-(4-methoxyphenyl)ethyl)-2-(imidazol-1-yl)methyl-4-(4-aminophenoxy)methyl-1,3-dioxolane, m.p. 143°–147° C.;

(±)-cis-2-(2-(4-chlorophenyl)ethyl)-2-(imidazol-1-yl)methyl-4-(4-aminophenoxy)methyl-1,3-dioxolane, m.p. 118°–119° C.;

(±)-cis-2-(3-(4-chlorophenyl)propyl)-2-(imidazol-1-yl)methyl-4-(4-(4-acetylpiperazino)phenoxy)methyl-1,3-dioxolane dihydrochloride, m.p. 144°–146° C.;

(±)-cis-2-(2-(4-methoxyphenyl)ethyl)-2-(imidazol-1-yl)methyl-4-(4-acetamidophenoxy)methyl-1,3-dioxolane, m.p. 163.5°–166° C.;

(±)-cis-2-(2-(4-methoxyphenyl)ethyl)-2-(imidazol-1-yl)methyl-4-(4-(4-acetylpiperazino)phenoxy)methyl-1,3-dioxolane, m.p. 137°–140° C.;

(±)-cis-2-(2-(4-chlorophenyl)ethyl)-2-(imidazol-1-yl)methyl-4-(2-acetamidophenoxy)methyl-1,3-dioxolane hydrochloride, m.p. 82.5°–87.5° C.;

(±)-trans-2-(2-(4-chlorophenyl)ethyl)-2-(imidazol-1-yl)methyl-4-(2-acetamidophenoxy)methyl-1,3-dioxolane, m.p. 138°–139° C.;

(±)-cis-2-(2-(4-chlorophenyl)ethyl)-2-(imidazol-1-yl)methyl-4-(2-pyrrolidinophenoxy)methyl-1,3-dioxolane, m.p. 120°–123° C.;

(±)-cis-2-(2-(4-chlorophenyl)ethyl)-2-(imidazol-1-yl)methyl-4-(2-piperidinophenoxy)methyl-1,3-dioxolane, m.p. 113°–116° C.;

(±)-cis-2-(2-(4-chlorophenyl)ethyl)-2-(imidazol-1-yl)methyl-4-(3-acetamidophenoxy)methyl-1,3-dioxolane hydrochloride, m.p. 190°–193° C.;

(±)-trans-2-(2-(4-chlorophenyl)ethyl)-2-(imidazol-1-yl)methyl-4-(3-acetamidophenoxy)methyl-1,3-dioxolane hydrogen oxalate, m.p. 122°–124° C.;

(±)-cis-2-(2-(4-chlorophenyl)ethyl)-2-(imidazol-1-yl)methyl-4-(3-pyrrolidinophenoxy)methyl-1,3-dioxolane, m.p. 81.5°–83° C.;

(±)-cis-2-(2-(4-chlorophenyl)ethyl)-2-(imidazol-1-yl)methyl-4-(3-piperidinophenoxy)methyl-1,3-dioxolane, m.p. 82°–87° C.;

(±)-cis-2-(2-(4-chlorophenyl)ethyl)-2-(imidazol-1-yl)methyl-4-(4-nitrophenoxy)methyl-1,3-dioxolane nitrate, m.p. 159.5°–161.5° C.;

(±)-trans-2-(2-(4-chlorophenyl)ethyl)-2-(imidazol-1-yl)methyl-4-(4-acetamidophenoxy)methyl-1,3-dioxolane, m.p. 151°–153° C.;

(±)-cis-2-(2-(4-chlorophenyl)ethyl)-2-(imidazol-1-yl)methyl-4-(4-propylaminocarbonylaminophenoxy)methyl-1,3-dioxolane, m.p. 126°–128° C.;

(±)-cis-2-(2-(4-chlorophenyl)ethyl)-2-(imidazol-1-yl)methyl-4-(4-methylaminophenoxy)methyl-1,3-dioxolane, m.p. 107°–109° C.;

(±)-cis-2-(2-(4-chlorophenyl)ethyl)-2-(imidazol-1-yl)methyl-4-(4-dimethylaminophenoxy)methyl-1,3-dioxolane, m.p. 115°–116° C.;

(±)-cis-2-(2-(4-chlorophenyl)ethyl)-2-(imidazol-1-yl)methyl-4-(4-dibutylaminophenoxy)methyl-1,3-dioxolane, m.p. 60°–62° C.;

(±)-cis-2-(2-(4-chlorophenyl)ethyl)-2-(imidazol-1-yl)methyl-4-(4-pyrrolidinophenoxy)methyl-1,3-dioxolane, m.p. 117°–118° C.;

(±)-cis-2-(2-(4-chlorophenyl)ethyl)-2-(imidazol-1-yl)methyl-4-(4-pyrrolidinophenoxy)methyl-1,3-dioxolane hydrogen oxalate, m.p. 155°–159° C.;

(±)-cis-2-(2-(4-chlorophenyl)ethyl)-2-(imidazol-1-yl)methyl-4-(4-piperidinophenoxy)methyl-1,3-dioxolane, m.p. 106°–107° C.;

(±)-cis-2-(2-(4-chlorophenyl)ethyl)-2-(imidazol-1-yl)methyl-4-(4-piperidinophenoxy)methyl-1,3-dioxolane dihydrochloride, m.p. 120°–125° C. (dec.) (Et$_2$O.H$_2$O);

(±)-trans-2-(2-(4-chlorophenyl)ethyl)-2-(imidazol-1-yl)methyl-4-(4-piperidinophenoxy)methyl-1,3-dioxolane, m.p. 77°–78° C.;

(±)-cis-2-(2-(4-chlorophenyl)ethyl)-2-(imidazol-1-yl)methyl-4-(4-piperazinophenoxy)methyl-1,3-dioxolane, m.p. 132°–135° C.;

(±)-cis-2-(2-(4-chlorophenyl)ethyl)-2-(imidazol-1-yl)methyl-4-(4-piperazinophenoxy)methyl-1,3-dioxolane trihydrochloride, m.p. 244°–255° C.;

(±)-cis-2-(2-(4-chlorophenyl)ethyl)-2-(imidazol-1-yl)methyl-4-(4-(4-formylpiperazino)phenoxy)methyl-1,3-dioxolane, m.p. 120°–123° C.;

(±)-cis-2-(2-(4-chlorophenyl)ethyl)-2-(imidazol-1-yl)methyl-4-(4-(4-acetylpiperazino)phenoxy)methyl-1,3-dioxolane, m.p. 144°–145° C.; and (±)-cis-2-(2-(4-chlorophenyl)ethyl)-2-(imidazol-1-yl)methyl-4-(4-(4-propionylcarbonylpiperazino)phenoxy)methyl-1,3-dioxolane nitrate, m.p. 108°–116° C.

C. In a similar manner, the following compounds of formula (Ia) and (Ib) where X is oxygen are made:

(±)-cis-2-(2-(2,4-dimethylphenyl)ethyl)-2-(imidazol-1-yl)methyl-4-(4-aminophenoxy)methyl-1,3-dioxolane;

(±)-cis-2-(2-(4-methoxyphenyl)ethyl)-2-(imidazol-1-yl)methyl-4-(4-amino-2,6-dimethylphenoxy)methyl-1,3-dioxolane;

(±)-cis-2-(2-(4-chlorophenyl)ethyl)-2-(imidazol-1-yl)methyl-4-(4-amino-2-fluorophenoxy)methyl-1,3-dioxolane; and (±)-cis-2-(2-(4-trifluoromethylphenyl)ethyl)-2-(5-n-propylimidazol-1-yl)methyl-4-(4-amino-2-methylphenoxy)methyl-1,3-dioxolane.

EXAMPLE 3

Compounds of Formulae (Ic), (Id), (Ie) and (If) wherein X is S(O)$_t$ where t is 0

A. A mixture of (2S, 4S)-cis-2-(2-(4-chlorophenyl)ethyl)-2-(imidazol-1-yl)methyl-4-(p-toluenesulfonyloxy)methyl-1,3-dioxolane (1.00 g, 2.1 mmol), 4-aminothiophenol (0.53 g, 4.2 mmol) and potassium carbonate (0.58 g, 4.2 mmol) in acetone (40 mL) was heated under reflux under N$_2$ for four hours, after which it was concentrated by evaporation under reduced pressure. The mixture was diluted with ethyl acetate, washed three times with water, dried over Na$_2$SO$_4$, and then evaporated to dryness under reduced pressure. The resulting oil was purified by flash chromatography on a 7"×45 mm OD silica gel column, using a solution of 0.1% NH$_4$OH and 6% methanol in a 3:3:2 mixture of ethyl acetate, methylene chloride and hexane as the eluent. Recrystallization of the recovered product from ethyl acetate and hexane gave 0.76 g (84%) of (2S, 4S)-cis-2-(2-(4-chlorophenyl)ethyl)-2-(imidazol-1-yl)methyl-4-(4-aminophenylthio)methyl-1,3-dioxolane, m.p. 121°–121.5° C., [α]$_D$+16.1° (c=0.5, CHCl$_3$).

B. In a similar manner, but replacing (2S, 4S)-cis-2-(2-(4-chlorophenyl)ethyl)-2-(imidazol-1-yl)methyl-4-(p-toluenesulfonyloxy)methyl-1,3-dioxolane with other compounds of formulae (Dc) and (Dd), or replacing 4-aminothiophenol with the appropriately substituted thiophenol, the following compounds of formulae (Ic) and (Id), or salts thereof, were made:

(2S, 4S)-cis-2-(2-(4-methoxyphenyl)ethyl)-2-(imidazol-1-yl)methyl-4-(4-aminophenylthio)methyl-1,3-dioxolane, m.p. 94.9°–95.5° C., [α]$_D$+15.2° (c=0.4, CHCl$_3$);

(2S, 4S)-cis-2-(2-(2,4-dichlorophenyl)ethyl)-2-(imidazol-1-yl)methyl-4-(4-aminophenylthio)methyl-1,3-dioxolane, m.p. 105.5°–107.5° C., [α]$_D$+17.4° (c=0.4, CHCl$_3$);

(2S, 4S)-cis-2-(2-(4-chlorophenyl)ethyl)-2-(5-methylimidazol-1-yl)methyl-4-(4-aminophenylthio)methyl-1,3-dioxolane oxalate, m.p. 153.5°–154.5° C., [α]$_D$+27° (c=0.4, MeOH);

(2S, 4S)-cis-2-(2-(4-fluorophenyl)ethyl)-2-(imidazol-1-yl)methyl-4-(4-aminophenylthio)methyl-1,3-dioxolane bis(hydrogen oxalate), m.p. 174°–176° C., [α]$_D$+13.0° (c=0.4, MeOH);

(2R, 4S)-trans-2-(2-(4-chlorophenyl)ethyl)-2-(imidazol-1-yl)methyl-4-(4-aminophenylthio)methyl-1,3-dioxolane, m.p. 165.5°–166.5° C., [α]$_D$+13.6° (c=0.5, CHCl$_3$); and (2S, 4S)-cis-2-(2-phenylethyl)-2-(imidazol-1-yl)methyl-4-(aminophenylthio)methyl-1,3-dioxolane bis (hydrogen oxalate), m.p. 158.5°–160.5° C. (dec), [α]$_D$+11.8° (c=0.4, MeOH).

C. In a similar manner, but replacing (2S, 4S)-cis-2-(2-(4-chlorophenyl)ethyl)-2-(imidazol-1-yl)methyl-4-(p-toluenesulfonyloxy)methyl-1,3-dioxolane with other compounds of formulae (De) and (Df), the following compounds of formulae (Ie) and (If), or salts thereof, were made:

(2R, 4R)-cis-2-(2-(4-chlorophenyl)ethyl)-2-(imidazol-1-yl)methyl-4-(4-aminophenylthio)methyl-1,3-dioxolane, m.p. 120°–121° C., [α]$_D$−27.9° (c=0.4, MeOH);

(2R, 4R)-cis-2-(2-(4-methoxyphenyl)ethyl)-2-(imidazol-1-yl)methyl-4-(4-aminophenylthio)methyl-1,3-dioxolane, m.p. 94°-95.6° C., $[\alpha]_D -16.1°$ (c=0.4, CHCl$_3$);

(2R, 4R)-cis-2-(2-(2,4-dichlorophenyl)ethyl)-2-(imidazol-1-yl)methyl-4-(4-aminophenylthio)methyl-1,3-dioxolane, m.p. 109.5°-110.5° C., $[\alpha]_D -16.8°$ (c=0.4, CHCl$_3$);

(2R, 4R)-cis-2-(2-(4-fluorophenyl)ethyl)-2-(imidazol-1-yl)methyl-4-(4-aminophenylthio)methyl-1,3-dioxolane bis(hydrogen oxalate), m.p. 175°-176.5° C., $[\alpha]_D -10.4°$ (c=0.4, MeOH);

(2R, 4R)-cis-2-(2-phenylethyl)-2-(imidazol-1-yl)methyl-4-(4-aminophenylthio)methyl-1,3-dioxolane bis(hydrogen oxalate), m.p. 165°-167° C. (foams);

(2S, 4R)-trans-2-(2-(4-chlorophenyl)ethyl)-2-(imidazol-1-yl)methyl-4-(4-aminophenylthio)methyl-1,3-dioxolane, m.p. 164°-167° C., $[\alpha]_D -18.7°$ (c=0.7, CHCl$_3$); and (2R, 4R)-cis-2-(2-(4-chlorophenylethyl))-2-(5-methylimidazol-1-yl)methyl-4-(4-aminophenylthio)-methyl-1,3-dioxolane oxalate, m.p. 155°-157° C., $[\alpha]_D -27.9°$ (c=0.4, MeOH).

C. In a similar manner, the following compounds of formulae (Ic), (Id), (Ie) and (If) are made:

(2S, 4S)-cis-2-(2-(2,4-dichlorophenyl)ethyl)-2-(imidazol-1-yl)methyl-4-(4-aminophenylthio)methyl-1,3-dioxolane;

(2S, 4S)-cis-2-(2-(4-chlorophenyl)ethyl)-2-(imidazol-1-yl)methyl-4-(4-amino-2,6-dichlorophenylthio)methyl-1,3-dioxolane;

(2S, 4S)-cis-2-(2-(4-chlorophenyl)ethyl)-2-(imidazol-1-yl)methyl-4-(4-amino-2-methylphenylthio)methyl-1,3-dioxolane;

(2S, 4S)-cis-2-(2-(4-chlorophenyl)ethyl)-2-(5-ethylimidazol-1-yl)methyl-4-(4-amino-2-methylphenylthio)methyl-1,3-dioxolane;

(2R, 4R)-cis-2-(2-(2,4-dichlorophenyl)ethyl)-2-(imidazol-1-yl)methyl-4-(4-aminophenylthio)-methyl-1,3-dioxolane;

(2R, 4R)-cis-2-(2-(4-chlorophenyl)ethyl)-2-(imidazol-1-yl)methyl-4-(4-amino-2,6-dichlorophenylthio)methyl-1,3-dioxolane;

(2R, 4R)-cis-2-(2-(4-chlorophenyl)ethyl)-2-(imidazol-1-yl)methyl-4-(4-amino-2-methylphenylthio)methyl-1,3-dioxolane;

(2R, 4R)-cis-2-(2-(4-chlorophenyl)ethyl)-2-(5-ethylimidazol-1-yl)methyl-4-(4-amino-2-methylphenylthio)methyl-1,3-dioxolane;

(2S, 4R)-trans-2-(2-(2,4-dichlorophenyl)ethyl)-2-(imidazol-1-yl)methyl-4-(4-aminophenylthio)methyl-1,3-dioxolane;

(2S, 4R)-trans-2-(2-(4-chlorophenyl)ethyl)-2-(imidazol-1-yl)methyl-4-(4-amino-2,6-dichlorophenylthio)-methyl-1,3-dioxolane;

(2S, 4R)-trans-2-(2-(4-chlorophenyl)ethyl)-2-(imidazol-1-yl)methyl-4-(4-amino-2-methylphenylthio)methyl-1,3-dioxolane;

(2S, 4R)-trans-2-(2-(4-chlorophenyl)ethyl)-2-(5-ethylimidazol-1-yl)methyl-4-(4-amino-2-methylphenylthio)methyl-1,3-dioxolane;

(2R, 4S)-trans-2-(2-(2,4-dichlorophenyl)ethyl)-2-(imidazol-1-yl)methyl-4-(4-aminophenylthio)-methyl-1,3-dioxolane;

(2R, 4S)-trans-2-(2-(4-chlorophenyl)ethyl)-2-(imidazol-1-yl)methyl-4-(4-amino-2,6-dichlorophenylthio)-methyl-1,3-dioxolane;

(2R, 4S)-trans-2-(2-(4-chlorophenyl)ethyl)-2-(imidazol-1-yl)methyl-4-(4-amino-2-methylphenylthio)methyl-1,3-dioxolane; and (2R, 4S)-trans-2-(2-(4-chlorophenyl)ethyl)-2-(5-ethylimidazol-1-yl)methyl-4-(4-amino-2-methylphenylthio)methyl-1,3-dioxolane.

EXAMPLE 4

Compounds of Formulae (Ic), (Id), (Ie) and (If) wherein X is oxygen

A. In a similar manner as described above in Example 2, but replacing 4-acetamidophenol with other appropriately substituted phenols, the following compounds of formulae (Ic), (Id), (Ie) and (If), or salts thereof, were made:

(2S, 4R)-cis-2-(2-(4-chlorophenyl)ethyl)-2-(imidazol-1-yl)methyl-4-(4-aminophenoxy)methyl-1,3-dioxolane, m.p. 128°-128.5° C., $[\alpha]_D +2.8°$ (c=0.4, CHCl$_3$);

(2S,4R)-cis-2-(2-(4-chlorophenyl)ethyl)-2-(imidazol-1-yl)-methyl-4-(4-acetamidophenoxy)methyl-1,3-dioxolane, m.p. 148°-149.5° C., $[\alpha]_D +5.2°$ (c=0.4, CHCl$_3$);

(2R,4S)-cis-2-(2-(4-chlorophenyl)ethyl)-2-(imidazol-1-yl)-methyl-4-(4-acetamidophenoxy)methyl-1,3-dioxolane, m.p. 149°-151° C., $[\alpha]_D -9.4°$ (c=0.4, CHCl$_3$); and (2R,4S)-cis-2-(2-(4-chlorophenyl)ethyl)-2-(imidazol-1-yl)methyl-4-(4-aminophenoxy)methyl-1,3-dioxolane, m.p. 127°-128.5° C., $[\alpha]_D -5.1°$ (c=0.4, CHCl$_3$)

B. In a similar manner, the following compounds of formulae (Ic), (Id), (Ie) and (If) where X is oxygen are made:

(2S,4R)-cis-2-(2-(2,4-dimethylphenyl)ethyl)-2-(imidazol-1-yl)methyl-4-(4-aminophenoxy)-methyl-1,3-dioxolane;

(2S,4R)-cis-2-(2-(4-methoxyphenyl)ethyl)-2-(imidazol-1-yl)methyl-4-(4-amino-2,6-dimethylphenoxy)methyl-1,3-dioxolane;

(2S,4R)-cis-2-(2-(4-chlorophenyl)ethyl)-2-(imidazol-1-yl)methyl-4-(4-amino-2-fluorophenoxy)methyl-1,3-dioxolane;

(2S,4R)-cis-2-(2-(4-trifluoromethylphenyl)ethyl)-2-(5-n-propylimidazol-1-yl)methyl-4-(4-amino-2-methylphenoxy)methyl-1,3-dioxolane;

(2R,4S)-cis-2-(2-(2,4-dimethylphenyl)ethyl)-2-(imidazol-1-yl)methyl-4-(4-aminophenoxy)-methyl-1,3-dioxolane;

(2R,4S)-cis-2-(2-(4-methoxyphenyl)ethyl)-2-(imidazol-1-yl)methyl-4-(4-amino-2,6-dimethylphenoxy)methyl-1,3-dioxolane;

(2R,4S)-cis-2-(2-(4-chlorophenyl)ethyl)-2-(imidazol-1-yl)methyl-4-(4-amino-2-fluorophenoxy)methyl-1,3-dioxolane;

(2R,4S)-cis-2-(2-(4-trifluoromethylphenyl)ethyl)-2-(5-n-propylimidazol-1-yl)methyl-4-(4-amino-2-methylphenoxy)methyl-1,3-dioxolane;

(2S,4S)-trans-2-(2-(2,4-dimethylphenyl)ethyl)-2-(imidazol-1-yl)methyl-4-(4-aminophenoxy)methyl-1,3-dioxolane;

(2S,4S)-trans-2-(2-(4-methoxyphenyl)ethyl)-2-(imidazol-1-yl)methyl-4-(4-amino-2,6-dimethylphenoxy)methyl-1,3-dioxolane;

(2S,4S)-trans-2-(2-(4-chlorophenyl)ethyl)-2-(imidazol-1-yl)methyl-4-(4-amino-2-fluorophenoxy)methyl-1,3-dioxolane;

(2S,4S)-trans-2-(2-(4-trifluoromethylphenyl)ethyl)-2-(5-n-propylimidazol-1-yl)methyl-4-(4-amino-2-methylphenoxy)methyl-1,3-dioxolane;
(2R,4R)-trans-2-(2-(2,4-dimethylphenyl)ethyl)-2-(imidazol-1-yl)methyl-4-(4-aminophenoxy)methyl-1,3-dioxolane;
(2R,4R)-trans-2-(2-(4-methoxyphenyl)ethyl)-2-(imidazol-1-yl)methyl-4-(4-amino-2,6-dimethylphenoxy)methyl-1,3-dioxolane;
(2R,4R)-trans-2-(2-(4-chlorophenyl)ethyl)-2-(imidazol-1-yl)methyl-4-(4-amino-2-fluorophenoxy)methyl-1,3-dioxolane; and
(2R,4R)-trans-2-(2-(4-trifluoromethylphenyl)ethyl)-2-(5-n-propylimidazol-1-yl)methyl-4-(4-amino-2-methylphenoxy)methyl-1,3-dioxolane.

EXAMPLE 5

Compounds of Formula (I) wherein $R^3$ is $N(R^5)R^6$ where $R^5$ is hydrogen or lower alkyl and $R^6$ is —$C(Y)R^7$ where Y is oxygen and $R^7$ is lower alkyl A. A mixture of (2S,4S)-cis-2-(2-(4-chlorophenyl)ethyl)-2-(imidazol-1-yl)methyl-4-(4-aminophenylthio)methyl-1,3-dioxolane (300 mg) and acetic anhydride (5 mL) was stirred at room temperature under nitrogen for 2.5 hours. The mixture was then diluted with ether and the product (309 mg) filtered off and recrystallized from ethyl acetate/hexane to give (2S,4S)-cis-2-(2-(4-chlorophenyl)ethyl)-2-(imidazol-1-yl)methyl-4-(4-acetamidophenylthio)methyl-1,3-dioxolane as white platelets, m.p. 147°-148° C., $[\alpha]_D$+6.7° (c=0.2, CHCl$_3$).

B. In a similar manner, but replacing (2S,4S)-cis-2-(2-(4-chlorophenyl)ethyl)-2-(imidazol-1-yl)methyl-4-(4-aminophenylthio)methyl-1,3-dioxolane with the appropriately substituted compound of formula (I), the following compounds were made:
(±)-cis-2-(2-(4-chlorophenyl)ethyl)-2-(imidazol-1-yl)methyl-4-(4-(N-methylacetamido)phenoxy)methyl-1,3-dioxolane, m.p. 135°-137° C.;
(±)-cis-2-(2-(4-chlorophenyl)ethyl)-2-(imidazol-1-yl)methyl-4-(2-acetamidophenylthio)methyl-1,3-dioxolane hydrogen oxalate, m.p. 118°-121° C.;
(±)-cis-2-(2-(4-chlorophenyl)ethyl)-2-(imidazol-1-yl)methyl-4-(3-acetamidophenylthio)methyl-1,3-dioxolane, m.p. 122°-125° C.;
(±)-trans-2-(2-(4-chlorophenyl)ethyl)-2-(imidazol-1-yl)methyl-4-(4-acetamidophenylthio)methyl-1,3-dioxolane, m.p. 146°-147° C.;
(2S,4S)-cis-2-(2-(4-methoxyphenyl)ethyl)-2-(imidazol-1-yl)methyl-4-(4-acetamidophenylthio)methyl-1,3-dioxolane, m.p. 118°-120° C., $[\alpha]_D$+7.2° (c=0.4, CHCl$_3$);
(2R,4R)-cis-2-(2-(4-methoxyphenyl)ethyl)-2-(imidazol-1-yl)methyl-4-(4-acetamidophenylthio)methyl-1,3-dioxolane, m.p. 117°-118° C., $[\alpha]_D$−16.8° (c=0.4, CHCl$_3$);
(2S,4S)-cis-2-(2-(2,4-dichlorophenyl)ethyl)-2-(imidazol-1-yl)methyl-4-(4-acetamidophenylthio)methyl-1,3-dioxolane, m.p. 150.5°-151° C.;
(2R,4R)-cis-2-(2-(2,4-dichlorophenyl)ethyl)-2-(imidazol-1-yl)methyl-4-(4-acetamidophenylthio)methyl-1,3-dioxolane, m.p. 152.5°-153° C.; and
(2R,4R)-cis-2-(2-(4-chlorophenyl)ethyl)-2-(imidazol-1-yl)methyl-4-(4-acetamidophenylthio)methyl-1,3-dioxolane, m.p. 146°-147° C., $[\alpha]_D$−13.8° (c=0.4, CHCl$_3$).

C. In a similar manner, but replacing (2S,4S)-cis-2-(2-(4-chlorophenyl)ethyl)-2-(imidazol-1-yl)methyl-4-(4-aminophenylthio)methyl-1,3-dioxolane with (±)-cis-2-(2-(4-chlorophenyl)ethyl)-2-(imidazol-1-yl)methyl-4-(4-aminophenoxy)methyl-1,3-dioxolane and acetic anhydride with formic-acetic mixed anhydride, the following compound was made:
(±)-cis-2-(2-(4-chlorophenyl)ethyl)-2-(imidazol-1-yl)methyl-4-(4-formamidophenoxy)methyl-1,3-dioxolane, m.p. 157°-158° C.

EXAMPLE 6

Compounds of Formula (I) wherein $R^3$ is —$N(R^5)R^6$ where $R^5$ is hydrogen or lower alkyl and $R^6$ is lower alkylsulfonyl or —$C(Y)R^7$ where Y is oxygen and $R^7$ is lower alkoxy; or $R^5$ and $R^6$ together with N is piperazino substituted at the 4-position by —$C(O)R^{10}$ where $R^{10}$ is lower alkoxy A. A solution of (±)-cis-2-(2-(4-chlorophenyl)ethyl)-2-(imidazol-1-yl)methyl-4-(4-aminophenylthio)methyl-1,3-dioxolane (800 mg) in dry pyridine (10 mL) was cooled to −40° C. with stirring and treated with methyl chloroformate (0.5 mL). The temperature was maintained for 30 min., and the reaction mixture then allowed to warm to room temperature overnight. The pyridine was evaporated in vacuo and the residue then stirred with water (30 mL) and ether (20 mL). The resulting copious white precipitate was filtered off, washed with ether, water and dried in air. Recrystallization from ethyl acetate/ether gave (±)-cis-2-(2-(4-chlorophenyl)-2-(imidazol-1-yl)methyl-4-(4-methoxycarbonylaminophenylthio)methyl-1,3,-dioxolane (710 mg) as an off-white solid, m.p. 127°-128° C.

B. In a similar manner, but replacing (±)-cis-2-(2-(4-chlorophenyl)ethyl)-2-(imidazol-1-yl)methyl-4-(4-aminophenylthio)methyl-1,3-dioxolane with the appropriately substituted compound of formula (I), the following compound was made:
(±)-cis-2-(2-(4-chlorophenyl)-2-(imidazol-1-yl)methyl-4-(4-(4-methoxycarbonylpiperazino)phenoxy)methyl-1,3,-dioxolane, m.p. 122°-124° C.; and
(±)-cis-2-(2-(4-chlorophenyl)-2-(imidazol-1-yl)methyl-4-(4-ethoxycarbonylaminophenoxy)methyl-1,3,-dioxolane, m.p. 124°-125° C.

C. In a similar manner, but replacing methyl chloroformate with mesyl chloride, the following compound was made:
(±)-cis-2-(2-(4-chlorophenyl)-2-(imidazol-1-yl)methyl-4-(4-methylsulfonylaminophenylthio)methyl-1,3,-dioxolane, m.p. 175°-176° C.

EXAMPLE 7

Compounds of Formula (I) wherein $R^3$ is —$N(R^5)R^6$ where $R^5$ is hydrogen or lower alkyl and $R^6$ is —$C(Y)R^7$ where Y is oxygen and $R^7$ is —$N(R^8)R^9$ where $R^8$ and $R^9$ is hydrogen; or $R^5$ and $R^6$ together with N is piperazino substituted at the 4-position by —$C(O)R^{10}$ where $R^{10}$ is amino A. A mixture of (±)-cis-2-(2-(4-chlorophenyl)ethyl)-2-(imidazol-1-yl)methyl-4-(4-aminophenylthio)methyl-1,3-dioxolane (800 mg) and 1N HCl (2 mL) in water (20 mL) was treated with potassium cyanate (170 mg) and stirred overnight at room temperature. The resulting mixture was then basified with aqueous potassium carbonate and extracted with ethyl acetate (2×50 mL). The extracts were washed, dried (MgSO$_4$), evaporated and the residue was chromatographed on silica gel eluting with 2.2% water in ethyl acetate. The pure product crystallized from ethyl acetate/ether and was recrystallized from the same solvent to give (±)-cis-2-(2-(4- chlorophenyl)ethyl)-2-(imidazol-1-yl)methyl-4-(4-aminocarbonylaminophenylthio)methyl-1,3,-dioxolane (400 mg), m.p. 120°–121° C.

B. In a similar manner, but replacing (±)-cis-2-(2-(4-chlorophenyl)ethyl)-2-(imidazol-1-yl)methyl-4-(4-aminophenylthio)methyl-1,3-dioxolane with other appropriately substituted compounds of formula (I), the following compounds were made:

(±)-cis-2-(2-(4-chlorophenyl)ethyl)-2-(imidazol-1-yl)methyl-4-(4-aminocarbonylaminophenoxy)methyl-1,3-dioxolane, m.p. 183°–184° C.; and (±)-cis-2-(2-(4-chlorophenyl)ethyl)-2-(imidazol-1-yl)methyl-4-(4-(4-(aminocarbonyl)piperazino)-phenoxy)methyl-1,3-dioxolane, m.p. 193°–195° C.

EXAMPLE 8

Compounds of Formula (I) where $R^3$ is —N($R^5$)$R^6$ where $R^5$ is hydrogen or lower alkyl and $R^6$ is —C-(Y)$R^7$ where Y is oxygen or sulfur and $R^7$ is —N($R^8$)$R^9$ where $R^8$ is hydrogen and $R^9$ is lower alkyl or lower alkoxycarbonyl A. A mixture of (±)-cis-2-(2-(4-chlorophenyl)ethyl)-2-(imidazol-1-yl)methyl-4-(4-aminophenylthio)methyl-1,3-dioxolane (800 mg) and ethyl isothiocyanate (1 mL) in dry tetrahydrofuran (20 mL) was heated under gentle reflux for two days. Evaporation of the solvent gave an oil which crystallized upon addition of ethyl acetate/hexane. Filtration and recrystallization from ethyl acetate gave (±)-cis-2-(2-(4-chlorophenyl)ethyl)-2-(imidazol-1-yl)methyl-4-(4-(ethylamino(thiocarbonyl)amino)phenylthio)methyl-1,3-dioxolane (820 mg), m.p. 126°–127.5° C.

B. In a similar manner, but replacing (±)-cis-2-(2-(4-chlorophenyl)ethyl)-2-(imidazol-1-yl)methyl-4-(4-aminophenylthio)methyl-1,3-dioxolane with the appropriately substituted compound of formula (I) the following compound was made:

(±)-cis-2-(2-(4-chlorophenyl)ethyl)-2-(imidazol-1-yl)methyl-4-(4-(ethylamino(thiocarbonyl)amino)-phenoxy)methyl-1,3-dioxolane; m.p. 118°–120° C.

C. In a similar manner, but replacing ethyl isothiocyanate with the appropriate isothiocyanate or isocyanate, the following compounds were made:

(±)-cis-2-(2-(4-chlorophenyl)ethyl)-2-(imidazol-1-yl)methyl-4-(4-(methylamino(carbonyl)amino)-phenylthio)methyl-1,3-dioxolane; m.p. 140°–141° C.; and (±)-cis-2-(2-(4-chlorophenyl)ethyl)-2-(imidazol-1-yl)methyl-4-(4-ethoxycarbonylamino(thiocarbonyl)aminophenoxy)methyl-1,3-dioxolane; m.p. 185°–186° C.

EXAMPLE 9

A. Sodium hydroxide (1.5 g) in water (15 mL) was added to a suspension of (±)-cis-2-(2-(4-chlorophenyl)ethyl)-2-(imidazol-1-yl)methyl-4-(4-ethoxycarbonylamino(thiocarbonyl)aminophenoxy)methyl-1,3-dioxolane (550 mg) in methanol (100 mL) and the resulting solution heated at 75° C. for 1 hour. Most of the methanol was then evaporated under reduced pressure and the product crystallized by the addition of water. Recrystallization from methanol/methylene chloride/ether gave (±)-cis-2-(2-(4-chlorophenyl)ethyl)-2-(imidazol-1-yl)methyl-4-(4-amino(thiocarbonyl)aminophenoxy)methyl-1,3-dioxolane (350 mg), double m.p. 163°–165°, 171°–172° C.

EXAMPLE 10

Compounds of Formula (I) wherein X is S(O)$_t$ where t is 1

A. A solution of m-chloroperbenzoic acid (80–85%) (1.42 g) in dichloromethane (50 mL) was added dropwise with stirring to a 0° C. solution of (2S,4S)-cis-2-(2-(4-chlorophenyl)ethyl)-2-(imidazol-1-yl)methyl-4-(4-aminophenylthio)methyl-1,3-dioxolane (3.00 g) in dichloromethane (50 mL) over 30 minutes. After an additional 30 minutes, saturated aqueous potassium carbonate solution (50 mL) was added and the mixture stirred and separated. The aqueous layer was extracted with dichloromethane (50 mL) and the combined extracts dried (Na$_2$SO$_4$) and evaporated to dryness. The resulting solid was dissolved in a small volume of dichloromethane/methanol and purified by flash chromatography (column size 3 in.×10 in.) eluting with 1–8% methanol in dichloromethane. After elution of some starting material and a minor side-product, the less polar sulfoxide, (2S,4S)-cis-2-(2-(4-chlorophenyl)ethyl)-2-(imidazol-1-yl)methyl-4-(4-aminophenylsulfinyl)methyl-1,3-dioxolane (0.85 g), m.p. 186°–187.8° C., [α]$_D$+152.6° (c=0.4, MeOH), was obtained; followed by the more polar diastereomer (0.89 g), m.p. 169.5°–171.0° C., [α]$_D$+4.7 (c=0.4, MeOH).

B. In a similar manner, but replacing (2S,4S)-cis-2-(2-(4-chlorophenyl)ethyl)-2-(imidazol-1-yl)methyl-4-(4-aminophenylthio)methyl-1,3-dioxolane with other compounds of formula (I) where X is —S(O)$_t$ where t is 0, the following compounds are made:

(2S,4S)-cis-2-(2-(4-methoxyphenyl)ethyl)-2-(imidazol-1-yl)methyl-4-(4-aminophenylsulfinyl)methyl-1,3-dioxolane;

(2S,4S)-cis-2-(2-(2,4-dichlorophenyl)ethyl)-2-(imidazol-1-yl)methyl-4-(4-aminophenylsulfinyl)methyl-1,3-dioxolane;

(2S,4S)-cis-2-(2-(4-chlorophenyl)ethyl)-2-(5-methylimidazol-1-yl)methyl-4-(4-aminophenylsulfinyl)methyl-1,3-dioxolane;

(2S,4S)-cis-2-(2-(4-fluorophenyl)ethyl)-2-(imidazol-1-yl)methyl-4-(4-aminophenylsulfinyl)methyl-1,3-dioxolane;

(2S,4S)-trans-2-(2-(4-chlorophenyl)ethyl)-2-(imidazol-1-yl)methyl-4-(4-aminophenylsulfinyl)methyl-1,3-dioxolane;

(2S,4S)-cis-2-(2-phenylethyl)-2-(5-methylimidazol-1-yl)methyl-4-(aminophenylsulfinyl)methyl-1,3-dioxolane;

(2R,4R)-cis-2-(2-(4-chlorophenyl)ethyl)-2-(imidazol-1-yl)methyl-4-(4-aminophenylsulfinyl)methyl-1,3-dioxolane; and (2R,4R)-cis-2-(2-(4-methoxyphenyl)ethyl)-2-(imidazol-1-yl)methyl-4-(4-aminophenylsulfinyl)methyl-1,3-dioxolane.

EXAMPLE 11

Compounds of Formula (I) wherein X is S(O)$_t$ where t is 2

A. A solution of m-chloroperbenzoic acid (0.94 g) in dichloromethane (30 mL) was added dropwise to a stirred solution of (2S,4S)-cis-2-(2-(4-chlorophenyl)ethyl-2-(imidazol-1-yl)methyl-4-(4-aminophenylthio)methyl-1,3-dioxolane (1.00 g) in dichloromethane at 0° C. over 30 minutes. After an additional 30 minutes, further m-chloroperbenzoic acid (0.25 g) was added. After stirring for a further 30 minutes, the reaction mixture was treated with saturated aqueous potassium carbonate solution, stirred and the layers separated. The aqueous phase was extracted with ethyl acetate, and the combined organic fractions concentrated and applied to a flash chromatography column (silica gel, 2½ in. × 12 in.). Elution with 1–5% methanol in dichloromethane gave pure product, (2S,4S)-cis-2-(2-(4-chlorophenyl)ethyl)-2-(imidazol-1-yl)methyl-4-(4-aminophenylsulfonyl)methyl-1,3-dioxolane, which was dissolved in methanol and converted to the hydrogen oxalate salt by addition of ether followed by ethereal oxalic acid (anhydrous) until precipitation was complete. The solid was filtered off and recrystallized from methanol-ethyl acetate to give the mono (hydrogen oxalate) salt (0.9 g), m.p. 181°–182° C.

B. In a similar manner, but replacing (2S,4S)-cis-2-(2-(4-chlorophenyl)ethyl)-2-(imidazol-1-yl)methyl-4-(4-aminophenylthio)methyl-1,3-dioxolane with other compounds of formula (I) where X is S(O)$_t$ where t is 0, the following compounds are made:

(2S,4S)-cis-2-(2-(4-methoxyphenyl)ethyl)-2-(imidazol-1-yl)methyl-4-(4-aminophenylsulfonyl)methyl-1,3-dioxolane;

(2S,4S)-cis-2-(2-(2,4-dichlorophenyl)ethyl)-2-(imidazol-1-yl)methyl-4-(4-aminophenylsulfonyl)methyl-1,3-dioxolane;

(2S,4S)-cis-2-(2-(4-chlorophenyl)ethyl)-2-(5-methylimidazol-1-yl)methyl-4-(4-aminophenylsulfonyl)methyl-1,3-dioxolane;

(2S,4S)-cis-2-(2-(4-fluorophenyl)ethyl)-2-(imidazol-1-yl)methyl-4-(4-aminophenylsulfonyl)methyl-1,3-dioxolane;

(2R,4S)-trans-2-(2-(4-chlorophenyl)ethyl)-2-(imidazol-1-yl)methyl-4-(4-aminophenylsulfonyl)methyl-1,3-dioxolane;

(2S,4S)-cis-2-(2-phenylethyl)-2-(5-methylimidazol-1-yl)methyl-4-(aminophenylsulfonyl)methyl-1,3-dioxolane;

(2R,4R)-cis-2-(2-(4-chlorophenyl)ethyl)-2-(imidazol-1-yl)methyl-4-(4-aminophenylsulfonyl)methyl-1,3-dioxolane; and (2R,4R)-cis-2-(2-(4-methoxyphenyl)ethyl)-2-(imidazol-1-yl)methyl-4-(4-aminophenylsulfonyl)methyl-1,3-dioxolane.

EXAMPLE 12

Salts of Compounds of formula (I)

A. (2S,4S)-cis-2-(2-(4-chlorophenyl)ethyl)-2-(imidazol-1-yl)methyl-4-(4-aminophenylthio)methyl-1,3-dioxolane (700 mg) in isopropanol (25 mL) was warmed with stirring until just dissolved. A solution of concentrated sulfuric acid dissolved in isopropanol was added dropwise until no further precipitation occurred, whereupon the flask was placed in an ice bath and ethyl acetate added (qs 50 mL). The cooled mixture was filtered and the resulting white solid washed with ethyl acetate and dried in air. After recrystallization from water (25 mL), the mixture was cooled in an ice bath, filtered, and the solid washed with ice water and dried to give the mono(hydrogen sulfate) salt of (2S,4S)-cis-2-(2-(4-chlorophenyl)ethyl)-2-(imidazol-1-yl)methyl-4-(4-aminophenylthio)methyl-1,3-dioxolane as fine white microcrystals (733 mg), m.p. 198°–200° C.

B. Maleic acid (116 mg) was dissolved in ethyl acetate (7mL) by warming. This solution was then added to a solution of (2S,4S)-cis-2-(2-(4-chlorophenyl)ethyl)-2-(imidazol-1-yl)methyl-4-(4-aminophenylthio)methyl-1,3-dioxolane in ethyl acetate (7 mL) (also prepared by warming). The resulting solution was warmed very briefly to disperse some minor turbidity. After seeding and scratching the solution was cooled and the solid collected by filtration and washed with ethyl acetate to give the mono(hydrogen maleate) salt of (2S,4S)-cis-2-(2-(4-chlorophenyl)ethyl)-2-(imidazol-1-yl)-methyl-4-(4-aminophenylthio)methyl-1,3-dioxolane as a sulfur yellow powder (370 mg) m.p. 101°–103° C.

C. A warm solution of maleic acid (233 mg) in ethyl acetate (7 mL) was added to a warm solution of (2S,4S)-cis-2-(2-(4-chlorophenyl)ethyl)-2-(imidazol-1-yl)methyl-4-(4-aminophenylthio)methyl-1,3-dioxolane (430 mg) in ethyl acetate (7 mL) as above. The resulting milkiness was discharged by the addition of a few drops of acetone with brief warming. Seeding and scratching followed by cooling and filtration gave the bis(hydrogen maleate) salt of (2S,4S)-cis-2-(2-(4-chlorophenyl)ethyl)-2-(imidazol-1-yl)methyl-4-(4-aminophenylthio)methyl-1,3-dioxolane as a yellow solid (523 mg), m.p. 90°–92° C. Slow evaporation of the mother liquor gave snow white needles (50 mg) of the same composition, m.p. 112°–114° C. (decomposition from 70° C.).

D. A solution of (2S,4S)-cis-2-(2-(4-chlorophenyl)ethyl)-2-(imidazol-1-yl)methyl-4-(4-aminophenylthio)-methyl-1,3-dioxolane (430 mg) in ethyl acetate (18 mL) was seeded with the mesylate salt, treated with methanesulfonic acid (>98%, 93 mg) in ethyl acetate (2 mL) dropwise with stirring and stirred until the precipitate was crystalline. The product was filtered under an N$_2$ blanket, washed with ethyl acetate and recrystallized from methanol-ethyl acetate to give the methanesulfonate salt of (2S,4S)-cis-2-(2-(4-chlorophenyl)ethyl)-2-(imidazol-1-yl)methyl-4-(4-aminophenylthio)methyl-1,3-dioxolane, (315 mg) m.p. 152°–154° C.

E. A suspension of (2S,4S)-cis-2-(2-(4-chlorophenyl)ethyl)-2-(imidazol-1-yl)methyl-4-(4-aminophenylthio)-methyl-1,3-dioxolane (3.225 g) in MeOH (35 mL) was treated dropwise with 86.2% H$_3$PO$_4$ (1.71 g; 2 equiv.) with stirring. The resulting solution was evaporated under reduced pressure. The residue was then dissolved in warm water (15 mL), filtered, and the filtrate was then treated dropwise with isopropanol until just turbid. After seeding and scratching had given a few crystals, isopropanol was added dropwise with scratching to induce crystallization until crystallization was complete (final volume 75 mL). An additional 25 mL of isopropanol was then added, the mixture was cooled in ice, filtered under N$_2$ and the solid was washed with ice-cooled isopropanol and dried in vacuo to give 4.27 g of the phosphate salt of (2S,4S)-cis-2-(2-(4-chlorophenyl)ethyl)-2-(imidazol-1-yl)methyl-4-(4-aminophenylthio)-methyl-1,3-dioxolane as a light white powder, m.p. 198°–200° C. (partial melt, 112°–130° C., 130°–190° C.).

F. A suspension of (2S,4S)-cis-2-(2-(4-chlorophenyl)ethyl-2-(imidazol-1-yl)methyl-4-(4-aminophenylthio)-methyl-1,3-dioxolane (4.00 g) in 50 mL of methanol was treated with 25 mL of 1N HCl (gas) in ether (Aldrich) (>2 equiv.). The resulting solution was then evaporated to dryness in vacuo and treated with acetonitrile (100 mL) and 2–3 mL of water to give a mass of white needles. Filtration (under an N$_2$ blanket) and washing with wet acetonitrile, then acetonitrile and drying in vacuo gave 3.89 g of the dihydrochloride salt of (2S,4S)-cis-2-(2-(4-chlorophenyl)ethyl)-2-(imidazol-1-yl)methyl-4-(4-aminophenylthio)methyl-1,3-dioxolane, m.p. 130°–138° C. (foamlike, partial melt 112°–130° C.). Crystallization of the salt from isopropyl alcohol/ethyl acetate containing 1-2% water gave a product with m.p. ~126° C. (dec).

EXAMPLE 13

Conversion of Salts of Compounds of Formula (I) To the Free Bases

A. A solution of the dihydrochloride salt of (2S,4S)-cis-2-(2-(4-chlorophenyl)ethyl)-2-(imidazol-1-yl)methyl-4-(4-aminophenylthio)methyl-1,3-dioxolane (1.0 g) in water (10 mL) is treated with excess aqueous $K_2CO_3$ solution and the mixture extracted with methylene chloride (2×20 mL). The combined extracts are washed, dried ($MgSO_4$) and evaporated to dryness. Recrystallization from ethyl acetate/hexane gave the free base, (2S,4S)-cis-2-(2-(4-chlorophenyl)ethyl)-2-(imidazol-1-yl)methyl-4-(4-aminophenylthio)methyl-1,3-dioxolane, m.p. 121°-121.5° C.

EXAMPLE 14

This example illustrates the preparation of a representative pharmaceutical formulation for oral administration containing a compound of formula (I), or a pharmaceutically acceptable salt thereof, e.g., (2S,4S)-cis-2-(2-(4-chlorophenyl)ethyl)-2-(imidazol-1-yl)methyl-4-(4-aminophenylthio)methyl-1,3-dioxolane.

| Ingredients | |
|---|---|
| Compound of formula (I) | 200 mg |
| lactose, spray-dried | 148 mg |
| magnesium stearate | 2 mg |

The above ingredients are mixed and introduced into a hard-shell gelatin capsule. Alternatively, the mixture may be introduced into a soft elastic capsule.

Other compounds of formula (I), such as those prepared in accordance with Examples 1-6, can be used as the compound in the preparation of the orally administrable formulations of this example.

EXAMPLE 15

This example illustrates the preparation of a representative pharmaceutical formulation containing a compound of formula (I), or a pharmaceutically acceptable salt thereof, e.g., (2S,4S)-cis-2-(2-(4-chlorophenyl)ethyl)-2-(imidazol-1-yl)methyl-4-(4-acetylaminophenylthio)methyl-1,3-dioxolane.

An injectable preparation is prepared having the following composition:

| Ingredients | |
|---|---|
| Compound of formula (I) | 1.0% |
| Mannitol | 4.0% |
| HCl (1N) | q.s. to pH 3 |
| water for injection | q.s. to 100.0% |

Other compounds of formula (I), such as those prepared in accordance with Examples 1-6, can be used as the compound in the preparation of the injectable formulations of this example.

EXAMPLE 16

This example illustrates the preparation of a representative pharmaceutical formulation containing a compound of formula (I), or a pharmaceutically acceptable salt thereof, e.g., (2S,4R)-cis-2-(2-(4-chlorophenyl)ethyl)-2-(imidazol-1-yl)methyl-4-(4-aminophenoxy)methyl-1,3-dioxolane.

A suppository totalling 2.5 grams is prepared having the following composition:

| Compound of formula (I) | 500 mg |
|---|---|
| witepsol H-15* | balance |

(*triglycerides of saturated vegetable fatty acid: a product of Riches-Nelson, Inc., New York, N.Y.).

Other compounds of formula (I), such as those prepared in accordance with Examples 1-6, can be used as the active compound in the preparation of the suppository formulations of this example.

EXAMPLE 17

In vitro Assays

The in vitro assays demonstrated the ability of compounds of formula (I) to inhibit cholesterol synthesis. In addition, the following in vitro assays demonstrated the ability of compounds of formula (I) wherein the 2-carbon of the dioxolane ring has the S-configuration to be more effective inhibitors of lanosterol 14α-demethylase than other cytochrome P-450 enzymes.

In the following assays, microsomes and mitochondria were prepared by methods described in *Arch. Biochem. Biophys.* (1986) Vol. 248, pp. 658-676, and *Arch. Biochem. Biophys.* (1966), Vol. 117, pp. 660-673; rat microsomes for the lanosterol 14α-demethylase and cholesterol 7α-hydroxylase assays were obtained from livers of animals treated with cholestyramine; human microsomes were obtained from liver samples; microsomes for the progesterone 17α/20 lyase assay were obtained from testes of perinatal pigs (<2 weeks old); mitochondria for the deoxycorticosterone 11β-hydroxylase assay were obtained from bovine adrenals; and microsomes for the estrogen synthase assay were obtained from human placenta. Protein was determined by the Lowery method as described in *J. Biol. Chem.* (1951), Vol. 193, pp. 265-275.

A. Lanosterol 14a-demethylase. The microsomal incubations contained potassium phosphate buffer (0.02M, pH 7.0), dithiothreitol (0.3 mM), EDTA (0.01 mM), magnesium chloride (3 mM), Tween-20 (0.005%), glycerol (20%), G-6-P dehydrogenase (one unit), microsomal protein (247 μg containing 0.187 nmol cytochrome P-450), a compound of formula (I) (20 μL methanol), and [32-$^3$H]-24,25-dihydrolanosterol (40.8 nmol in 20 μL ethanol) in a total volume of 1 mL. The mixture was vortexed and maintained at 4° C. until the reaction was initiated with NADPH (1.0 μmol). Tubes were incubated for 30 minutes at 37° C. The incubations were terminated using 250 μl of a 40% TCA solution. Bond-Elut extraction columns were activated with methanol (1×1 mL) followed by deionized water (2×1 mL). The reaction products, tritiated water and tritiated formate, were separated from the unreacted [32-$^3$H]-24,25-dihydrolanosterol using activated Bond-Elut columns. Duplicate 400 μl aliquots of the eluate were mixed with 10 mL Beta-Blend liquid scintillation fluid and were analyzed for radioactive content.

B. Cholesterol 7α-hydroxylase. Incubations contained hepatic microsomes (1 mg protein; 0.14 μmol endogenous cholesterol substrate), NADPH (1.0 μmol), magnesium chloride (3 μmol), EDTA (0.1 μmol), cysteamine hydrochloride (20 μmol), and potassium phosphate buffer, pH 7.4 (100 μmol) in a total volume of 1 mL and were agitated for 10 min. at 37° C. following addition of NADPH. Compounds of formula (I) were added to the incubation tubes in 20 μL of methanol, and solvent was evaporated prior to addition of the other components. After the 10 min. incubation period, the cytochrome P-450 mediated reactions were stopped by the addition of sodium cholate (5 mg) to solubilize the membranes and products were converted to their 4-cholestene-3-ones by the addition of cholesterol oxidase (0.23 units dissolved in 100 μL 10 mM potassium phosphate buffer containing 20% glycerol and 1 mM dithiothreitol) and agitation for 20 min. at 37° C. All reactions were terminated by addition of 1 mL methanol followed by 5 mL of petroleum ether. After mixing and centrifugation of the samples, the organic phases were evaporated under a stream of nitrogen and the residues were dissolved in 100 μL of isopropanol and analyzed by HPLC. HPLC analysis of metabolic reactions was performed on a Varian 5000 liquid chromatograph, equipped with a Wisp 710B autosampler and a Kratos SF 769 UV detector (240 nm). Separation of products was achieved with two 5 μm, 25 cm silica columns (Dupont Zorbax Sil or Beckman Ultrasphere Sil) preceded by a silica packed 3 cm guard column. The columns were eluted with hexane/isopropanol under the following conditions: 12 min. isocratic at 95/5; 5 min. with a linear gradient to 70/30 and 23 min. isocratic at 70/30. All chromatographic separations were performed at room temperature.

C. Progesterone 17α/20 lyase. Incubations with testes microsomes contained protein (0.024-1 mg), NADPH (1 μmol), magnesium chloride (3 μmol), potassium phosphate buffer, pH 7.25 (100 μmol), 17α-hydroxyprogesterone (0.5-25 nmol in 20 μL of MeOH), and a compound of formula (I) (in 20 μL MeOH) in a total volume of 1 mL and were agitated at 37° C. for 10 min. All reactions were terminated by addition of 6 mL of methylene chloride followed immediately by 1 nmol of internal standard (11β-hydroxytestosterone) in 50 μL MeOH. After mixing and centrifugation of the samples, the organic phases were evaporated under a stream of nitrogen, and the residues were dissolved in 200 μL MeOH and analyzed by HPLC. Separation of substrate (17α-hydroxyprogesterone), product (androstenedione), and internal standard was achieved with a Jones Chromatography 5-μm, 25-cm, ODS column. The column was eluted with methanol/acetonitrile/water under the following conditions: 3 min. isocratic at 2/13/85; 7 min. linear gradient to 20/30/50; 12 min. isocratic at those conditions; 3 min. linear gradient to 20/75/5; followed by 5 min. isocratic at those conditions. Turnover numbers were calculated by comparing peak height of internal standard to peak height of androstenedione.

D. Deoxycorticosterone 11β-hydroxylase. Incubations with bovine adrenal mitochondria contained protein (0.05 mg), NADPH (1 μmol), magnesium chloride (3 μmol), potassium phosphate buffer, pH 7.4 (100 μmol), deoxycorticosterone (0.5-25 nmol in 20 μL of MeOH), and a compound of formula (I) (in 20 μL MeOH) in a total volume of 1 mL and were agitated at 37° C. for 10 min. Mitochondria were sonicated 5 min. on ice before addition to the incubation mixture. All reactions were terminated by addition of 6 mL of methylene chloride followed immediately by 1 nmol of internal standard (11β-hydroxytestosterone) in 50 μL MeOH. After mixing and centrifugation of the samples, the organic phases were evaporated under a stream of nitrogen, and the residues were dissolved in 200 μL MeOH and analyzed by HPLC. HPLC conditions were the same as described in Swinney, D., et al., *Biochemistry* (1987), Vol. 26, pp. 7073-7083, for the separation of progesterone metabolites. Turnover numbers were calculated by comparing peak height of internal standard to peak height of the product, corticosterone.

E. Estrogen synthase. The microsomal incubations contained potassium phosphate buffer (pH 7.4, 50 mM), dithiothreitol (0.3 mM), microsomal protein (0.1 mg), a compound of formula (I) (in 20 μl methanol), androst-4-ene-3,17-dione (1β,2β-[$^3$H$_2$]) (androstenedione) (1 nmol in 20 μL methanol), and NAPDH (1.0 μmol) in a total volume of 1 mL. The incubation mixture was maintained at 4° C. until the reaction was initiated. The tubes were incubated for 10 min. in a shaking water bath at 37° C. The reactions were terminated using 25 μl of a 40% TCA solution.

Bond-Elut extraction columns were activated with methanol (1×1 mL) followed by deionized water (2×1 mL). Tritiated water was separated from the unreacted androstenedione using activated Bond-Elut columns. Duplicate 400 μl aliquots of the eluate were mixed with 10 mL Beta-Blend liquid scintillation fluid and were analyzed for radioactive content.

EXAMPLE 18

In vitro Assay

The ability of compounds of formula (I) to inhibit intracellular cholesterol synthesis was demonstrated using human skin fibroblasts by a modification of the method described by Kraemer et al., supra. Fibroblasts were grown in a monolayer to approximately 90% confluence in a humidified incubator (95% air-5% $CO_2$) at 37° C. in Modified Eagles medium (MEM) containing 10% fetal bovine serum (FBS), penicillin (100 U/mL) and streptomycin (100 mg/mL). Human fibroblasts were incubated overnight in 60 mm culture dishes in 4 mL MEM containing 10% lipoprotein-deficient serum (LDS), washed twice with serum-free medium (SFM) and incubated in triplicate with the compound of formula (I) to be tested dissolved in ethanol at a final concentration of $10^{-12}$ to $10^{-6}$M in SFM at 37° C. for 1 hr. Sodium 2-[$^{14}$C] acetate (5 μC/mL) was then added and the cultures were incubated at 37° C. for 2 hr. The dishes were then placed on ice, washed three times with PBS and the cells were scraped off the plate and dispersed in 5 mL of PBS. An aliquot was removed for protein determination using the Biorad reagent and carrier cholesterol (250 μg), lanosterol (250 μg) plus [$^3$H]-cholesterol (20,000 dpm) were added to the cell suspension which were saponified in 7.5% alcoholic KOH at 80° C. for 2 hr. The non-saponifiable lipids were then extracted with petroleum ether. The ether extracts were concentrated by evaporation under $N_2$, dissolved in 200 μL of hexane and 120 μL aliquots fractionated by TLC on silica gel H plates developed in 25% ethyl acetate-75% hexane (v/v). The sterol bands were visualized by exposure to $I_2$ vapor and areas corresponding to cholesterol, methyl-sterols, squalene-oxide and squalene were scraped off the plate and radioactivity measured in a Packard Tri Carb liquid scintillation spectrophotometer. Radioactivity was adjusted for recovery of [$^3$H]-cholesterol and cholesterol synthesis expressed as dpm/mg call protein/hr.

EXAMPLE 19

In vivo Assays

Compounds of formula (I) were administered to groups of eight male Golden Syrian hamsters (90-110 grams) by gavage in 0.5 mL of propylene glycol once or twice daily for three days. Eight animals received vehicle only. On the night following the last dose, the animals were fasted and given water ad libitum. On the fourth day the animals were bled by cardiac puncture and the serum was collected. Serum cholesterol levels of all the animals, including control, were determined using an enzymatic kit assay (Sigma).

Compounds of formula (I) exhibited the ability to lower serum cholesterol when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a mammal having a disease-state characterized by hypercholesterolemia, which method comprises administering to a mammal in need thereof a therapeutically effective amount of a compound of formula (I):

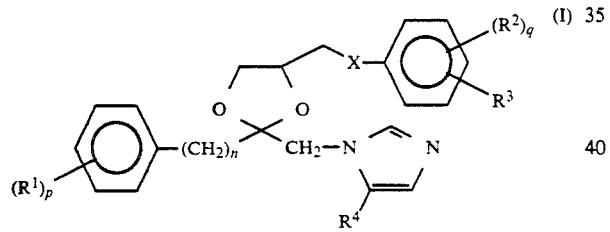

wherein
n is 2 or 3;
p is 0, 1 or 2;
q is 0, 1 or 2;
X is oxygen or $S(O)_t$ where t is 0, 1 or 2;
each $R^1$ is independently halo, lower alkyl, lower alkoxy, or trifluoromethyl;
each $R^2$ is independently halo or lower alkyl;
$R^3$ is nitro or $-N(R^5)R^6$ where
  $R^5$ is hydrogen or lower alkyl;
  $R^6$ is hydrogen, lower alkyl, lower alkylsulfonyl or $-C(Y)R^7$ where Y is oxygen or sulfur and $R^7$ is hydrogen, lower alkyl, lower alkoxy or $-N(R^8)R^9$ where $R^8$ is hydrogen or lower alkyl and $R^9$ is hydrogen, lower alkyl or lower alkoxycarbonyl; or
  $R^5$ and $R^6$ together with N is pyrrolidino, piperidino, morpholino, thiomorpholino or piperazino, wherein the piperazino is optionally substituted at the 4-position by $-C(O)R^{10}$ where $R^{10}$ is hydrogen, lower alkyl, lower alkoxy or amino; and
$R^4$ is hydrogen or lower alkyl, as a single stereoisomer or as a mixture thereof; or a pharmaceutically acceptable salt thereof.

2. A pharmaceutical composition useful for treating a mammal having a disease-state characterized by hypercholesterolemia, which composition comprises a pharmaceutically acceptable excipient and a therapeutically effective amount of a compound of formula (I):

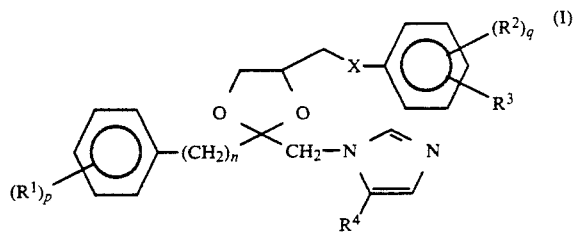

wherein
n is 2 or 3;
p is 0, 1 or 2;
q is 0, 1 or 2;
X is $S(O)_t$ where t is 0, 1 or 2;
each $R^1$ is independently halo, lower alkyl, lower alkoxy, or trifluoromethyl;
each $R^2$ is independently halo or lower alkyl;
$R^3$ is nitro or $-N(R^5)R^6$ where
  $R^5$ is hydrogen or lower alkyl;
  $R^6$ is hydrogen, lower alkyl, lower alkylsulfonyl or $-C(Y)R^7$ where Y is oxygen or sulfur and $R^7$ is hydrogen, lower alkyl or $-N(R^8)R^9$ where $R^8$ is hydrogen or lower alkyl and $R^9$ is hydrogen, lower alkyl or lower alkoxycarbonyl; or
  $R^5$ and $R^6$ together with N is morpholino, thiomorpholino or piperazino, wherein the piperazino is optionally substituted at the 4-position by $-C(O)R^{10}$ where $R^{10}$ is hydrogen, lower alkyl, lower alkoxy or amino; and
$R^4$ is hydrogen or lower alkyl, as a single stereoisomer or as a mixture thereof; or a pharmaceutically acceptable salt thereof.

3. A compound of formula (I):

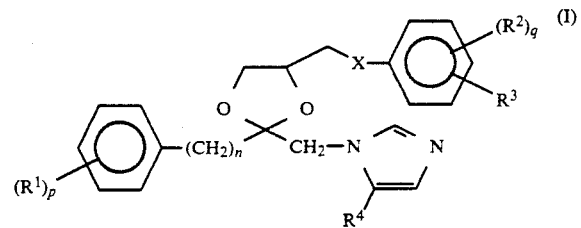

wherein
n is 2 or 3;
p is 0, 1 or 2;
q is 0, 1 or 2;
X is $S(O)_t$ where t is 0, 1 or 2;
each $R^1$ is independently halo, lower alkyl, lower alkoxy, or trifluoromethyl;
each $R^2$ is independently halo or lower alkyl;
$R^3$ is nitro or $-N(R^5)R^6$ where
  $R^5$ is hydrogen or lower alkyl;
  $R^6$ is hydrogen, lower alkyl, lower alkylsulfonyl or $-C(Y)R^7$ where Y is oxygen or sulfur and $R^7$ is hydrogen, lower alkyl, lower alkoxy or $-N(R^8)R^9$ where $R^8$ is hydrogen or lower alkyl and $R^9$ is hydrogen, lower alkyl or lower alkoxycarbonyl; or R⁵ and R⁶ together with N is pyrrolidino, piperidino, morpholino, thiomorpholino or piperazino, wherein the piperazino is optionally substituted at the 4-position by —C(O)R¹⁰ where R¹⁰ is hydrogen, lower alkyl, lower alkoxy or amino; and R⁴ is hydrogen or lower alkyl, as a single stereoisomer or as a mixture thereof; or a pharmaceutically acceptable salt thereof.

4. A compound of claim 3 wherein the 2-carbon of the dioxolane ring has the S-configuration.

5. A compound of claim 4 wherein n is 2, q is 0, and R⁴ is hydrogen.

6. A compound of claim 5 wherein R³ is in the 4-position and is —N(R⁵)R⁶ where R⁵ is hydrogen or lower alkyl and R⁶ is hydrogen, lower alkyl, lower alkylsulfonyl or —C(Y)R⁷ where Y is oxygen or sulfur and R⁷ is hydrogen, lower alkyl, lower alkoxy, or —N(R⁸)R⁹ where R⁸ is hydrogen or lower alkyl and R⁹ is hydrogen, lower alkyl or lower alkoxycarbonyl.

7. A compound of claim 6 wherein R¹ is chloro, fluoro, methyl or methoxy.

8. A compound of claim 7 wherein R⁵ is hydrogen and R⁶ is hydrogen or —C(Y)R⁷ where Y is oxygen and R⁷ is hydrogen, lower alkyl or lower alkoxy.

9. A compound of claim 8 wherein p is 1, t is 0 and R¹ is chloro in the 4-position.

10. The cis-enantiomer of a compound of claim 9 wherein R⁶ is hydrogen, namely, (2S,4S)-cis-2-(2-(4-chlorophenyl)ethyl)-2-(imidazol-1-yl)methyl-4-(4-aminophenylthio)methyl-1,3-dioxolane, or a pharmaceutically acceptable salt thereof.

11. The compound of claim 10 together with its corresponding (2R,4R)-cis-enantiomer, namely, (±)-cis-2-(2-(4-chlorophenyl)ethyl)-2-(imidazol-1-yl)methyl-4-(4-aminophenylthio)methyl-1,3-dioxolane, or a pharmaceutically acceptable salt thereof.

12. The trans-enantiomer of a compound of claim 9 wherein R⁶ is hydrogen, namely, (2S,4R)-trans-2-(2-(4-chlorophenyl)ethyl)-2-(imidazol-1-yl)methyl-4-(4-aminophenylthio)methyl-1,3-dioxolane, or a pharmaceutically acceptable salt thereof.

13. The compound of claim 12 together with its corresponding (2R,4S)-trans-enantiomer, namely, (±)-trans-2-(2-(4-chlorophenyl)ethyl-2-(imidazol-1-yl)methyl-4-(4-aminophenylthio)methyl-1,3-dioxolane, or a pharmaceutically acceptable salt thereof.

14. The cis-enantiomer of a compound of claim 9 wherein R⁶ is acetyl, namely, (2S,4S)-cis-2-(2-(4-chlorophenyl)ethyl)-2-(imidazol-1-yl)methyl-4-(4-acetamidophenylthio)methyl-1,3-dioxolane, or a pharmaceutically acceptable salt thereof.

15. The compound of claim 14 together with its corresponding (2R,4R)-cis-enantiomer, namely, (±)-cis-2-(2-(4-chlorophenyl)ethyl)-2-(imidazol-1-yl)methyl-4-(4-acetamidophenylthio)methyl-1,3-dioxolane, or a pharmaceutically acceptable salt thereof.

16. The trans-enantiomer of a compound of claim 9 wherein R⁶ is acetyl, namely, (2S,4R)-trans-2-(2-(4-chlorophenyl)ethyl)-2-(imidazol-1-yl)methyl-4-(4-acetamidophenylthio)methyl-1,3-dioxolane, or a pharmaceutically acceptable salt thereof.

17. The compound of claim 16 together with its corresponding (2R,4S)-trans-enantiomer, namely, (±)-trans-2-(2-(4-chlorophenyl)ethyl)-2-(imidazol-1-yl)methyl-4-(4-acetamidophenylthio)methyl-1,3-dioxolane, or a pharmaceutically acceptable salt thereof.

18. A compound of claim 8 wherein p is 1, t is 0 and R¹ is methoxy in the 4-position.

19. The cis-enantiomer of a compound of claim 18 wherein R⁶ is hydrogen, namely (2S,4S)-cis-2-(2-(4-methoxyphenyl)ethyl)-2-(imidazol-1-yl)methyl-4-(4-aminophenylthio)methyl-1,3-dioxolane, or a pharmaceutically acceptable salt thereof.

20. The compound of claim 19 together with its corresponding (2R,4R)-cis-enantiomer, namely, (±)-cis-2-(2-(4-methoxyphenyl)ethyl-2-(imidazol-1-yl)methyl-4-(4-aminophenylthio)methyl-1,3-dioxolane, or a pharmaceutically acceptable salt thereof.

21. A compound of claim 8 wherein p is 1, t is 0 and R¹ is fluoro in the 4-position.

22. The cis-enantiomer of a compound of claim 21 wherein R⁶ is hydrogen, namely (2S,4S)-cis-2-(2-(4-fluorophenyl)ethyl)-2-(imidazol-1-yl)methyl-4-(4-aminophenylthio)methyl-1,3-dioxolane, or a pharmaceutically acceptable salt thereof.

23. A compound of claim 8 wherein p is 0 and t is 0.

24. The cis-enantiomer of a compound of claim 23 wherein R⁶ is hydrogen, namely, (2S,4S)-cis-2-(2-phenylethyl)-2-(imidazol-1-yl)methyl-4-(4-aminophenylthio)methyl-1,3-dioxolane, or a pharmaceutically acceptable salt thereof.

25. A compound of claim 8 wherein p is 2, t is 0, and one R¹ is chloro in the 2-position and the other R¹ is chloro in the 4-position.

26. The cis-enantiomer of a compound of claim 25 wherein R⁶ is hydrogen, namely, (2S,4S)-cis-2-(2-(2,4-dichlorophenyl)ethyl)-2-(imidazol-1-yl)methyl-4-(4-aminophenylthio)methyl-1,3-dioxolane, or a pharmaceutically acceptable salt thereof.

27. A compound of formula (I):

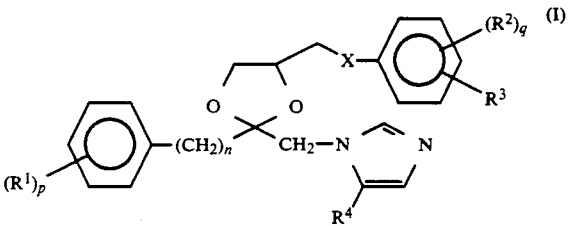

wherein
n is 2 or 3;
p is 0, 1 or 2;
q is 0, 1 or 2;
X is oxygen;
each R¹ is independently halo, lower alkyl, lower alkoxy, or trifluoromethyl;
each R² is independently halo or lower alkyl;
R³ is nitro or —N(R⁵)R⁶ where
  R⁵ is hydrogen or lower alkyl;
  R⁶ is hydrogen, lower alkyl, lower alkylsulfonyl or —C(Y)R⁷ where Y is oxygen or sulfur and R⁷ is hydrogen, lower alkyl or —N(R⁸)R⁹ where R⁸ is hydrogen or lower alkyl and R⁹ is hydrogen, lower alkyl or lower alkoxycarbonyl; or
  R⁵ and R⁶ together with N is morpholino, thiomorpholino or piperazino, wherein the piperazino is optionally substituted at the 4-position by —C(O)R¹⁰ where R¹⁰ is hydrogen, lower alkyl, lower alkoxy or amino; and
R⁴ is hydrogen or lower alkyl, as a single stereoisomer or as a mixture thereof; or a pharmaceutically acceptable salt thereof.

28. A compound of claim 27 wherein the 2-carbon of the dioxolane ring has the S-configuration.

29. A compound of claim 28 wherein n is 2, q is 0, and R⁴ is hydrogen.

30. A compound of claim 29 wherein R³ is in the 4-position and is —N(R⁵)R⁶ where R⁵ is hydrogen or lower alkyl and R⁶ is hydrogen, lower alkyl, lower alkylsulfonyl, or —C(Y)R⁷ where Y is oxygen or sulfur and R⁷ is hydrogen, lower alkyl, or —N(R⁸)R⁹ where R⁸ is hydrogen or lower alkyl and R⁹ is hydrogen, lower alkyl or lower alkoxycarbonyl.

31. A compound of claim 30 wherein R¹ is chloro, fluoro, methyl or methoxy.

32. A compound of claim 31 wherein R⁵ is hydrogen and R⁶ is hydrogen or —C(Y)R⁷ where Y is oxygen and R⁷ is hydrogen or lower alkyl.

33. The cis-enantiomer of a compound of claim 32 wherein p is 1, R¹ is chloro in the 4-position and R⁶ is hydrogen, namely, (2S,4R)-cis-2-(2-(4-chlorophenyl)ethyl)-2-(imidazol-1-yl)methyl-4-(4-aminophenoxy)-methyl-1,3-dioxolane, or a pharmaceutically acceptable salt thereof.

34. The compound of claim 33 together with its corresponding (2R,4S)-cis-enantiomer, namely, (±)-cis-2-(2-(4-chlorophenyl)ethyl)-2-(imidazol-1-yl)methyl-4-(4-aminophenoxy)methyl-1,3-dioxolane, or a pharmaceutically acceptable salt thereof.

35. The cis-enantiomer of a compound of claim 32 wherein p is 1, R¹ is chloro in the 4-position and R⁶ is acetyl, namely, (2S,4R)-cis-2-(2-(4-chlorophenyl)ethyl)-2-(imidazol-1-yl)methyl-4-(4-acetamidophenoxy)methyl-1,3-dioxolane.

36. The compound of claim 35 together with its corresponding (2R,4S)-enantiomer, namely, (±)-cis-2-(2-(4-chlorophenyl)ethyl)2-(imidazol-1-yl)methyl-4-(4-acetamidophenoxy)methyl-1,3-dioxolane.

37. The method of claim 1 wherein the compound of formula (I) is (2S,4S)-cis-2-(2-(4-chlorophenyl)ethyl)-2-(imidazol-1-yl)methyl-4-(4-aminophenylthio)methyl-1,3-dioxolane, or a pharmaceutically acceptable salt thereof.

38. The composition of claim 2 wherein the compound of formula (I) is (2S,4S)-cis-2-(2-(4-chlorophenyl)ethyl)-2-(imidazol-1-yl)methyl-4-(4-aminophenylthio)methyl-1,3-dioxolane, or a pharmaceutically acceptable salt thereof.

* * * * *

UNITED STATES PATENT AND TRADEMARK OFFICE
CERTIFICATE OF CORRECTION

PATENT NO. : 5,158,949
DATED : October 27, 1992
INVENTOR(S) : Keith M. Walker, et al.

It is certified that error appears in the above-indentified patent and that said Letters Patent is hereby corrected as shown below:

Column 44, line 54, "$[\alpha]_D +13.6°$" should read -- $[\alpha]_D -18.7°$ --.

Column 45, line 17, "$[\alpha]_D -18.7°$" should read -- $[\alpha]_D +13.6°$ --.

Signed and Sealed this

Fifteenth Day of March, 1994

Attest:

BRUCE LEHMAN

Attesting Officer    Commissioner of Patents and Trademarks